(12) United States Patent
McGovern et al.

(10) Patent No.: US 10,626,180 B2
(45) Date of Patent: Apr. 21, 2020

(54) METHODS OF TREATING AND PREDICTING NON-RESPONSE TO ANTI-TNF TREATMENT IN SUBJECTS WITH INFLAMMATORY BOWEL DISEASE

(71) Applicant: Cedars-Sinai Medical Center, Los Angeles, CA (US)

(72) Inventors: Dermot McGovern, Los Angeles, CA (US); Stephan Targan, Santa Monica, CA (US); Dalin Li, Walnut, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 15/957,457

(22) Filed: Apr. 19, 2018

(65) Prior Publication Data

US 2018/0305459 A1 Oct. 25, 2018

Related U.S. Application Data

(60) Provisional application No. 62/487,971, filed on Apr. 20, 2017.

(51) Int. Cl.
| | |
|---|---|
| *A61P 1/00* | (2006.01) |
| *G01N 33/68* | (2006.01) |
| *C12Q 1/6827* | (2018.01) |
| *C12Q 1/6883* | (2018.01) |
| *A61K 39/395* | (2006.01) |
| *A61K 39/00* | (2006.01) |
| *C07K 16/28* | (2006.01) |
| *C07K 16/24* | (2006.01) |

(52) U.S. Cl.
CPC ............ *C07K 16/2875* (2013.01); *A61P 1/00* (2018.01); *C12Q 1/6827* (2013.01); *C12Q 1/6883* (2013.01); *G01N 33/6854* (2013.01); *G01N 33/6863* (2013.01); *A61K 39/3955* (2013.01); *A61K 39/39541* (2013.01); *A61K 2039/505* (2013.01); *C07K 16/241* (2013.01); *C07K 2317/76* (2013.01); *C12Q 2600/106* (2013.01); *C12Q 2600/156* (2013.01); *G01N 2800/065* (2013.01); *G01N 2800/52* (2013.01); *G01N 2800/56* (2013.01)

(58) Field of Classification Search
CPC .............. C07K 16/241; C07K 16/2875; C07K 2317/76; G01N 33/00; G01N 33/6854; G01N 33/6863; G01N 2800/065; G01N 2800/52; G01N 2800/56; C12Q 1/6827; C12Q 1/6883; C12Q 2600/106; C12Q 2600/156; A61P 1/00; A61K 2039/505; A61K 39/39541; A61K 39/3955
See application file for complete search history.

(56) References Cited

U.S. PATENT DOCUMENTS

| | | |
|---|---|---|
| 5,874,233 A | 2/1999 | Targan et al. |
| 2007/0037165 A1 | 2/2007 | Venter et al. |
| 2011/0160085 A1 | 6/2011 | Li et al. |
| 2012/0094934 A1 | 4/2012 | Collard et al. |

FOREIGN PATENT DOCUMENTS

WO WO-2018195328 A1 10/2018

OTHER PUBLICATIONS

Li D, et al. (Jun. 2016) Inflammatory Bowel Disease. 22(6):1346-1352. (doi: 10.1097/MIB.0000000000000771).*
Casina TS (2006) Immunohematology. 22(4):196-202.*
Medrano et al. Role of TNFRSF1B polymorphisms in the response of Crohn's disease patients to infliximab. Human Immunology 75(1):71-75 (2014).
PCT/US2018/028397 International Search Report and Written Opinion dated Jul. 9, 2018.
Pierik et al. Tumour Necrosis Factor-α Receptor 1 and 2 Polymorphisms in Inflammatory Bowel Disease and their Association with Response to Infliximab. Alimentary Pharmacology & Therapeutics 20(3):303-310 (2004).
Mow et al., Association of antibody responses to microbial antigens and complications of small bowel Crohn's disease. Gastroenterology 126:414-424 (2004).
Yoon et al. Colonic Phenotypes Are Associated with Poorer Response to Anti-TNF Therapies in Patients with IBD. Inflammatory Bowel Diseases. 23(8):1382-1393 (2017).

* cited by examiner

*Primary Examiner* — Robert S Landsman
(74) *Attorney, Agent, or Firm* — Wilson Sonsini Goodrich & Rosati

(57) ABSTRACT

The aspects disclosed herein describe methods of identifying a subject that is non-responsive to anti-TNF therapy. The aspects disclosed herein further provide for a method of selecting a therapy for a subject with Inflammatory Bowel Disease (IBD), and treating the subject with the therapy.

18 Claims, 3 Drawing Sheets

Specification includes a Sequence Listing.

SEQUENCE LISTING

```
<160> NUMBER OF SEQ ID NOS: 240

<210> SEQ ID NO 1
<211> LENGTH: 146
<212> TYPE: DNA
<213> ORGANISM: Homo sapiens

<400> SEQUENCE: 1
tgctcccggg ggtcctggga aggcacaatg gtgacagtgc tgcagctctg cactcctgga      60
gggtcactca gagacycgag agaggagggc tctgcgtctg ctcctctgtc cagggctgta     120
gcttctctgg gtgcctttgc ttttct                                          146

<210> SEQ ID NO 2
<211> LENGTH: 161
<212> TYPE: DNA
<213> ORGANISM: Homo sapiens

<400> SEQUENCE: 2
tggtttctca tctcaatgtt tgacaagttt gtttcagttg ttatagtctg ttctcagttt      60
ttatgcactg cctttttgaa ygttaggttt acttttttaa ttgacaagta aaaattgtat     120
agtatattta tgttgtagag catgaaattt tgatatatgc c                         161

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 3

Gly Phe Thr Phe Ser Thr Tyr Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Ser Gly Thr Gly Arg Thr Thr
1               5

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Lys Glu Arg Gly Asp Tyr Tyr Tyr Gly Val Phe Asp Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Thr Ile Ser Ser Trp
1               5

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Ser
1

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr His Arg Ser Trp Thr
1               5

<210> SEQ ID NO 9

```
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Leu Glu Ser Gly Gly Gly Leu Val Gln Pro Gly Lys
1               5                   10                  15

Ser Leu Arg Leu Ser Cys Ala Val Ser Gly Phe Thr Phe Ser Thr Tyr
            20                  25                  30

Gly Met Asn Trp Val Arg Gln Ala Pro Gly Lys Gly Leu Glu Trp Val
        35                  40                  45

Ser Ser Ile Ser Gly Thr Gly Arg Thr Thr Tyr His Ala Asp Ser Val
    50                  55                  60

Gln Gly Arg Phe Thr Val Ser Arg Asp Asn Ser Lys Asn Ile Leu Tyr
65                  70                  75                  80

Leu Gln Met Asn Ser Leu Arg Ala Asp Asp Thr Ala Val Tyr Phe Cys
                85                  90                  95

Thr Lys Glu Arg Gly Asp Tyr Tyr Gly Val Phe Asp Tyr Trp Gly
            100                 105                 110

Gln Gly Thr Leu Val Thr Val Ser Ser
        115                 120

<210> SEQ ID NO 10
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Ser Ser Trp
            20                  25                  30

Leu Ala Trp Tyr Gln Gln Thr Pro Glu Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Arg Ser Trp Thr
                85                  90                  95

Phe Gly Gln Gly Thr Lys Val Glu Ile Thr
            100                 105

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Thr Phe Ser Ser Tyr Trp
1               5
```

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Lys Glu Asp Gly Ser Glu Lys
1               5

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Arg Glu Asp Tyr Asp Ser Tyr Tyr Lys Tyr Gly Met Asp Val
1               5                   10                  15

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Ile Leu Tyr Ser Ser Asn Asn Lys Asn Tyr
1               5                   10

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Ala Ser
1

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Tyr Tyr Ser Thr Pro Phe Thr
1               5

<210> SEQ ID NO 17
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Val Asp Ser Val
    50                  55                  60

Lys Gly Arg Phe Thr Leu Ser Ser Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Tyr Asp Ser Tyr Tyr Lys Tyr Gly Met Asp Val Trp
            100                 105                 110

Gly Gln Gly Thr Ala Val Ile Val Ser Ser
        115                 120

<210> SEQ ID NO 18
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ser Val Tyr Tyr Cys Gln Gln
                85                  90                  95

Tyr Tyr Ser Thr Pro Phe Thr Phe Gly Pro Gly Thr Lys Val Asp Ile
            100                 105                 110

Lys

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Ser Phe Thr Gly Phe Tyr
1               5

<210> SEQ ID NO 20
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 20

Ile Asn His Arg Gly Asn Thr
1               5

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ser Pro Phe Tyr Asp Phe Trp Ser Gly Ser Asp Tyr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Leu Val His Ser Asp Gly Asn Thr Tyr
1               5                   10

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Ile Ser
1

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Gln Ala Thr Gln Phe Pro Leu Thr
1               5

<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Gln Trp Gly Ala Gly Leu Leu Lys Pro Ser Glu
1               5                   10                  15
```

```
Thr Leu Ser Leu Thr Cys Ala Val Tyr Gly Gly Ser Phe Thr Gly Phe
             20                  25                  30

Tyr Trp Ser Trp Ile Arg Gln Pro Pro Gly Lys Gly Leu Glu Trp Ile
         35                  40                  45

Gly Glu Ile Asn His Arg Gly Asn Thr Asn Tyr Asn Pro Ser Leu Lys
 50                  55                  60

Ser Arg Val Thr Met Ser Val Asp Thr Ser Lys Asn Gln Phe Ser Leu
65                  70                  75                  80

Asn Met Ile Ser Val Thr Ala Ala Asp Thr Ala Met Tyr Phe Cys Ala
                 85                  90                  95

Ser Pro Phe Tyr Asp Phe Trp Ser Gly Ser Asp Tyr Trp Gly Gln Gly
            100                 105                 110

Thr Leu Val Thr Val Ser Ser
            115

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Met Leu Thr Gln Thr Pro Leu Thr Ser Pro Val Thr Leu Gly
1               5                   10                  15

Gln Pro Ala Ser Ile Ser Cys Lys Ser Ser Gln Ser Leu Val His Ser
             20                  25                  30

Asp Gly Asn Thr Tyr Leu Ser Trp Leu Gln Gln Arg Pro Gly Gln Pro
         35                  40                  45

Pro Arg Leu Leu Phe Tyr Lys Ile Ser Asn Arg Phe Ser Gly Val Pro
 50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                 85                  90                  95

Thr Gln Phe Pro Leu Thr Phe Gly Gly Gly Thr Lys Val Glu Ile Lys
            100                 105                 110

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, Ser, Asp, Gln, or Asn
<220> FEATURE:
<221> NAME/KEY: MOD_RES
<222> LOCATION: (5)..(5)
<223> OTHER INFORMATION: Thr or Arg
<220> FEATURE:
<221> NAME/KEY: MOD_RES
<222> LOCATION: (6)..(6)
<223> OTHER INFORMATION: Asn, Thr, Tyr, or His

<400> SEQUENCE: 27

Gly Tyr Xaa Phe Xaa Xaa Tyr Gly Ile Ser
1               5                   10
```

```
<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Thr, Pro, Ser, or Ala
<220> FEATURE:
<221> NAME/KEY: MOD_RES
<222> LOCATION: (8)..(8)
<223> OTHER INFORMATION: Asn, Gly, Val, Lys, or Ala
<220> FEATURE:
<221> NAME/KEY: MOD_RES
<222> LOCATION: (9)..(9)
<223> OTHER INFORMATION: Thr or Lys
<220> FEATURE:
<221> NAME/KEY: MOD_RES
<222> LOCATION: (10)..(10)
<223> OTHER INFORMATION: His or Asn
<220> FEATURE:
<221> NAME/KEY: MOD_RES
<222> LOCATION: (13)..(13)
<223> OTHER INFORMATION: Gln or Arg
<220> FEATURE:
<221> NAME/KEY: MOD_RES
<222> LOCATION: (14)..(14)
<223> OTHER INFORMATION: Lys or Met
<220> FEATURE:
<221> NAME/KEY: MOD_RES
<222> LOCATION: (15)..(15)
<223> OTHER INFORMATION: Leu or His

<400> SEQUENCE: 28

Trp Ile Ser Xaa Tyr Asn Gly Xaa Xaa Xaa Tyr Ala Xaa Xaa Xaa Gln
1               5                   10                  15

Gly

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ser or Ala
<220> FEATURE:
<221> NAME/KEY: MOD_RES
<222> LOCATION: (9)..(9)
<223> OTHER INFORMATION: Tyr or Pro
<220> FEATURE:
<221> NAME/KEY: MOD_RES
<222> LOCATION: (15)..(15)
<223> OTHER INFORMATION: Val, Ala, or Gly

<400> SEQUENCE: 29

Glu Asn Tyr Tyr Gly Ser Gly Xaa Xaa Arg Gly Gly Met Asp Xaa
1               5                   10                  15

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Gly Tyr Asp Phe Thr Tyr Tyr Gly Ile Ser
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Trp Ile Ser Thr Tyr Asn Gly Asn Thr His Tyr Ala Arg Met Leu Gln
1               5                   10                  15

Gly

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Glu Asn Tyr Tyr Gly Ser Gly Ala Tyr Arg Gly Gly Met Asp Val
1               5                   10                  15

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ala Ser Gln Ser Val Ser Ser Tyr Leu Ala
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Ala Ser Asn Arg Ala Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Gln Arg Ser Asn Trp Pro Trp Thr
1               5

<210> SEQ ID NO 36
```

<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Tyr Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Asn Gly Asn Thr His Tyr Ala Arg Met Leu
        50                  55                  60

Gln Gly Arg Val Thr Met Thr Thr Asp Thr Ser Thr Arg Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Asn Tyr Tyr Gly Ser Gly Ala Tyr Arg Gly Gly Met Asp
                100                 105                 110

Val Trp Gly Gln Gly Thr Thr Val Thr Val Ser Ser
            115                 120

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
                100                 105

<210> SEQ ID NO 38
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Tyr Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gly Asn Thr His Tyr Ala Arg Met Leu
    50                  55                  60

Gln Gly Arg Val Thr Met Thr Thr Asp Thr Ser Thr Arg Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Asn Tyr Tyr Gly Ser Gly Ala Tyr Arg Gly Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Ala Ala Gly Ala Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu

Ser Leu Ser Pro Gly
    450

<210> SEQ ID NO 39
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Arg Ser Tyr Tyr Trp Gly
1               5

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 41

Ser Ile Tyr Tyr Asn Gly Arg Thr Tyr Tyr Asn Pro Ser Leu Lys Ser
1               5                   10                  15

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Asp Tyr Gly Asp Tyr Gly Ala Phe Asp Ile
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ala Ser Gln Gly Ile Ser Ser Ala Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Ala Ser Ser Leu Glu Ser
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Gln Phe Asn Ser Tyr Pro Leu Thr
1               5

<210> SEQ ID NO 46
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Arg
                20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Asn Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Tyr Gly Asp Tyr Gly Ala Phe Asp Ile Trp Gly
                100                 105                 110

Gln Gly Thr Met Val Thr Val Ser Ser
        115                 120

<210> SEQ ID NO 47
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
                100                 105

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Ser Asn Met Gly Val Val
1               5

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

His Ile Leu Trp Asp Asp Arg Glu Tyr Ser Asn Pro Ala Leu Lys Ser
1               5                   10                  15

```
<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met Ser Arg Asn Tyr Tyr Gly Ser Ser Tyr Val Met Asp Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Ala Ser Ser Ser Val Asn Tyr Met His
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Thr Ser Asn Leu Ala Ser
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

His Gln Trp Asn Asn Tyr Gly Thr
1               5

<210> SEQ ID NO 54
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Asn Met Gly Val Val Trp Ile Arg Gln Pro Pro Gly Lys Ala Leu Glu
        35                  40                  45

Trp Leu Ala His Ile Leu Trp Asp Asp Arg Glu Tyr Ser Asn Pro Ala
    50                  55                  60
```

-continued

```
Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Met Ser Arg Asn Tyr Tyr Gly Ser Ser Tyr Val Met Asp
            100                 105                 110

Tyr Trp Gly Gln Gly Thr Leu Val Thr Val Ser Ser
            115                 120
```

<210> SEQ ID NO 55
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Asp Ile Gln Leu Thr Gln Ser Pro Ser Phe Leu Ser Ala Ser Val Gly
 1               5                  10                  15

Asp Arg Val Thr Ile Thr Cys Ser Ala Ser Ser Ser Val Asn Tyr Met
             20                  25                  30

His Trp Tyr Gln Gln Lys Pro Gly Lys Ala Pro Lys Leu Leu Ile Tyr
         35                  40                  45

Ser Thr Ser Asn Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Glu
 65                  70                  75                  80

Asp Phe Ala Thr Tyr Tyr Cys His Gln Trp Asn Asn Tyr Gly Thr Phe
                 85                  90                  95

Gly Gln Gly Thr Lys Val Glu Ile Lys Arg
            100                 105
```

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Leu Tyr Gly Met Asn
 1               5
```

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Asn Tyr Gly Met Asn
 1               5
```

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Trp Ile Asn Thr Tyr Thr Gly Glu Pro Thr Tyr Ala Asp Asp Phe Lys
1               5                   10                  15
Gly

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Thr Ala Met Asp Tyr Ala Met Ala Tyr
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Tyr Gly Lys Tyr Gly Asp Tyr Tyr Ala Met Asp Tyr
1               5                   10

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Ser Ser Gln Asn Ile Val His Ser Asp Gly Asn Thr Tyr Leu Glu
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ser Ser Gln Ser Ile Val His Ser Asn Gly Asn Thr Tyr Leu Asp
1               5                   10                  15

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Val Ser Asn Arg Phe Ser
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Phe Gln Gly Ser His Val Pro Leu Thr
1               5

<210> SEQ ID NO 65
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Leu Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Thr Ala Met Asp Tyr Ala Met Ala Tyr Trp Gly Gln Gly
            100                 105                 110

Thr Leu Val Thr Val Ser Ser
        115

<210> SEQ ID NO 66
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Leu Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Thr Ala Met Asp Tyr Ala Met Ala Tyr Trp Gly Gln Gly

```
                  100                 105                 110

Thr Leu Val Thr Val Ser Ser
            115

<210> SEQ ID NO 67
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Gly Lys Tyr Gly Asp Tyr Tyr Ala Met Asp Tyr Trp
            100                 105                 110

Gly Gln Gly Thr Leu Val Thr Val Ser Ser
            115                 120

<210> SEQ ID NO 68
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Tyr Gly Lys Tyr Gly Asp Tyr Tyr Ala Met Asp Tyr Trp
            100                 105                 110

Gly Gln Gly Thr Leu Val Thr Val Ser Ser
            115                 120

<210> SEQ ID NO 69
<211> LENGTH: 113
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 69

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Asn Ile Val His Ser
            20                  25                  30

Asp Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 70
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Asn Ile Val His Ser
            20                  25                  30

Asp Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Val Glu Ile Lys
            100                 105                 110

Arg

<210> SEQ ID NO 71
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Val Val Met Thr Gln Thr Pro Leu Ser Leu Pro Val Thr Pro Gly
1               5                   10                  15

Glu Pro Ala Ser Ile Ser Cys Lys Ser Ser Gln Asn Ile Val His Ser

```
            20                  25                  30

Asp Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 72
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Val Val Met Thr Gln Thr Pro Leu Ser Leu Pro Val Ser Leu Gly
1               5                   10                  15

Asp Gln Ala Ser Ile Ser Cys Lys Ser Ser Gln Asn Ile Val His Ser
            20                  25                  30

Asp Gly Asn Thr Tyr Leu Glu Trp Tyr Leu Gln Lys Pro Gly Gln Ser
            35                  40                  45

Pro Lys Val Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 73
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Asp Trp Phe Gln Gln Arg Pro Gly Gln Ser
            35                  40                  45

Pro Arg Arg Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80
```

-continued

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 74
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Ile Val His Ser
            20                  25                  30

Asn Gly Asn Thr Tyr Leu Asp Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Val Glu Ile Lys
            100                 105                 110

Arg

<210> SEQ ID NO 75
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Val Val Met Thr Gln Thr Pro Leu Ser Leu Pro Val Thr Pro Gly
1               5                  10                  15

Glu Pro Ala Ser Ile Ser Cys Arg Ser Ser Gln Ser Ile Val His Ser
            20                  25                  30

Asn Gly Asn Thr Tyr Leu Asp Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 76
<211> LENGTH: 113

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Val Val Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Gly Asn Thr Tyr Leu Asp Trp Tyr Leu Gln Lys Pro Gly Gln Ser
        35                  40                  45
Pro Lys Val Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Asn Arg Val Glu Ala Glu Asp Leu Gly Val Tyr Phe Cys Phe Gln Gly
                85                  90                  95
Ser His Val Pro Leu Thr Phe Gly Gly Gly Thr Lys Leu Glu Ile Lys
            100                 105                 110
Arg

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Tyr Thr Phe Thr Ser Ser Trp Met His
1               5                   10

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile His Pro Asn Ser Gly Gly Thr
1               5

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Arg Gly Asp Tyr Tyr Gly Tyr Val Ser Trp Phe Ala Tyr
1               5                   10

<210> SEQ ID NO 80
<211> LENGTH: 6
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 80

Gln Asn Ile Asn Val Leu
1               5

<210> SEQ ID NO 81
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Ala Ser
1

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Gln Gly Gln Ser Tyr Pro Tyr Thr
1               5

<210> SEQ ID NO 83
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Gln Gln Pro Gly Ser Val Leu Val Arg Pro Gly Ala
1               5                   10                  15

Ser Val Lys Val Ser Cys Lys Ala Ser Gly Tyr Thr Phe Thr Ser Ser
                20                  25                  30

Trp Met His Trp Ala Lys Gln Arg Pro Gly Gln Gly Leu Glu Trp Ile
            35                  40                  45

Gly Glu Ile His Pro Asn Ser Gly Thr Asn Tyr Asn Glu Lys Phe
        50                  55                  60

Lys Gly Lys Ala Thr Val Asp Thr Ser Ser Thr Ala Tyr Val Asp
65                  70                  75                  80

Leu Ser Ser Leu Thr Ser Glu Asp Ser Ala Val Tyr Tyr Cys Ala Arg
                85                  90                  95

Gly Asp Tyr Tyr Gly Tyr Val Ser Trp Phe Ala Tyr Trp Gly Gln Gly
            100                 105                 110

Thr Leu Val Thr Val Ser Ser
        115

<210> SEQ ID NO 84
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Ile
        35                  40                  45

Gly Glu Ile His Pro Asn Ser Gly Gly Thr Asn Tyr Ala Gln Lys Phe
    50                  55                  60

Gln Gly Arg Ala Thr Leu Thr Val Asp Thr Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
        115                 120

<210> SEQ ID NO 85
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Ile
        35                  40                  45

Gly Glu Ile His Pro Asn Ser Gly Gly Thr Asn Tyr Ala Gln Lys Phe
    50                  55                  60

Gln Gly Arg Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
        115                 120

<210> SEQ ID NO 86
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Ile
            35                  40                  45

Gly Glu Ile His Pro Asn Ser Gly Gly Thr Asn Tyr Ala Gln Lys Phe
 50                  55                  60

Gln Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
             85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
            115                 120

<210> SEQ ID NO 87
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Met
            35                  40                  45

Gly Glu Ile His Pro Asn Ser Gly Gly Thr Asn Tyr Ala Gln Lys Phe
 50                  55                  60

Gln Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
             85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
            115                 120

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Leu
            20                  25                  30

Leu Ser Trp Tyr Gln Gln Lys Pro Gly Asn Ile Pro Lys Leu Leu Ile
            35                  40                  45

Tyr Lys Ala Ser Asn Leu His Thr Gly Val Pro Ser Arg Phe Ser Gly
 50                  55                  60

Ser Gly Ser Gly Thr Gly Phe Thr Phe Thr Ile Ser Ser Leu Gln Pro
65                  70                  75                  80

-continued

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Tyr
                85                  90                  95

Thr Phe Gly Gln Gly Thr Lys Leu Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Asn Val Leu
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gln Gly Thr Lys Leu Glu Ile Lys
            100                 105

<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 91

Asp Ile Gln Met Asn Gln Ser Pro Ser Ser Leu Ser Ala Ser Val Gly
1               5                   10                  15

Asp Arg Val Thr Ile Thr Cys Gln Ala Ser Gln Asn Ile Asn Val Leu
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gln Gly Thr Lys Leu Glu Ile Lys
            100                 105

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Tyr Thr Phe Thr Ser Tyr Asp Ile Asn
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asn or Tyr

<400> SEQUENCE: 93

Trp Leu Asn Pro Asn Ser Gly Xaa Thr Gly
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Glu Val Pro Glu Thr Ala Ala Phe Glu Tyr
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (10)..(10)
<223> OTHER INFORMATION: Gly or Ala
<220> FEATURE:
<221> NAME/KEY: MOD_RES
<222> LOCATION: (11)..(11)
<223> OTHER INFORMATION: Leu, Ser, or Gln
<220> FEATURE:
<221> NAME/KEY: MOD_RES
<222> LOCATION: (14)..(14)
<223> OTHER INFORMATION: His or Leu

<400> SEQUENCE: 95

Thr Ser Ser Ser Ser Asp Ile Gly Ala Xaa Xaa Gly Val Xaa
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Tyr Tyr Asn Arg Pro Ser
1               5

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Trp, or Phe

<400> SEQUENCE: 97

Gln Ser Xaa Asp Gly Thr Leu Ser Ala Leu
1               5                   10

<210> SEQ ID NO 98
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110
```

Thr Leu Val Thr Val Ser Ser
        115

<210> SEQ ID NO 99
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(33)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (93)..(93)
<223> OTHER INFORMATION: Any amino acid

<400> SEQUENCE: 99

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Xaa
            20                  25                  30

Xaa Gly Val Xaa Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Xaa Asp Gly Thr
                85                  90                  95

Leu Ser Ala Leu Phe Gly Gly Gly Thr Lys Leu Thr Val Leu Gly
            100                 105                 110

<210> SEQ ID NO 100
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

```
Thr Leu Val Thr Val Ser Ser
        115

<210> SEQ ID NO 101
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
            100                 105                 110

<210> SEQ ID NO 102
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Tyr Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115

<210> SEQ ID NO 103
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 103

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110

<210> SEQ ID NO 104
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115

<210> SEQ ID NO 105
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Ala
            20                  25                  30

Leu Gly Val His Trp Tyr Gln Gln Leu Pro Gly Thr Ala Pro Lys Leu
        35                  40                  45

```
Leu Ile Glu Gly Tyr Tyr Asn Arg Pro Ser Gly Val Pro Asp Arg Phe
 50                  55                  60

Ser Gly Ser Lys Ser Gly Thr Ser Ala Ser Leu Thr Ile Thr Gly Leu
 65                  70                  75                  80

Leu Pro Glu Asp Glu Gly Asp Tyr Tyr Cys Gln Ser Trp Asp Gly Thr
                 85                  90                  95

Leu Ser Ala Leu Phe Gly Gly Gly Thr Lys Leu Thr Val Leu Gly
            100                 105                 110

<210> SEQ ID NO 106
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Met
             35                  40                  45

Gly Trp Leu Asn Pro Asn Ser Gly Asn Thr Gly Tyr Ala Gln Lys Phe
 50                  55                  60

Gln Gly Arg Val Thr Met Thr Ala Asp Arg Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Val Pro Glu Thr Ala Ala Phe Glu Tyr Trp Gly Gln Gly
            100                 105                 110

Thr Leu Val Thr Val Ser Ser
        115

<210> SEQ ID NO 107
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Ser Val Leu Thr Gln Pro Pro Ser Val Ser Gly Ala Pro Gly Gln
 1               5                  10                  15

Arg Val Thr Ile Ser Cys Thr Ser Ser Ser Asp Ile Gly Ala Gly
                20                  25                  30

Ser Gly Val His Trp Tyr Gln Gln Leu Pro Gly Thr Ala Pro Lys Leu
             35                  40                  45

Leu Ile Glu Gly Tyr Tyr Asn Arg Pro Ser Gly Val Pro Asp Arg Phe
 50                  55                  60

Ser Gly Ser Lys Ser Gly Thr Ser Ala Ser Leu Thr Ile Thr Gly Leu
 65                  70                  75                  80

Leu Pro Glu Asp Glu Gly Asp Tyr Tyr Cys Gln Ser Trp Asp Gly Thr
                 85                  90                  95

Leu Ser Ala Leu Phe Gly Gly Gly Thr Lys Leu Thr Val Leu Gly
            100                 105                 110
```

```
<210> SEQ ID NO 108
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115

<210> SEQ ID NO 109
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly
            20                  25                  30

Gln Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
            100                 105                 110

<210> SEQ ID NO 110
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Val Gln Ser Gly Ala Glu Val Lys Lys Pro Gly Ala
```

```
                1               5                    10                   15
Ser Val Lys Val Ser Cys Lys Ala Ser Gly Tyr Thr Phe Thr Ser Tyr
                        20                  25                  30

Asp Ile Asn Trp Val Arg Gln Ala Pro Gly Gln Gly Leu Glu Trp Met
            35                  40                  45

Gly Trp Leu Asn Pro Asn Ser Gly Asn Thr Gly Tyr Ala Gln Lys Phe
        50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
                    100                 105                 110

Thr Leu Val Thr Val Ser Ser
            115
```

<210> SEQ ID NO 111
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly Gly
                20                  25                  30

Leu Gly Val Leu Trp Tyr Gln Gln Leu Pro Gly Thr Ala Pro Lys Leu
            35                  40                  45

Leu Ile Glu Gly Tyr Tyr Asn Arg Pro Ser Gly Val Pro Asp Arg Phe
        50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
                    100                 105                 110
```

<210> SEQ ID NO 112
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Met
            35                  40                  45

Gly Trp Leu Asn Pro Asn Ser Gly Tyr Thr Gly Tyr Ala Gln Lys Phe
        50                  55                  60

Gln Gly Arg Val Thr Met Thr Ala Asp Arg Ser Thr Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Arg Glu Val Pro Glu Thr Ala Ala Phe Glu Tyr Trp Gly Gln Gly
                100                 105                 110

Thr Leu Val Thr Val Ser Ser
        115

<210> SEQ ID NO 113
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly
                20                  25                  30

Leu Gly Val His Trp Tyr Gln Gln Leu Pro Gly Thr Ala Pro Lys Leu
            35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
                100                 105                 110

<210> SEQ ID NO 114
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Met
            35                  40                  45

Gly Trp Leu Asn Pro Asn Ser Gly Tyr Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
                100                 105                 110

Thr Leu Val Thr Val Ser Ser
        115
```

<210> SEQ ID NO 115
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly
            20                  25                  30

Ser Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
            100                 105                 110

<210> SEQ ID NO 116
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Tyr Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115

<210> SEQ ID NO 117
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Ser Val Leu Thr Gln Pro Pro Ser Val Ser Gly Ala Pro Gly Gln
1               5                   10                  15

```
Arg Val Thr Ile Ser Cys Thr Ser Ser Ser Asp Ile Gly Ala Gly
            20                  25                  30

Gln Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
 50                  55                  60

Ser Gly Ser Lys Ser Gly Thr Ser Ala Ser Leu Thr Ile Thr Gly Leu
 65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
            100                 105                 110

<210> SEQ ID NO 118
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Tyr Thr Gly Tyr Ala Gln Lys Phe
 50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115

<210> SEQ ID NO 119
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly
            20                  25                  30

Leu Gly Val Leu Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
 50                  55                  60

Ser Gly Ser Lys Ser Gly Thr Ser Ala Ser Leu Thr Ile Thr Gly Leu
65                  70                  75                  80
```

```
Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
            100                 105                 110

<210> SEQ ID NO 120
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Met
            35                  40                  45

Gly Trp Leu Asn Pro Asn Ser Gly Tyr Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115

<210> SEQ ID NO 121
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
                20                  25                  30

Leu Gly Val His Trp Tyr Gln Gln Leu Pro Gly Thr Ala Pro Lys Leu
            35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Phe Asp Gly Thr
                85                  90                  95

Leu Ser Ala Leu Phe Gly Gly Gly Thr Lys Leu Thr Val Leu Gly
            100                 105                 110

<210> SEQ ID NO 122
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 122

Ser Tyr Phe Trp Ser
1               5

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Tyr Ile Tyr Tyr Ser Gly Asn Thr Lys Tyr Asn Pro Ser Leu Lys Ser
1               5                   10                  15

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Glu Thr Gly Ser Tyr Tyr Gly Phe Asp Tyr
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Ala Ser Gln Ser Ile Asn Asn Tyr Leu Asn
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Ala Ser Ser Leu Gln Ser
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Gln Ser Tyr Ser Thr Pro Arg Thr
1               5
```

<210> SEQ ID NO 128
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Phe Trp Ser Trp Ile Arg Gln Pro Pro Gly Lys Gly Leu Glu Trp Ile
        35                  40                  45

Gly Tyr Ile Tyr Tyr Ser Gly Asn Thr Lys Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Thr Gly Ser Tyr Tyr Gly Phe Asp Tyr Trp Gly Gln Gly Thr
            100                 105                 110

Leu Val Thr Val Ser Ser
        115

<210> SEQ ID NO 129
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Arg Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Gly Asp Phe Ala Thr Tyr Tyr Cys Gln Gln Ser Tyr Ser Thr Pro Arg
                85                  90                  95

Thr Phe Gly Gln Gly Thr Lys Leu Glu Ile Lys
            100                 105

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Tyr Tyr Trp Asn

```
<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Ile Asn His Ala Gly Asn Thr Asn Tyr Asn Pro Ser Leu Lys Ser
1               5                   10                  15

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Tyr Cys Arg Ser Thr Thr Cys Tyr Phe Asp Tyr
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Arg Ala Ser Gln Ser Val Arg Ser Ser Tyr Leu Ala
1               5                   10

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Ala Ser Ser Arg Ala Thr
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Gln Tyr Gly Ser Ser Pro Thr
1               5

<210> SEQ ID NO 136
<211> LENGTH: 120
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 136

```
Gln Val Gln Leu Gln Gln Trp Gly Ala Gly Leu Leu Lys Pro Ser Glu
  1               5                  10                  15
Thr Leu Ser Leu Thr Cys Ala Val His Gly Gly Ser Phe Ser Gly Tyr
             20                  25                  30
Tyr Trp Asn Trp Ile Arg Gln Pro Pro Gly Lys Gly Leu Glu Trp Ile
         35                  40                  45
Gly Glu Ile Asn His Ala Gly Asn Thr Asn Tyr Asn Pro Ser Leu Lys
     50                  55                  60
Ser Arg Val Thr Ile Ser Leu Asp Thr Ser Lys Asn Gln Phe Ser Leu
 65                  70                  75                  80
Thr Leu Thr Ser Val Thr Ala Ala Asp Thr Ala Val Tyr Tyr Cys Ala
                 85                  90                  95
Arg Gly Tyr Cys Arg Ser Thr Thr Cys Tyr Phe Asp Tyr Trp Gly Gln
            100                 105                 110
Gly Thr Leu Val Thr Val Ser Ser
            115                 120
```

<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

```
Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Arg Ser Ser
             20                  25                  30
Tyr Leu Ala Trp Tyr Gln Gln Lys Pro Gly Gln Ala Pro Arg Leu Leu
         35                  40                  45
Ile Tyr Gly Ala Ser Ser Arg Ala Thr Gly Ile Pro Asp Arg Phe Ser
     50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Thr Phe Gly Gln Gly Thr Arg Leu Glu Ile Lys
            100                 105
```

<210> SEQ ID NO 138
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Glu Val Gln Leu Gln Gln Ser Gly Ala Glu Leu Val Lys Pro Gly Ala
  1               5                  10                  15
Ser Val Lys Leu Ser Cys Thr Ala Ser Gly Phe Asp Ile Gln Asp Thr
             20                  25                  30
Tyr Met His Trp Val Lys Gln Arg Pro Glu Gln Gly Leu Glu Trp Ile
         35                  40                  45
```

```
Gly Arg Ile Asp Pro Ala Ser Gly His Thr Lys Tyr Asp Pro Lys Phe
            50                  55                  60

Gln Val Lys Ala Thr Ile Thr Thr Asp Thr Ser Asn Thr Ala Tyr
 65                  70                  75                  80

Leu Gln Leu Ser Ser Leu Thr Glu Asp Thr Ala Val Tyr Tyr Cys
                85                  90                  95

Ser Arg Ser Gly Gly Leu Pro Asp Val Trp Gly Ala Gly Thr Thr Val
                100                 105                 110

Thr Val Ser Ser
        115
```

<210> SEQ ID NO 139
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Met
                20                  25                  30

Tyr Trp Tyr Gln Gln Lys Pro Gly Ser Ser Pro Lys Pro Trp Ile Tyr
                35                  40                  45

Ala Thr Ser Asn Leu Ala Ser Gly Val Pro Asp Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Gly Asn Pro Arg Thr
                85                  90                  95

Phe Gly Gly Gly Thr Lys Leu Glu Ile Lys
                100                 105
```

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
Gly Phe Asp Ile Gln Asp Thr Tyr Met His
 1               5                  10
```

<210> SEQ ID NO 141
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

```
Arg Ile Asp Pro Ala Ser Gly His Thr Lys Tyr Asp Pro Lys Phe Gln
 1               5                  10                  15

Val
```

```
<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ser Gly Gly Leu Pro Asp Val
1               5

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Arg Ala Ser Ser Ser Val Ser Tyr Met Tyr
1               5                   10

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Thr Ser Asn Leu Ala Ser
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Gln Trp Ser Gly Asn Pro Arg Thr
1               5

<210> SEQ ID NO 146
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Val Gln Ser Gly Ala Glu Val Lys Lys Pro Gly Ala
1               5                   10                  15

Ser Val Lys Leu Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Thr Asp Thr Ser Thr Ser Thr Val Tyr
```

```
                 65                  70                  75                  80
Met Glu Leu Ser Ser Leu Arg Ser Glu Asp Thr Ala Val Tyr Tyr Cys
                 85                  90                  95

Ser Arg Ser Gly Gly Leu Pro Asp Val Trp Gly Gln Gly Thr Thr Val
                100                 105                 110

Thr Val Ser Ser
        115

<210> SEQ ID NO 147
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Ile Val Leu Thr Gln Ser Pro Gly Thr Leu Ser Leu Ser Pro Gly
1               5                   10                  15

Glu Arg Val Thr Met Ser Cys Arg Ala Ser Ser Ser Val Ser Tyr Met
                20                  25                  30

Tyr Trp Tyr Gln Gln Lys Pro Gly Gln Ala Pro Arg Pro Trp Ile Tyr
            35                  40                  45

Ala Thr Ser Asn Leu Ala Ser Gly Val Pro Asp Arg Phe Ser Gly Ser
        50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
                100                 105

<210> SEQ ID NO 148
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gln Val Gln Leu Val Gln Ser Gly Ala Glu Val Lys Lys Pro Gly Ala
1               5                   10                  15

Ser Val Lys Leu Ser Cys Lys Ala Ser Gly Phe Asp Ile Gln Asp Thr
                20                  25                  30

Tyr Met His Trp Val Arg Gln Ala Pro Gly Gln Gly Leu Glu Trp Met
            35                  40                  45

Gly Arg Ile Asp Pro Ala Ser Gly His Thr Lys Tyr Asp Pro Lys Phe
        50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Ser Gly Gly Leu Pro Asp Val Trp Gly Gln Gly Thr Thr Val
                100                 105                 110

Thr Val Ser Ser
        115
```

```
<210> SEQ ID NO 149
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 150
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 151
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
            35                  40                  45

Ala Thr Ser Asn Leu Ala Ser Gly Val Pro Asp Arg Phe Ser Gly Ser
 50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 152
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Asn Tyr
            20                  25                  30

Ala Met Ser Trp Val Arg Gln Thr Pro Glu Lys Arg Leu Glu Trp Val
        35                  40                  45

Ala Thr Ile Thr Ser Gly Gly Ser Tyr Ile Tyr Tyr Leu Asp Ser Val
    50                  55                  60

Lys Gly Arg Phe Thr Ile Ser Arg Asp Asn Ala Lys Ser Thr Leu Tyr
65                  70                  75                  80

Leu Gln Met Ser Ser Leu Arg Ser Glu Asp Thr Ala Ile Tyr Asn Cys
                85                  90                  95

Ala Arg Arg Lys Asp Gly Asn Tyr Tyr Tyr Ala Met Asp Tyr Trp Gly
            100                 105                 110

Gln Gly Thr Ser Val Thr Val Ser Ser
        115                 120

<210> SEQ ID NO 153
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Asn Tyr
            20                  25                  30

Ala Met Ser Trp Val Arg Gln Thr Pro Glu Lys Arg Leu Glu Trp Val
        35                  40                  45

Ala Thr Ile Thr Ser Gly Gly Ser Tyr Ile Tyr Tyr Leu Asp Ser Val
    50                  55                  60

Lys Gly Arg Phe Thr Ile Ser Arg Asp Asn Ala Lys Ser Thr Leu Tyr
65                  70                  75                  80

Leu Gln Met Ser Ser Leu Arg Ser Glu Asp Thr Ala Ile Tyr Tyr Cys
                85                  90                  95

Ala Arg Arg Lys Asp Gly Asn Tyr Tyr Tyr Ala Met Asp Tyr Trp Gly
            100                 105                 110

Gln Gly Thr Ser Val Thr Val Ser Ser
        115                 120

<210> SEQ ID NO 154
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Gln Arg Leu Glu Trp Val
        35                  40                  45

Ser Thr Ile Thr Ser Gly Gly Ser Tyr Ile Tyr Tyr Leu Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ala Glu Asp Thr Ala Val Tyr Asn Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120

<210> SEQ ID NO 155
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Gln Arg Leu Glu Trp Val
        35                  40                  45

Ser Thr Ile Thr Ser Gly Gly Ser Tyr Ile Tyr Tyr Leu Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120

<210> SEQ ID NO 156
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 156

```
Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Gln Arg Leu Glu Trp Leu
        35                  40                  45

Ala Thr Ile Thr Ser Gly Gly Ser Tyr Ile Tyr Tyr Leu Asp Ser Val
    50                  55                  60

Lys Gly Arg Phe Thr Ile Ser Arg Asp Asn Ser Lys Ser Thr Leu Tyr
65                  70                  75                  80

Leu Gln Met Gly Ser Leu Arg Ala Glu Asp Met Ala Val Tyr Asn Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120
```

<210> SEQ ID NO 157
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 157

```
Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Gln Arg Leu Glu Trp Leu
        35                  40                  45

Ala Thr Ile Thr Ser Gly Gly Ser Tyr Ile Tyr Tyr Leu Asp Ser Val
    50                  55                  60

Lys Gly Arg Phe Thr Ile Ser Arg Asp Asn Ser Lys Ser Thr Leu Tyr
65                  70                  75                  80

Leu Gln Met Gly Ser Leu Arg Ala Glu Asp Met Ala Val Tyr Tyr Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120
```

<210> SEQ ID NO 158
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 158

| Gln | Val | Gln | Leu | Val | Glu | Ser | Gly | Gly | Gly | Leu | Ile | Gln | Pro | Gly | Gly |
|---|---|---|---|---|---|---|---|---|---|---|---|---|---|---|---|
| 1 | | | | 5 | | | | | 10 | | | | | 15 | |

Ser Leu Arg Leu Ser Cys Ala Ala Ser Gly Phe Thr Phe Thr Asn Tyr
            20                25               30

Ala Met Ser Trp Val Arg Gln Ala Arg Gly Gln Arg Leu Glu Trp Val
        35                40              45

Ser Thr Ile Thr Ser Gly Gly Ser Tyr Ile Tyr Tyr Leu Asp Ser Val
 50                  55                60

Lys Gly Arg Phe Thr Ile Ser Arg Asp Asn Ser Lys Ser Thr Leu Tyr
65               70              75              80

Met Glu Leu Ser Ser Leu Arg Ser Glu Asp Thr Ala Val Tyr Asn Cys
            85              90              95

Ala Arg Arg Lys Asp Gly Asn Tyr Tyr Tyr Ala Met Asp Tyr Trp Gly
           100            105           110

Gln Gly Thr Thr Val Thr Val Ser Ser
      115           120

<210> SEQ ID NO 159
<211> LENGTH: 121
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 159

Gln Val Gln Leu Val Glu Ser Gly Gly Gly Leu Ile Gln Pro Gly Gly
1               5               10              15

Ser Leu Arg Leu Ser Cys Ala Ala Ser Gly Phe Thr Phe Thr Asn Tyr
            20                25               30

Ala Met Ser Trp Val Arg Gln Ala Arg Gly Gln Arg Leu Glu Trp Val
        35                40              45

Ser Thr Ile Thr Ser Gly Gly Ser Tyr Ile Tyr Tyr Leu Asp Ser Val
 50                  55                60

Lys Gly Arg Phe Thr Ile Ser Arg Asp Asn Ser Lys Ser Thr Leu Tyr
65               70              75              80

Met Glu Leu Ser Ser Leu Arg Ser Glu Asp Thr Ala Val Tyr Tyr Cys
            85              90              95

Ala Arg Arg Lys Asp Gly Asn Tyr Tyr Tyr Ala Met Asp Tyr Trp Gly
           100            105           110

Gln Gly Thr Thr Val Thr Val Ser Ser
      115           120

<210> SEQ ID NO 160
<211> LENGTH: 121
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 160

Gln Val Gln Leu Val Gln Ser Gly Ser Glu Leu Lys Lys Pro Gly Ala
1               5               10              15

Ser Val Lys Val Ser Cys Lys Ala Ser Gly Phe Thr Phe Thr Asn Tyr
            20                25               30

Ala Met Ser Trp Val Arg Gln Ala Pro Gly Lys Arg Leu Glu Trp Val
            35                  40                  45

Ser Thr Ile Thr Ser Gly Gly Ser Tyr Ile Tyr Tyr Leu Asp Ser Val
 50                  55                  60

Lys Gly Arg Phe Thr Ile Ser Arg Glu Asn Ala Lys Ser Thr Leu Tyr
 65                  70                  75                  80

Leu Gln Met Asn Ser Leu Arg Thr Glu Asp Thr Ala Leu Tyr Asn Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120

<210> SEQ ID NO 161
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Val Gln Ser Gly Ser Glu Leu Lys Lys Pro Gly Ala
 1               5                  10                  15

Ser Val Lys Val Ser Cys Lys Ala Ser Gly Phe Thr Phe Thr Asn Tyr
            20                  25                  30

Ala Met Ser Trp Val Arg Gln Ala Pro Gly Lys Arg Leu Glu Trp Val
            35                  40                  45

Ala Thr Ile Thr Ser Gly Gly Ser Tyr Ile Tyr Tyr Leu Asp Ser Val
 50                  55                  60

Lys Gly Arg Phe Thr Ile Ser Arg Glu Asn Ala Lys Ser Thr Leu Tyr
 65                  70                  75                  80

Leu Gln Met Asn Ser Leu Arg Thr Glu Asp Thr Ala Leu Tyr Tyr Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120

<210> SEQ ID NO 162
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Val Gln Leu Leu Gln Ser Gly Ala Glu Val Lys Lys Pro Gly Ala
 1               5                  10                  15

Ser Val Lys Val Ser Cys Lys Ala Ser Gly Phe Thr Phe Thr Asn Tyr
            20                  25                  30

Ala Met Ser Trp Val Arg Gln Ala Pro Gly Gln Arg Leu Glu Trp Val
            35                  40                  45

Ala Thr Ile Thr Ser Gly Gly Ser Tyr Ile Tyr Tyr Leu Asp Ser Val
 50                  55                  60

Lys Gly Arg Phe Thr Ile Ser Arg Asp Asn Ala Lys Ser Thr Leu His
 65                  70                  75                  80

```
Leu Gln Met Asn Ser Leu Arg Ala Glu Asp Thr Ala Val Tyr Asn Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120

<210> SEQ ID NO 163
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Leu Gln Ser Gly Ala Glu Val Lys Lys Pro Gly Ala
1               5                   10                  15

Ser Val Lys Val Ser Cys Lys Ala Ser Gly Phe Thr Phe Thr Asn Tyr
            20                  25                  30

Ala Met Ser Trp Val Arg Gln Ala Pro Gly Gln Arg Leu Glu Trp Val
        35                  40                  45

Ala Thr Ile Thr Ser Gly Gly Ser Tyr Ile Tyr Tyr Leu Asp Ser Val
    50                  55                  60

Lys Gly Arg Phe Thr Ile Ser Arg Asp Asn Ala Lys Ser Thr Leu His
65                  70                  75                  80

Leu Gln Met Asn Ser Leu Arg Ala Glu Asp Thr Ala Ile Tyr Tyr Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120

<210> SEQ ID NO 164
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Val Met Leu Leu Gln Ser Gly Ala Glu Val Lys Lys Pro Gly Ala
1               5                   10                  15

Ser Val Lys Val Ser Cys Lys Ala Ser Gly Phe Thr Phe Thr Asn Tyr
            20                  25                  30

Ala Met Ser Trp Val Arg Gln Ala Pro Gly Gln Arg Leu Glu Trp Val
        35                  40                  45

Ala Thr Ile Thr Ser Gly Gly Ser Tyr Ile Tyr Tyr Leu Asp Ser Val
    50                  55                  60

Lys Gly Arg Phe Thr Ile Ser Arg Asp Asn Ala Lys Ser Thr Leu His
65                  70                  75                  80

Leu Gln Met Asn Ser Leu Arg Ala Glu Asp Thr Ala Val Tyr Tyr Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120
```

-continued

```
<210> SEQ ID NO 165
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Ile His Trp Tyr Gln Gln Lys Ala Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Tyr
                85                  90                  95

Glu Asp Pro Trp Thr Phe Gly Gly Gly Thr Lys Leu Glu Ile Lys
            100                 105                 110

<210> SEQ ID NO 166
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (108)..(108)
<223> OTHER INFORMATION: Any amino acid

<400> SEQUENCE: 166

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Ser Tyr
            20                  25                  30

Gly Asn Ser Phe Ile His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Tyr
                85                  90                  95

Glu Asp Pro Trp Thr Phe Gly Gly Gly Thr Lys Xaa Glu Ile Lys
            100                 105                 110

<210> SEQ ID NO 167
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (108)..(108)
```

<223> OTHER INFORMATION: Any amino acid

<400> SEQUENCE: 167

| Asp | Ile | Val | Leu | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Glu | Ser | Val | Asp | Ser | Tyr |
|---|---|---|---|---|---|---|---|---|---|---|---|---|---|---|---|
| | | | 20 | | | | | 25 | | | | | 30 | | |

| Gly | Asn | Ser | Phe | Ile | His | Trp | Tyr | Gln | Gln | Lys | Pro | Gly | Gln | Pro | Pro |
|---|---|---|---|---|---|---|---|---|---|---|---|---|---|---|---|
| | | 35 | | | | | 40 | | | | | 45 | | | |

| Lys | Leu | Leu | Ile | Tyr | Arg | Ala | Ser | Asn | Leu | Glu | Ser | Gly | Ile | Pro | Ala |
|---|---|---|---|---|---|---|---|---|---|---|---|---|---|---|---|
| | 50 | | | | | 55 | | | | | 60 | | | | |

| Arg | Phe | Ser | Gly | Ser | Gly | Ser | Arg | Thr | Asp | Phe | Thr | Leu | Thr | Ile | Ser |
|---|---|---|---|---|---|---|---|---|---|---|---|---|---|---|---|
| 65 | | | | | 70 | | | | | 75 | | | | | 80 |

| Ser | Leu | Gln | Pro | Glu | Asp | Phe | Ala | Thr | Tyr | Tyr | Cys | Gln | Gln | Ser | Tyr |
|---|---|---|---|---|---|---|---|---|---|---|---|---|---|---|---|
| | | | | 85 | | | | | 90 | | | | | 95 | |

| Glu | Asp | Pro | Trp | Thr | Phe | Gly | Gly | Gly | Thr | Lys | Xaa | Glu | Ile | Lys | |
|---|---|---|---|---|---|---|---|---|---|---|---|---|---|---|---|
| | | | 100 | | | | | 105 | | | | | 110 | | |

<210> SEQ ID NO 168
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (108)..(108)
<223> OTHER INFORMATION: Any amino acid

<400> SEQUENCE: 168

| Asp | Ile | Val | Leu | Thr | Gln | Ser | Pro | Asp | Phe | Gln | Ser | Val | Thr | Pro | Lys |
|---|---|---|---|---|---|---|---|---|---|---|---|---|---|---|---|
| 1 | | | | 5 | | | | | 10 | | | | | 15 | |

| Glu | Lys | Val | Thr | Ile | Thr | Cys | Arg | Ala | Ser | Glu | Ser | Val | Asp | Ser | Tyr |
|---|---|---|---|---|---|---|---|---|---|---|---|---|---|---|---|
| | | | 20 | | | | | 25 | | | | | 30 | | |

| Gly | Asn | Ser | Phe | Ile | His | Trp | Tyr | Gln | Gln | Lys | Pro | Gly | Gln | Pro | Pro |
|---|---|---|---|---|---|---|---|---|---|---|---|---|---|---|---|
| | | 35 | | | | | 40 | | | | | 45 | | | |

| Lys | Leu | Leu | Ile | Tyr | Arg | Ala | Ser | Asn | Leu | Glu | Ser | Gly | Ile | Pro | Ala |
|---|---|---|---|---|---|---|---|---|---|---|---|---|---|---|---|
| | 50 | | | | | 55 | | | | | 60 | | | | |

| Arg | Phe | Ser | Gly | Ser | Gly | Ser | Arg | Thr | Asp | Phe | Thr | Leu | Thr | Ile | Ser |
|---|---|---|---|---|---|---|---|---|---|---|---|---|---|---|---|
| 65 | | | | | 70 | | | | | 75 | | | | | 80 |

| Ser | Leu | Glu | Ala | Glu | Asp | Ala | Ala | Thr | Tyr | Tyr | Cys | Gln | Gln | Ser | Tyr |
|---|---|---|---|---|---|---|---|---|---|---|---|---|---|---|---|
| | | | | 85 | | | | | 90 | | | | | 95 | |

| Glu | Asp | Pro | Trp | Thr | Phe | Gly | Gly | Gly | Thr | Lys | Xaa | Glu | Ile | Lys | |
|---|---|---|---|---|---|---|---|---|---|---|---|---|---|---|---|
| | | | 100 | | | | | 105 | | | | | 110 | | |

<210> SEQ ID NO 169
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (108)..(108)
<223> OTHER INFORMATION: Any amino acid

<400> SEQUENCE: 169

| Asp | Ile | Val | Leu | Thr | Gln | Thr | Pro | Leu | Ser | Leu | Ser | Val | Thr | Pro | Gly |
|---|---|---|---|---|---|---|---|---|---|---|---|---|---|---|---|
| 1 | | | | 5 | | | | | 10 | | | | | 15 | |

```
Gln Pro Ala Ser Ile Ser Cys Arg Ala Ser Glu Ser Val Asp Ser Tyr
                20                  25                  30

Gly Asn Ser Phe Ile His Trp Tyr Gln Gln Lys Pro Gly Gln Pro Pro
         35                  40                  45

Lys Leu Leu Ile Tyr Arg Ala Ser Asn Leu Glu Ser Gly Ile Pro Ala
 50                      55                  60

Arg Phe Ser Gly Ser Gly Ser Arg Thr Asp Phe Thr Leu Lys Ile Ser
 65                  70                  75                  80

Arg Val Glu Ala Glu Asp Val Gly Val Tyr Tyr Cys Gln Gln Ser Tyr
                 85                  90                  95

Glu Asp Pro Trp Thr Phe Gly Gly Gly Thr Lys Xaa Glu Ile Lys
            100                 105                 110
```

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

```
Thr Tyr Gly Met Ser
1               5
```

<210> SEQ ID NO 171
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

```
Trp Met Asn Thr Tyr Ser Gly Val Thr Thr Tyr Ala Asp Asp Phe Lys
1               5                   10                  15

Gly
```

<210> SEQ ID NO 172
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

```
Glu Gly Tyr Val Phe Asp Asp Tyr Tyr Ala Thr Asp Tyr
1               5                   10
```

<210> SEQ ID NO 173
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

```
Arg Ser Ser Gln Asn Ile Val His Ser Asp Gly Asn Thr Tyr Leu Glu
1               5                   10                  15
```

<210> SEQ ID NO 174
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Lys Val Ser Asn Arg Phe Ser
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Phe Gln Gly Ser His Val Pro Leu Thr
1               5

<210> SEQ ID NO 176
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Met Asn Thr Tyr Ser Gly Val Thr Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Met Gln Ile Asp Asn Leu Lys Asn Glu Asp Thr Ala Thr Tyr Phe Cys
                85                  90                  95

Ala Arg Glu Gly Tyr Val Phe Asp Asp Tyr Tyr Ala Thr Asp Tyr Trp
            100                 105                 110

Gly Gln Gly Thr Ser Val Thr Val Ser Ser
        115                 120

<210> SEQ ID NO 177
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45
```

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Leu Thr Phe Gly Ala Gly Thr Lys Leu Glu Leu Lys
            100                 105                 110
```

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

```
Lys Tyr Asp Ile Asn
1               5
```

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

```
Trp Ile Phe Pro Gly Asp Gly Arg Thr Asp Tyr Asn Glu Lys Phe Lys
1               5                   10                  15

Gly
```

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

```
Tyr Gly Pro Ala Met Asp Tyr
1               5
```

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

```
Arg Ser Ser Gln Thr Ile Val His Ser Asn Gly Asp Thr Tyr Leu Asp
1               5                   10                  15
```

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Lys Val Ser Asn Arg Phe Ser
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Phe Gln Gly Ser His Val Pro Tyr Thr
1               5

<210> SEQ ID NO 184
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Met Gly Trp Ser Trp Val Phe Leu Phe Leu Leu Ser Val Thr Ala Gly
1               5                   10                  15

Val His Ser Gln Val His Leu Gln Gln Ser Gly Pro Glu Leu Val Lys
            20                  25                  30

Pro Gly Ala Ser Val Lys Leu Ser Cys Lys Ala Ser Gly Tyr Thr Phe
        35                  40                  45

Thr Lys Tyr Asp Ile Asn Trp Val Arg Gln Arg Pro Glu Gln Gly Leu
    50                  55                  60

Glu Trp Ile Gly Trp Ile Phe Pro Gly Asp Gly Arg Thr Asp Tyr Asn
65                  70                  75                  80

Glu Lys Phe Lys Gly Lys Ala Thr Leu Thr Thr Asp Lys Ser Ser Ser
                85                  90                  95

Thr Ala Tyr Met Glu Val Ser Arg Leu Thr Ser Glu Asp Ser Ala Val
            100                 105                 110

Tyr Phe Cys Ala Arg Tyr Gly Pro Ala Met Asp Tyr Trp Gly Gln Gly
        115                 120                 125

Thr Ser Val Thr Val Ala Ser
    130                 135

<210> SEQ ID NO 185
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Thr Ile
        35                  40                  45

Val His Ser Asn Gly Asp Thr Tyr Leu Asp Trp Phe Leu Gln Lys Pro

```
                50                  55                  60
Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                     85                  90                  95

Leu Lys Ile Ser Arg Val Glu Ala Glu Asp Leu Gly Val Tyr Tyr Cys
                100                 105                 110

Phe Gln Gly Ser His Val Pro Tyr Thr Phe Gly Gly Gly Thr Lys Leu
                115                 120                 125

Glu Ile Lys
   130

<210> SEQ ID NO 186
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser Tyr Ile Trp Ser
 1               5

<210> SEQ ID NO 187
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Arg Ile Tyr Ala Ser Gly Asn Thr Asn Tyr Asn Pro Ser Leu Lys Ser
 1               5                  10                  15

<210> SEQ ID NO 188
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Asp Tyr Arg Val Ala Gly Thr Tyr Tyr Tyr Tyr Tyr Gly Leu Asp Val
 1               5                  10                  15

<210> SEQ ID NO 189
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Thr Gly Thr Ser Ser Asp Val Gly Val Tyr Asp Tyr Val Ser
 1               5                  10

<210> SEQ ID NO 190
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 190

Glu Val Ser Asn Arg Pro Ser
1               5

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Ser Tyr Thr Ser Arg Ser Thr Trp Val
1               5                   10

<210> SEQ ID NO 192
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Tyr Tyr Trp Thr
1               5

<210> SEQ ID NO 193
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Arg Ile Tyr Thr Ser Gly Ile Thr Asn Tyr Asn Pro Ser Leu Lys Ser
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Glu Arg Val Val Gly Ala Ser Arg Tyr Tyr Tyr Tyr Gly Val Asp Val
1               5                   10                  15

<210> SEQ ID NO 195
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Thr Gly Thr Ser Ser Asp Val Gly Leu Tyr Asn Tyr Val Ser
1               5                   10

```
<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Glu Val Asn Asn Arg Pro Ser
1               5

<210> SEQ ID NO 197
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Ser Tyr Thr Ser Ser Ser Thr Trp Val
1               5                   10

<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Tyr Tyr Trp Thr
1               5

<210> SEQ ID NO 199
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Arg Ile Tyr Thr Ser Gly Ile Thr Asn Tyr Asn Pro Ser Leu Lys Ser
1               5                   10                  15

<210> SEQ ID NO 200
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Glu Arg Val Val Gly Ala Ser Arg Tyr Tyr Tyr Gly Val Asp Val
1               5                   10                  15

<210> SEQ ID NO 201
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201
```

```
Thr Gly Thr Ser Ser Asp Ile Gly Leu Tyr Asp Tyr Val Ser
1               5                   10

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Glu Val Asn Asn Arg Pro Ser
1               5

<210> SEQ ID NO 203
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Ser Tyr Thr Ser Ser Ser Thr Trp Val
1               5                   10

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Tyr Ser Trp Ser
1               5

<210> SEQ ID NO 205
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Arg Thr Ser Thr Ser Gly Arg Asn Asn Tyr Asn Pro Ser Leu Lys Ser
1               5                   10                  15

<210> SEQ ID NO 206
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asp Phe Thr Ile Ala Ala Arg Arg Tyr Tyr Tyr Tyr Gly Met Asp Val
1               5                   10                  15

<210> SEQ ID NO 207
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 207

Thr Gly Thr Ser Ser Asp Ile Gly Leu Tyr Asn Tyr Val Ser
1               5                   10

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Glu Val Ile Asn Arg Pro Ser
1               5

<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Ser Tyr Thr Ser Ser Ser Thr Trp Val
1               5                   10

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Asn Asn Tyr Trp Ser
1               5

<210> SEQ ID NO 211
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Arg Val Tyr Ser Ser Gly Leu Thr Asn Tyr Lys Pro Ser Leu Lys Ser
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Glu Arg Ala Thr Val Thr Thr Arg Tyr His Tyr Asp Gly Met Asp Val
1               5                   10                  15
```

<210> SEQ ID NO 213
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Thr Gly Ser Ser Ser Asp Ile Gly Thr Tyr Asn Tyr Val Ser
1               5                   10

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Glu Val Asn Asn Arg Pro Ser
1               5

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Ser Tyr Ser Ser Ser Ser Thr Trp Val
1               5                   10

<210> SEQ ID NO 216
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Tyr Tyr Trp Ser
1               5

<210> SEQ ID NO 217
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Arg Ile Phe Ala Ser Gly Ser Thr Asn Tyr Asn Pro Ser Leu Arg Ser
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Glu Arg Val Gly Val Gln Asp Tyr Tyr His Tyr Ser Gly Met Asp Val
1               5                   10                  15

<210> SEQ ID NO 219
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Thr Gly Thr Ser Ser Asp Val Gly Leu Tyr Asn Tyr Val Ser
1               5                   10

<210> SEQ ID NO 220
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Glu Val Ser Lys Arg Pro Ser
1               5

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ser Ser Tyr Thr Ser Ser Ser Thr Trp Val
1               5                   10

<210> SEQ ID NO 222
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Ala Gly Lys Gly Leu Glu Trp Ile
        35                  40                  45

Gly Arg Ile Tyr Thr Ser Gly Ile Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Val Val Gly Ala Ser Arg Tyr Tyr Tyr Tyr Gly Val Asp
            100                 105                 110

Val Trp Gly Gln Gly Thr Thr Val Thr Val Ser Ser
            115                 120

<210> SEQ ID NO 223
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Leu Tyr
            20                  25                  30

Asn Tyr Val Ser Trp Tyr Gln Gln His Pro Asp Lys Ala Pro Lys Leu
        35                  40                  45

Met Ile Phe Glu Val Asn Asn Arg Pro Ser Gly Val Ser Asn Arg Phe
    50                  55                  60

Ser Gly Ser Asn Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 224
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Ala Gly Lys Gly Leu Glu Trp Ile
        35                  40                  45

Gly Arg Ile Tyr Thr Ser Gly Ile Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Val Val Gly Ala Ser Arg Tyr Tyr Tyr Tyr Gly Val Asp
            100                 105                 110

Val Trp Gly Gln Gly Thr Thr Val Thr Val Ser Ser
        115                 120

<210> SEQ ID NO 225
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 225

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Leu Tyr
            20                  25                  30

Asp Tyr Val Ser Trp Tyr Gln Gln His Pro Asp Arg Ala Pro Lys Leu
        35                  40                  45

Ile Ile Phe Glu Val Asn Asn Arg Pro Ser Gly Val Ser Tyr Arg Phe
    50                  55                  60

Ser Gly Ser Asn Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 226
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ser Trp Ser Trp Ile Arg Gln Pro Ala Gly Lys Gly Leu Glu Trp Ile
        35                  40                  45

Gly Arg Thr Ser Thr Ser Gly Arg Asn Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Asp Phe Thr Ile Ala Ala Arg Tyr Tyr Tyr Tyr Gly Met Asp
            100                 105                 110

Val Trp Gly Gln Gly Thr Thr Val Thr Val Ser Ser
        115                 120

<210> SEQ ID NO 227
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Leu Tyr
            20                  25                  30

Asn Tyr Val Ser Trp Tyr Gln Gln His Pro Gly Lys Ala Pro Lys Leu
        35                  40                  45

Ile Ile Tyr Glu Val Ile Asn Arg Pro Ser Gly Val Ser Asn Arg Phe
```

```
            50                  55                  60
Ser Gly Ser Glu Ser Gly Asn Thr Ala Ser Leu Thr Ile Ser Gly Leu
 65                  70                  75                  80

Gln Ala Glu Asp Glu Ala Asn Tyr Tyr Cys Ser Ser Tyr Thr Ser Ser
                 85                  90                  95

Ser Thr Trp Val Phe Gly Gly Gly Thr Lys Leu Thr Val Leu
            100                 105                 110

<210> SEQ ID NO 228
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gln Val Gln Leu Gln Glu Ser Gly Pro Arg Leu Val Lys Pro Ser Glu
  1               5                  10                  15

Thr Leu Ser Leu Thr Cys Thr Val Ser Gly Gly Ser Ile Thr Asn Asn
             20                  25                  30

Tyr Trp Ser Trp Ile Arg Gln Pro Ala Gly Lys Gly Leu Glu Trp Ile
         35                  40                  45

Gly Arg Val Tyr Ser Ser Gly Leu Thr Asn Tyr Lys Pro Ser Leu Lys
     50                  55                  60

Ser Arg Val Thr Met Ser Val Asp Thr Ser Lys Asn Gln Phe Ser Leu
 65                  70                  75                  80

Arg Leu Asn Ser Val Thr Ala Ala Asp Thr Ala Val Tyr Tyr Cys Ala
                 85                  90                  95

Arg Glu Arg Ala Thr Val Thr Arg Tyr His Tyr Asp Gly Met Asp
            100                 105                 110

Val Trp Gly Gln Gly Thr Ser Val Thr Val Ser Ser
        115                 120

<210> SEQ ID NO 229
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gln Ser Ala Leu Thr Gln Pro Ala Ser Val Ser Gly Ser Pro Gly Gln
  1               5                  10                  15

Ser Ile Thr Ile Ser Cys Thr Gly Ser Ser Ser Asp Ile Gly Thr Tyr
             20                  25                  30

Asn Tyr Val Ser Trp Tyr Gln Gln Tyr Pro Gly Lys Ala Pro Glu Leu
         35                  40                  45

Met Ile Tyr Glu Val Asn Asn Arg Pro Ser Gly Val Ser Asp Arg Phe
     50                  55                  60

Ser Gly Ser Thr Ser Gly Asn Thr Ala Ser Leu Thr Ile Ser Gly Leu
 65                  70                  75                  80

Gln Ala Asn Asp Glu Ala Asp Tyr Tyr Cys Ser Ser Tyr Ser Ser Ser
                 85                  90                  95

Ser Thr Trp Val Phe Gly Gly Gly Thr Lys Leu Thr Val Leu
            100                 105                 110
```

```
<210> SEQ ID NO 230
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Phe Ala Ser Gly Ser Thr Asn Tyr Asn Pro Ser Leu Arg
    50                  55                  60

Ser Arg Val Thr Met Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Glu Arg Val Gly Val Gln Asp Tyr Tyr His Tyr Ser Gly Met Asp
            100                 105                 110

Val Trp Gly Gln Gly Thr Thr Val Thr Val Ser Ser
        115                 120

<210> SEQ ID NO 231
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Leu Tyr
            20                  25                  30

Asn Tyr Val Ser Trp Tyr Gln Gln Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Thr Ser Gly Asn Thr Ala Ser Leu Thr Ile Ser Gly Leu
65                  70                  75                  80

Gln Ala Asp Asp Glu Ala Asp Tyr Ser Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 232
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
            35                  40                  45

Gly Arg Ile Tyr Ala Ser Gly Asn Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Met Thr Ala Ala Asp Thr Ala Val Tyr Tyr Cys Ala
                85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
            115                 120
```

<210> SEQ ID NO 233
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 233

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
            35                  40                  45

Gly Arg Ile Tyr Ala Ser Gly Asn Thr Asn Tyr Asn Pro Ser Leu Lys
 50                  55                  60

Ser Arg Val Thr Met Ser Val Asp Thr Ser Lys Asn Gln Phe Ser Leu
 65                  70                  75                  80

Lys Leu Ser Ser Met Thr Ala Ala Asp Thr Ala Val Tyr Tyr Cys Ala
                85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
            115                 120
```

<210> SEQ ID NO 234
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 234

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
            35                  40                  45

Gly Arg Ile Tyr Ala Ser Gly Asn Thr Asn Tyr Asn Pro Ser Leu Lys
 50                  55                  60
```

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
        115                 120

<210> SEQ ID NO 235
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
            85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
        115                 120

<210> SEQ ID NO 236
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Asp Tyr Arg Val Ala Gly Thr Tyr Tyr Tyr Tyr Gly Leu Asp
            100                 105                 110

```
Val Trp Gly Gln Gly Thr Thr Val Thr Val Ser Ser
        115                 120
```

<210> SEQ ID NO 237
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
        115                 120
```

<210> SEQ ID NO 238
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
        115                 120
```

<210> SEQ ID NO 239
<211> LENGTH: 124
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 239

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Arg Val Ala Gly Thr Tyr Tyr Tyr Tyr Gly Leu Asp
                100                 105                 110

Val Trp Gly Gln Gly Thr Thr Val Thr Val Ser Ser
            115                 120

<210> SEQ ID NO 240
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Val Tyr
            20                  25                  30

Asp Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Thr Ser Arg
                85                  90                  95

Ser Thr Trp Val Phe Gly Gly Gly Thr Lys Leu Thr Val Leu
                100                 105                 110
```

METHODS OF TREATING AND PREDICTING NON-RESPONSE TO ANTI-TNF TREATMENT IN SUBJECTS WITH INFLAMMATORY BOWEL DISEASE

PRIORITY

This application claims priority to U.S. Provisional Application Ser. No. 62/487,971 filed Apr. 20, 2017, the entirety of which is hereby incorporated by reference herein.

STATEMENT REGARDING FEDERALLY-SPONSORED RESEARCH OR DEVELOPMENT

This invention was made with government support under Grant No. DK046763 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy created Apr. 18, 2018, is named 52388-729_201_SL and is 164,651 bytes in size.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Inflammatory bowel disease (IBD) has two common forms, Crohn's disease (CD) and ulcerative colitis (UC), which are chronic, relapsing inflammatory disorders of the gastrointestinal tract. In 2015, an estimated 1.3% of adults in the United States (3 million) reported being diagnosed with either CD or UC.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 3A shows the association of rs5745994 with TNFR1 levels. FIG. 3B shows association of rs5745994 with TNFR2 levels.

SUMMARY

Figure 1:
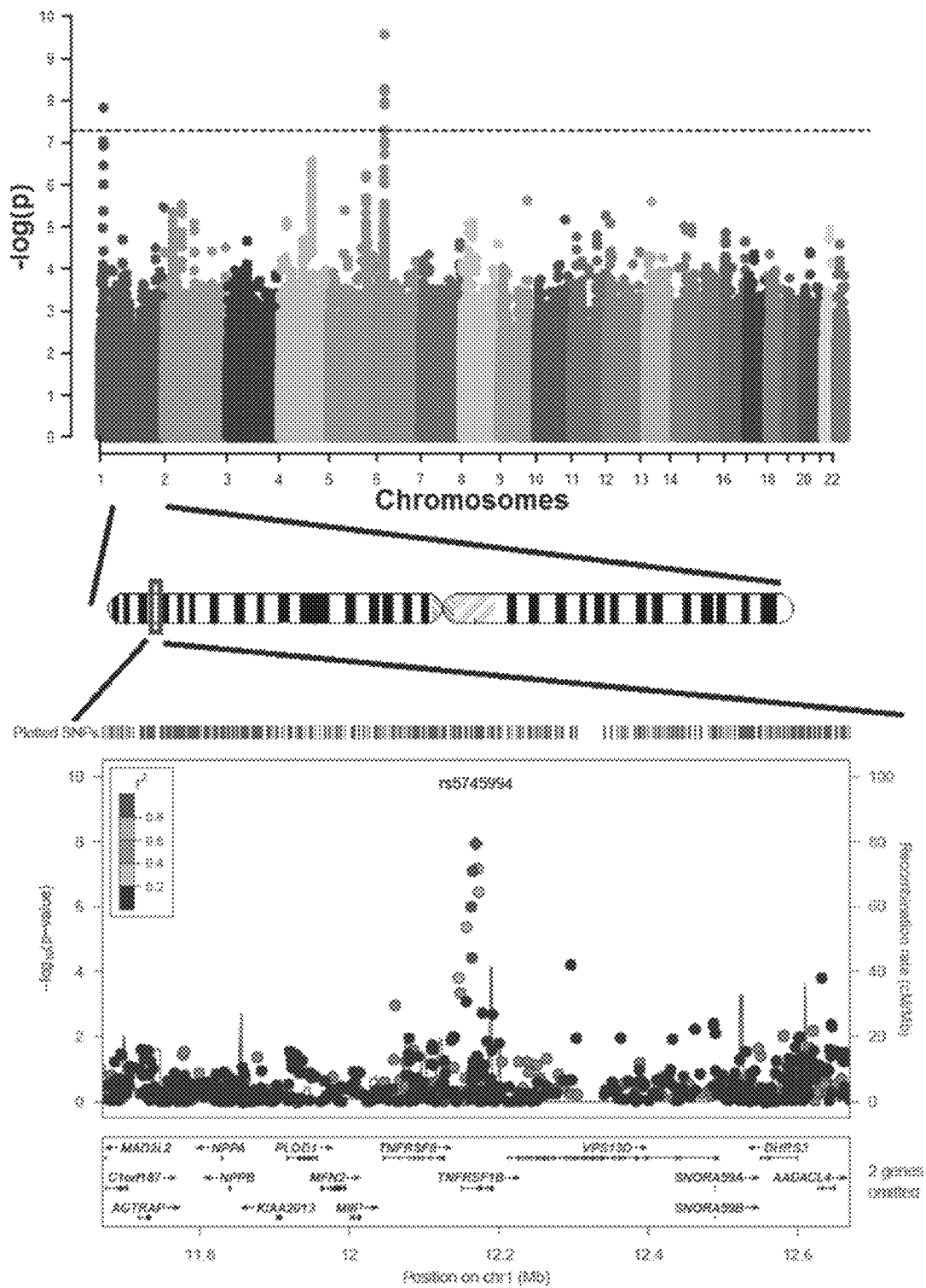
FIG. 1 depicts in accordance with various embodiments of an aspect provided herein, genome-wide association with ANCA level in discovery cohort.

It is hypothesized that IBD is caused by an inappropriate immune response to normal enteric flora in genetically susceptible individuals. In addition, there is a higher prevalence of serological responses to microbial or autoantigens in subjects diagnosed with IBD. A number of serological markers have been used in clinical practice, including atypical perinuclear antineutrophil cytoplasmic antibody (ANCA). Studies have investigated the potential value of serological markers, like ANCA, in the diagnosis and characterization of IBD.

Anti-tumor necrosis factor (TNF), or TNF-alpha (TNF-α), is a gene that encodes a multifunctional proinflammatory cytokine implicated in a variety of inflammatory diseases and disorders, including IBD. Several anti-TNF-alpha blocking strategies have been evaluated in patients with IBD, including infliximab, adalimumab, and certolizumab. Various past studies have demonstrated that infliximab has the potential to be effective for the induction and maintenance response and remission in some CD patients. However, the clinical trial data for all anti-TNF-alpha therapies among adult CD patients report that 40% of patients do not respond to the induction phase (primary non-responder) and that approximately 40% of those patients who do enter the maintenance phase of the trial lose response over time. Inter-individual variability in therapeutic response may be best explained by genetic variability and non-genetic factors, such as serological markers, as they relate to IBD pathogenesis and mechanism of action of this class of therapies. The potential clinical and genetic associations between genetic risk variants, ANCA, and IBD may provide important insights to treating or predicting anti-TNF non-response in patients with IBD.

There is no single or combination diagnostic test that can predict, with a high enough degree of accuracy, patients who will primarily not respond to anti-TNF therapy. With new treatments available, using risk single nucleotide polymorphisms (SNPs) disclosed herein in combination with ANCA to identifying subjects non-responsive to anti-TNF therapy would be a great test to eliminate expensive delay of effective treatment by a different drug, such an inhibitor of a different target, like tumor necrosis family ligand 1 (TL1A).

Aspects disclosed herein are based, at least in part, on these findings and addresses the need in the art for methods of identifying and treating a subject that is non-responsive to anti-TNF therapy and a method of selecting a therapy for a subject with an IBD using TNFRSF1B and ANCA.

In an aspect, the present application provides methods and systems for treating an inflammatory disease or condition, or fibrostenotic and/or fibrotic disease in a subject comprising with a therapeutically effective amount of a therapeutic agent, provided a level of antineutrophil cytoplasmic antibody (ANCA), or a presence of a genetic risk variant comprising a "C" at nucleobase 256 within rs5745994 of a gene locus TNFRSF1B, or a combination thereof, is detected in a biological sample obtained from the subject. In some cases, a first threshold level of ANCA that is at, or above, 100 ELISA units (EU) is used as an independent indicator that the subject is non-responsive, or susceptible to non-response, to anti-TNF therapy. In some cases, a second threshold level of ANCA that is below the first threshold level and at, or above 50 EU, is an indicator of the subject being, or being susceptible to, non-response to anti-TNF therapy if either (i) a decrease in circulating TNFR2 levels and/or (ii) a presence of a genetic risk variant or SNP at the TNFRSF1B gene locus is detected in the biological sample obtained from the subject. In some cases, the therapeutic agent inhibits the activity or expression of gene expression products from genes comprising TL1A, JAK1, GPR35, ADCY7, IFNG, TNFSF8, PFKFB3, SKAP2, GPR65, SPRED2, IL18R1, and/or GSDMB. In some cases, the therapeutic agent comprises an anti-TL1A antibody.

Further provided are methods of detecting, and kits for detecting, ANCA levels, the presence of the genetic risk variant or genotype, and/or TNFR2 levels in a biological sample obtained from a subject with an inflammatory disease or condition, or fibrostenotic and/or fibrotic disease. Such genetic risk variants or genotypes comprise single nucleotide polymorphisms (SNPs) in rs5745994 and/or rs11757159. Exemplary detection methods involve hybridization assays using nucleic acid probes specific for the SNPs. In some cases, the methods of detecting, and kits for detecting, are used to treat the subject as disclosed herein.

In one aspect, provided herein are methods of treating a subject with an inflammatory disease or condition, or fibrostenotic and/or fibrotic disease, comprising administering to the subject a therapeutically effective amount of a therapeutic agent, provided a level of antineutrophil cytoplasmic antibody (ANCA), or a presence of a genetic risk variant comprising a risk allele at nucleobase 256 within rs5745994 of a gene locus TNFRSF1B (SEQ ID NO: 1), or a combination thereof, is detected in a biological sample obtained from the subject. In some embodiments the genetic risk variant comprises a "C" at nucleobase 501 within rs11757159 of gene locus HLA-DRB6 (SEQ ID NO: 2). In some embodiments, the genetic risk variant comprises a "C" at nucleobase 256 within rs5745994 of a gene locus TNFRSF1B (SEQ ID NO: 1). In some embodiments, a single copy of the genetic risk variant is detected. In some embodiments a single copy of the genetic risk variant confers a heterozygous risk genotype. In some embodiments, two copies of the genetic risk variant are detected. In some embodiments, two copies of the genetic risk variant confers a homozygous risk genotype. In some embodiments, a decreased level of TNFR2 is detected in the biological sample obtained from the subject, compared to a reference value obtained from an individual who is not a carrier of the genetic risk variant. In some embodiments, the level of ANCA is at or above a first threshold level comprising 100 ELISA units (EU). In some embodiments, a level of ANCA that is at, or above, the first threshold level detected in the biological sample obtained from the subject is an independent indicator that the subject is non-responsive, or is susceptible to non-response, to anti-TNF therapy. In some embodiments, the level of ANCA is lower than the first threshold level and higher than a second threshold level comprising 50 EU. In some embodiments, the level of ANCA is between 50 and 60 EU. In some embodiments, the ANCA level is between 60 and 70 EU. In some embodiments, the ANCA level is between 70 and 80 EU. In some embodiments, the ANCA level is between 80 and 90 EU. In some embodiments, the ANCA level is above 90 EU and below 100 EU. In some embodiments, a level of ANCA below 100 EU and at or above 50 EU, the presence of the genetic risk variant, and a decreased level of TNFR2, detected in the biological sample obtained from the subject are indicative that the subject is non-responsive, or is susceptible to non-response, to anti-TNF therapy. In some embodiments, the presence of the genetic risk variant detected in the biological sample obtained from the subject is indicative that the subject is non-responsive, or is susceptible to non-response, to anti-TNF therapy. In some embodiments, a level of ANCA below 100 EU and at or above 50 EU and the presence of the genetic risk variant detected in the biological sample obtained from the subject are indicative that the subject is non-responsive, or is susceptible to non-response, to anti-TNF therapy. In some embodiments, a level of ANCA below 100 EU and at or above 50 EU and a decreased level of TNFR2, detected in the biological sample obtained from the subject are indicative that the subject is non-responsive, or is susceptible to non-response, to anti-TNF therapy. In some embodiments, the presence of the genetic risk variant and a decreased level of TNFR2 detected in a biological sample obtained from the subject are indicative that the subject is non-responsive, or is susceptible to non-response, to anti-TNF therapy. In some embodiments, the level of ANCA is detected using an assay comprising an anti-ANCA antibody. In some embodiments, the assay is an enzyme-linked immunosorbent assay (ELISA). In some embodiments, the ELISA is an indirect ELISA. In some embodiments, the ELISA is a fixed leukocyte ELISA. In some embodiments, the ELISA is a fixed neutrophil ELISA. In some embodiments, the inflammatory disease or condition, or fibrostenotic and/or fibrotic disease, comprises inflammatory bowel disease (IBD), Crohn's disease (CD), perianal Crohn's disease (pCD), ulcerative colitis (UC), rheumatoid arthritis, multiple sclerosis, psoriasis, chronic colitis, pancreatitis, leukopenia, colonic fibrosis, primary sclerosing cholangitis, progressive systemic sclerosis, chronic asthma, or fibrostenosis of a small and/or large intestine, or a combination thereof. In some embodiments, the genetic risk variant is detected by contacting the biological sample obtained from the subject with a nucleic acid sequence capable of hybridizing to 10 contiguous nucleobases of SEQ ID NO. 1 spanning nucleobase 256 under standard hybridization conditions. In some embodiments, the standard hybridization conditions comprise an annealing temperature between about 30° C. and about 65° C. In some embodiments, the therapeutic agent comprises an agonist or an antagonist of gene expression products from genes comprising TL1A, JAK1, GPR35, ADCY7, IFNG, TNFSF8, PFKFB3, SKAP2, GPR65, SPRED2, IL18R1, and/or GSDMB. In some embodiments, the therapeutic agent comprises an antibody, small molecule, or stem cell therapy. In some embodiments, the therapeutic agent comprises an antibody that inhibits the expression or activity of TL1A, JAK1, GPR35, ADCY7, IFNG, TNFSF8, PFKFB3, SKAP2, GPR65, SPRED2, IL18R1, and/or GSDMB. In some embodiments, the therapeutic agent comprises an anti-TLA antibody. In some embodiments, the therapeutic is second-line to an anti-TNF therapy, a steroid, and/or an immunomodulator.

In another aspect, the present application provides methods comprising: assaying to detect in a biological sample obtained from a subject with an inflammatory disease or condition, or fibrostenotic and/or fibrotic disease a level of antineutrophil cytoplasmic antibody (ANCA), a presence of a genetic risk variant comprising a risk allele at nucleobase 256 within rs5745994 of a gene locus TNFRSF1B, or a combination thereof; identifying the subject as being non-responsive to anti-TNF therapy, or susceptible to non-response to anti-TNF therapy, provided (i) a level of ANCA that is at or above a first threshold level comprising 100 ELISA units (EU), or (ii) a level of ANCA that is lower than the first threshold level and above a second threshold level comprising about 50 EU, and the presence of the genetic risk variant, are detected in the biological sample obtained from the subject. In some embodiments the genetic risk variant comprises a "C" at nucleobase 501 within rs11757159 of gene locus HLA-DRB6. In some embodiments, the genetic risk variant comprises a "C" at nucleobase 256 within rs5745994 of a gene locus TNFRSF1B (SEQ ID NO: 1). In some embodiments, a single copy of the genetic risk variant is detected. In some embodiments a single copy of the genetic risk variant confers a heterozygous risk genotype. In some embodiments, two copies of the genetic risk variant are detected. In some embodiments, two copies of the genetic risk variant confers a homozygous risk genotype. In some embodiments, the methods further comprise assaying to detect a decreased level of TNFR2 is detected in the biological sample obtained from the subject, as compared to a reference value obtained from an individual who is not a carrier of the genetic risk variant. In some embodiments, the level of ANCA is at or above a first threshold level comprising 100 ELISA units (EU). In some embodiments, a level of ANCA that is at, or above, the first threshold level detected in the biological sample obtained from the subject is an independent indicator that the subject is non-responsive, or is susceptible to non-response, to anti-TNF therapy. In some embodiments, the level of ANCA is lower than the first threshold level and higher than a second threshold level comprising 50 EU. In some embodiments, the level of ANCA is between 50 and 60 EU. In some embodiments, the ANCA level is between 60 and 70 EU. In some embodiments, the ANCA level is between 70 and 80 EU. In some embodiments, the ANCA level is between 80 and 90 EU. In some embodiments, the ANCA level is above 90 EU and below 100 EU. In some embodiments, a level of ANCA below 100 EU and at or above 50 EU, the presence of the genetic risk variant, and a decreased level of TNFR2, detected in the biological sample obtained from the subject are indicative that the subject is non-responsive, or is susceptible to non-response, to anti-TNF therapy. In some embodiments, the presence of the genetic risk variant detected in the biological sample obtained from the subject is indicative that the subject is non-responsive, or is susceptible to non-response, to anti-TNF therapy. In some embodiments, a level of ANCA below 100 EU and at or above 50 EU and the presence of the genetic risk variant detected in the biological sample obtained from the subject are indicative that the subject is non-responsive, or is susceptible to non-response, to anti-TNF therapy. In some embodiments, a level of ANCA below 100 EU and at or above 50 EU and a decreased level of TNFR2, detected in the biological sample obtained from the subject are indicative that the subject is non-responsive, or is susceptible to non-response, to anti-TNF therapy. In some embodiments, the presence of the genetic risk variant and a decreased level of TNFR2 detected in a biological sample obtained from the subject are indicative that the subject is non-responsive, or is susceptible to non-response, to anti-TNF therapy. In some embodiments, methods further comprise treating the subject with a therapeutically effective amount of a therapeutic agent, provided the subject is identified as being non-responsive to anti-TNF therapy, or susceptible to non-response to anti-TNF therapy. In some embodiments, the therapeutic agent comprises an agonist or an antagonist of gene expression products from genes comprising TL1A, JAK1, GPR35, ADCY7, IFNG, TNFSF8, PFKFB3, SKAP2, GPR65, SPRED2, IL18R1, and/or GSDMB. In some embodiments, the therapeutic agent comprises an antibody, small molecule, or stem cell therapy. In some embodiments, the therapeutic agent comprises an antibody that inhibits the expression or activity of TL1A, JAK1, GPR35, ADCY7, IFNG, TNFSF8, PFKFB3, SKAP2, GPR65, SPRED2, IL18R1, and/or GSDMB. In some embodiments, the therapeutic agent comprises an anti-TLA antibody. In some embodiments, the therapeutic is second-line to an anti-TNF therapy, a steroid, and/or an immunomodulator. In some embodiments, the inflammatory disease or condition, or fibrostenotic and/or fibrotic disease, comprises inflammatory bowel disease (IBD), Crohn's disease (CD), perianal Crohn's disease (pCD), ulcerative colitis (UC), rheumatoid arthritis, multiple sclerosis, psoriasis, chronic colitis, pancreatitis, leukopenia, colonic fibrosis, primary sclerosing cholangitis, progressive systemic sclerosis, chronic asthma, or fibrostenosis of a small and/or large intestine, or a combination thereof. In some embodiments, the level of ANCA is detected using an assay comprising an anti-ANCA antibody. In some embodiments, the assay is an enzyme-linked immunosorbent assay (ELISA). In some embodiments, the ELISA is an indirect ELISA. In some embodiments, the ELISA is a fixed leukocyte ELISA. In some embodiments, the ELISA is a fixed neutrophil ELISA. In some embodiments, the genetic risk variant is detected by contacting the biological sample obtained from the subject with a nucleic acid sequence capable of hybridizing to 10 contiguous nucleobases of SEQ ID NO. 1 spanning nucleobase 256 under standard hybridization conditions. In some embodiments, the standard hybridization conditions comprise an annealing temperature between about 30° C. and about 65° C.

In another aspect, the present application provides kits comprising a composition comprising at least 10 but less than 50 contiguous nucleobase residues of SEQ ID NO. 1, wherein the contiguous nucleobase residues comprise the nucleobase at position 256 of SEQ ID NO. 1, and wherein the contiguous nucleobase residues are connected to a detectable molecule comprising a fluorophore, and a primer pair configured to hybridize to 10 contiguous nucleobases of SEQ ID NO. 1 spanning nucleobase 256. In some embodiments, the kit further comprises a fixed enzyme-linked immunosorbent assay (fixed-ELISA) comprising an anti-ANCA antibody. In some embodiments, the fixed-ELISA is a fixed leukocyte ELISA. The some embodiments, the ELISA is a fixed neutrophil ELISA. In some embodiments the kit is used for the treatment of a subject who has an inflammatory disease or condition, or fibrostenotic and/or fibrotic disease with the therapeutic agent disclosed herein. In some embodiments, treatment of the subject comprises administering to the subject a therapeutically effect amount of a therapeutic agent. In some embodiments, the therapeutic agent comprises an agonist or an antagonist of gene expression products from genes comprising TL1A, JAK1, GPR35, ADCY7, IFNG, TNFSF8, PFKFB3, SKAP2, GPR65, SPRED2, IL18R1, and/or GSDMB. In some embodiments, the therapeutic agent comprises an antibody, small molecule, or stem cell therapy. In some embodiments, the therapeutic agent comprises an antibody that inhibits the expression or activity of TL1A, JAK1, GPR35, ADCY7, IFNG, TNFSF8, PFKFB3, SKAP2, GPR65, SPRED2, IL18R1, and/or GSDMB. In some embodiments, the therapeutic agent comprises an anti-TLA antibody. In some embodiments, the therapeutic is second-line to an anti-TNF therapy, a steroid, and/or an immunomodulator.

Certain Terminologies

One skilled in the art will recognize many methods and materials similar or equivalent to those described herein, which could be used in the practice of aspects provided herein. Other features and advantages of aspects provided herein will become apparent from the following detailed description, taken in conjunction with the accompanying drawings, which illustrate, by way of example, various features of embodiments of aspects provided herein. Indeed, aspects provided herein are in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the aspects provided herein, because the scope of the aspects provided herein is limited only by the claims. Unless otherwise defined, all technical and scientific terms used herein have the same meaning as commonly understood by one of ordinary skill in the art to which aspects provided herein belong.

Non-limiting examples of "Biological sample" as used herein means any biological material from which nucleic acids and/or proteins can be obtained. As non-limiting examples, the term encompasses whole blood, peripheral blood, plasma, serum, saliva, mucus, urine, semen, lymph, fecal extract, cheek swab, cells or other bodily fluid or tissue, including but not limited to tissue obtained through surgical biopsy or surgical resection. In various embodiments, the sample comprises tissue from the large and/or small intestine. In various other embodiments, the large intestine sample comprises the cecum, colon (the ascending colon, the transverse colon, the descending colon, and the sigmoid colon), rectum and/or the anal canal. In yet other embodiments, the small intestine sample comprises the duodenum, jejunum, and/or the ileum. Alternatively, a sample can be obtained through primary patient derived cell lines, or archived patient samples in the form of preserved samples, or fresh frozen samples.

"Treatment" and "treating" as used herein refer to both therapeutic treatment and prophylactic or preventative measures, wherein the object is to prevent or slow down (lessen) the targeted pathologic condition, prevent the pathologic condition, pursue or obtain good overall survival, or lower the chances of the individual developing the condition even if the treatment is ultimately unsuccessful. Those in need of treatment include those already with the condition as well as those prone to have the condition or those in whom the condition is to be prevented.

"SNP" as used herein means single nucleotide polymorphism.

"Genetic risk variant" as used herein refers to an allele, whose presence in a polynucleotide sequence is associated with a disease or condition, or susceptibility to developing the disease or condition. Non-limiting examples of diseases or conditions include, inflammatory disease or condition, or fibrostenotic and/or fibrotic disease, comprises inflammatory bowel disease (IBD), Crohn's disease (CD), perianal Crohn's disease (pCD), ulcerative colitis (UC), rheumatoid arthritis, multiple sclerosis, psoriasis, chronic colitis, pancreatitis, leukopenia, colonic fibrosis, primary sclerosing cholangitis, progressive systemic sclerosis, chronic asthma, fibrostenosis of a small and/or large intestine, anti-TNF non-response, leukopenia, and pancreatitis.

"IBD", "CD" and "UC" as used herein refer to Inflammatory Bowel Disease, Crohn's Disease, and Ulcerative Colitis, respectively.

As used herein, "ANCA" means anti-neutrophil cytoplasmic antibodies.

The terms "increased," or "increase" are used herein to generally mean an increase by a statically significant amount; in some embodiments, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level. Other examples of "increase" include an increase of at least 2-fold, at least 5-fold, at least 10-fold, at least 20-fold, at least 50-fold, at least 100-fold, at least 1000-fold or more as compared to a reference level.

The terms, "decreased" or "decrease" are used herein generally to mean a decrease by a statistically significant amount. In some embodiments, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

"Non-response" or "non-responsive" as used herein, refers to a condition characterized by a subject not responding to the induction of a therapy (primary non-response) or a condition characterized by the subject losing response to the therapy during the treatment (secondary loss of response). In some embodiments, the therapy may include any therapeutic agent or drug therapy used in the "treating" or "treatment" of a subject, as disclosed herein.

"Susceptible" or "susceptibility" to a disease or condition as used herein, refers to a condition of the subject characterized by an increased likelihood to develop the disease or condition, as compared to an individual who is not determined to be susceptible to the disease or condition. In some embodiments, the condition comprises non-response to anti-TNF therapy. In some embodiments, susceptibility to non-response to anti-TNF therapy in a subject means the subject will more likely than not develop non-response to anti-TNF therapy, if an anti-TNF therapy is administered to the subject.

DETAILED DESCRIPTION

In one aspect, provided herein, are methods of obtaining a biological sample from a subject with an inflammatory disease or condition or fibrostenotic and/or fibrotic disease, and assaying the sample to detect level of antineutrophil cytoplasmic antibody (ANCA), or a presence of a risk allele, "C" at nucleobase 256 within rs5745994 of a gene locus TNFRSF1B, or a decreased level of circulating TNFR2, or a combination thereof, which is indicative of non-response to anti-TNF therapy in the subject. In one aspect, provided herein, are methods of treating the inflammatory disease or condition, or fibrostenotic and/or fibrotic disease, in the subject with therapeutic agent, provided the subject is identified as being non-responsive to anti-TNF therapy. In one aspect, provided herein, are compositions and kits used to identify non-response to anti-TNF therapy in a subject. In some embodiments, the therapeutic agent is a second-line therapy, comprising an anti-TL1A therapy. In some embodiments, the inflammatory disease comprises Inflammatory Bowel Disease (IBD).

Methods of Treating an Inflammatory Disease or Condition or Fibrostenotic and/or Fibrotic Disease In one aspect, provided herein are methods of treating an inflammatory disease or condition or fibrostenotic and/or fibrotic disease, in a subject. In some embodiments, the subject is a mammal. In some embodiments, the subject is a human. In some embodiments, the inflammatory condition or disease comprises a condition that involves chronic inflammation of the body caused by pathogens, viruses, foreign bodies or overactive immune responses. Non-limiting examples of inflammatory conditions include, but are not limited to, inflammatory bowel disease (IBD), Crohn's disease (CD), perianal Crohn's disease (pCD), ulcerative colitis (UC), rheumatoid arthritis, multiple sclerosis, psoriasis, chronic colitis, pancreatitis, leukopenia, or a combination thereof. In some embodiments, the fibrostenotic and/or fibrotic disease comprises colonic fibrosis, primary sclerosing cholangitis, progressive systemic sclerosis, chronic asthma, or fibrostenosis of a small and/or large intestine. In some embodiments, the subject is susceptible to, or is inflicted with, thiopurine toxicity, or a disease caused by thiopurine toxicity (such as pancreatitis or leukopenia). In further embodiments provided, the subject is non-responsive to a therapy comprising anti-TNF alpha therapy, anti-a4-b7 therapy (vedolizumab), anti-IL12p40 therapy (ustekinumab), Thalidomide, or Cytoxin.

Therapeutic Agent

In one aspect, provided herein are methods of treating an inflammatory disease or condition or fibrostenotic and/or fibrotic disease in a subject by administering a therapeutically effective amount of a therapeutic agent to the subject. In some embodiments, the therapeutic agent is second-line to a first therapy, or therapies, comprising an anti-TNF therapy, a steroid, and/or an immunomodulator. A second-line therapy is a therapy that is administered to a subject who (i) does not respond to the induction of a first therapy (e.g., "primary non-response"), or is predicted to experience primary non-response, or (ii) experiences loss of response to the first therapy during the treatment (e.g., "secondary loss of response"). In some embodiments, the therapeutic agent is an antibody, small molecule, siRNA/short hairpin RNA, peptide, vaccine, or cell-based therapy.

In some embodiments, the therapeutic agent is an immunosuppressant, or from a class of drugs that suppress, or reduce, the strength of the immune system. In some embodiments, the immunosuppressant is an antibody. In some embodiments, the immunosuppressant is a small molecule. Non-limiting examples of immunosuppressant therapeutic agents include STELARA® (ustekinumab), azathioprine (AZA), 6-mercaptopurine (6-MP), methotrexate, and cyclosporin A. (CsA). In some embodiments, the therapeutic agent is a selective anti-inflammatory drug, or from a class of drugs that specifically target pro-inflammatory molecules in the body. The pro-inflammatory molecules may comprise cytokines, cell trafficking molecules, and/or molecules involved in the innate or adaptive immune responses. The anti-inflammatory drug may comprise an antibody. The anti-inflammatory drug may comprise a small molecule. Non-limiting examples of anti-inflammatory drugs include ENTYVIO® (vedolizumab), corticosteroids, aminosalicylates, mesalamine, COLAZAL® (balsalazide), DIPENTUM® (olsalazine), anti-IL17A (secukinumab), anti-IL13 (tralokinumab and anrukinzumab), MAdCAM-1 (PF-00547659), anti-ICAM (alicaforsen), anti-IL12p40 (ustekinumab), briakinumab (ABT-874), anti-IL23p19 (MED2070), SMAD7-inhibitor (mongersen), modulators of TGFB1, S1PR agonists, anti-TL1A, anti-IL6, anti-IL6R, gp130-Fc, and cirsilineol.

In some embodiments, the therapeutic agent comprises a stem cell therapy. The stem cell therapy may be embryonic or somatic stem cells. The stem cells may be isolated from a donor (allogeneic) or isolated from the subject (autologous). The stem cells may be expanded adipose-derived stem cells (eASCs), hematopoietic stem cells (HSCs), mesenchymal stem (stromal) cells (MSCs), regulatory T cells (Tregs), or induced pluripotent stem cells (iPSCs) derived from the cells of the subject. The stem cell therapy may specifically target any of the gene expression products disclosed herein. The stem cell therapy may be an immunosuppressant, or anti-inflammatory. In some embodiments, the stem cell therapy comprises Cx601/Alofisel® (darvadstrocel).

In some embodiments, the therapeutic agent comprises a small molecule. The small molecule may be used to treat inflammatory diseases or conditions, or fibrostenotic or fibrotic disease. In some embodiments, the small molecule is an agonist. An agonist is a therapeutic agent that causes action in the target molecule. In some embodiments, the small molecule is an antagonist. An antagonist is a therapeutic agent that blocks the action of the target molecule. Non-limiting examples of small molecules include OTEXLA® (apremilast), alicaforsen, and ozanimod (RPC-1063).

In some embodiments, the therapeutic agent comprises an agonist. In some embodiments, the therapeutic agent comprises an antagonist. In some embodiments, the therapeutic agent comprises a small molecule. In some embodiments, the therapeutic agent comprises an antibody. The therapeutic agent may comprise an agonist or an antagonist of TL1A, JAK1, GPR35, ADCY7, IFNG, TNFSF8, PFKFB3, SKAP2 GPR65, SPRED2, IL18R1, GSDMB, or gene expression products from genes implicated in the pathogenesis of inflammatory, fibrotic, or fibrostenotic disease. The antagonist may inhibit the activity or expression of TL1A, JAK1, GPR35, ADCY7, IFNG, TNFSF8, PFKFB3, SKAP2 GPR65, SPRED2, IL18R1, GSDMB. The therapeutic agent may be an allosteric modulator of TL1A, JAK1, GPR35, ADCY7, IFNG, TNFSF8, PFKFB3, SKAP2 GPR65, SPRED2, IL18R1, GSDMB, or gene expression products from genes implicated in the pathogenesis of inflammatory, fibrotic, or fibrostenotic disease. Non-limiting examples of JAK1 inhibitors include ruxolitinib (INCB018424), s-ruxolitinib (INCB018424), baricitinib (LY3009104, INCB028050), filgotinib (GLPG0634), momelotinib (CYT387), cerdulatinib (PRT062070, PRT2070), LY2784544, NVP-BSK805, 2HC1, Tofacitinib (CP-690550, tasocitinib), XL019, pacritinib (SB1518), tofacitinib, or ZM 39923 HCl. In some embodiments, inhibitors of TNFSF8 include anti-CD30L and anti-CD30 therapies. In some embodiments, inhibitors of PFKFB3 include 1-(4-pyridinyl)-3-(2-quinolinyl)-2-propen-1-one (PFK 15).

In some embodiments, the therapeutic agent is an inhibitor of CD30L expression or activity. In some embodiments, the inhibitor of CD30L comprises an anti-CD30L antibody. The anti-CD30L may comprise a heavy chain comprising three complementarity-determining regions: HCDR1, HCDR2, and HCDR3; and a light chain comprising three complementarity-determining regions: LCDR1, LCDR2, and LCDR3. In some embodiments, the anti-CD30L antibody comprises a HCDR1 comprising SEQ ID NO: 186, a HCDR2 comprising SEQ ID NO: 187, a HCDR3 comprising SEQ ID NO: 188, a LCDR1 comprising SEQ ID NO: 189, a LCDR2 comprising SEQ ID NO: 190, and a LCDR3 comprising SEQ ID NO: 191.

In some embodiments, the anti-CD30L antibody comprises a HCDR1 comprising SEQ ID NO: 192, a HCDR2 comprising SEQ ID NO: 193, a HCDR3 comprising SEQ ID NO: 194, a LCDR1 comprising SEQ ID NO: 195, a LCDR2 comprising SEQ ID NO: 196, and a LCDR3 comprising SEQ ID NO: 197.

In some embodiments, the anti-CD30L antibody comprises a HCDR1 comprising SEQ ID NO: 198, a HCDR2 comprising SEQ ID NO: 199, a HCDR3 comprising SEQ ID NO: 200, a LCDR1 comprising SEQ ID NO: 201, a LCDR2 comprising SEQ ID NO: 202, and a LCDR3 comprising SEQ ID NO: 203.

In some embodiments, the anti-CD30L antibody comprises a HCDR1 comprising SEQ ID NO: 204, a HCDR2 comprising SEQ ID NO: 205, a HCDR3 comprising SEQ ID NO: 206, a LCDR1 comprising SEQ ID NO: 207, a LCDR2 comprising SEQ ID NO: 208, and a LCDR3 comprising SEQ ID NO: 209.

In some embodiments, the anti-CD30L antibody comprises a HCDR1 comprising SEQ ID NO: 210, a HCDR2 comprising SEQ ID NO: 211, a HCDR3 comprising SEQ ID NO: 212, a LCDR1 comprising SEQ ID NO: 213, a LCDR2 comprising SEQ ID NO: 214, and a LCDR3 comprising SEQ ID NO: 215.

In some embodiments, the anti-CD30L antibody comprises a HCDR1 comprising SEQ ID NO: 216, a HCDR2 comprising SEQ ID NO: 217, a HCDR3 comprising SEQ ID NO: 218, a LCDR1 comprising SEQ ID NO: 219, a LCDR2 comprising SEQ ID NO: 220, and a LCDR3 comprising SEQ ID NO: 221.

In some cases, the anti-CD30L antibody comprises a heavy chain (HC) variable domain comprising SEQ ID NO: 222 and a light chain (LC) variable domain comprising SEQ ID NO: 223. In some cases, the anti-CD30L antibody comprises a heavy chain (HC) variable domain comprising SEQ ID NO: 224 and a light chain (LC) variable domain comprising SEQ ID NO: 225. In some cases, the anti-CD30L antibody comprises a heavy chain (HC) variable domain comprising SEQ ID NO: 226 and a light chain (LC) variable domain comprising SEQ ID NO: 227. In some cases, the anti-CD30L antibody comprises a heavy chain (HC) variable domain comprising SEQ ID NO: 228 and a light chain (LC) variable domain comprising SEQ ID NO: 229. In some cases, the anti-CD30L antibody comprises a heavy chain (HC) variable domain comprising SEQ ID NO: 230 and a light chain (LC) variable domain comprising SEQ ID NO: 231. In some cases, the anti-CD30L antibody comprises a heavy chain (HC) variable domain comprising SEQ ID NO: 232 and a light chain (LC) variable domain comprising SEQ ID NO: 240. In some cases, the anti-CD30L antibody comprises a heavy chain (HC) variable domain comprising SEQ ID NO: 233 and a light chain (LC) variable domain comprising SEQ ID NO: 240. In some cases, the anti-CD30L antibody comprises a heavy chain (HC) variable domain comprising SEQ ID NO: 234 and a light chain (LC) variable domain comprising SEQ ID NO: 240. In some cases, the anti-CD30L antibody comprises a heavy chain (HC) variable domain comprising SEQ ID NO: 235 and a light chain (LC) variable domain comprising SEQ ID NO: 240. In some cases, the anti-CD30L antibody comprises a heavy chain (HC) variable domain comprising SEQ ID NO: 236 and a light chain (LC) variable domain comprising SEQ ID NO: 240. In some cases, the anti-CD30L antibody comprises a heavy chain (HC) variable domain comprising SEQ ID NO: 237 and a light chain (LC) variable domain comprising SEQ ID NO: 240. In some cases, the anti-CD30L antibody comprises a heavy chain (HC) variable domain comprising SEQ ID NO: 238 and a light chain (LC) variable domain comprising SEQ ID NO: 240. In some cases, the anti-CD30L antibody comprises a heavy chain (HC) variable domain comprising SEQ ID NO: 239 and a light chain (LC) variable domain comprising SEQ ID NO: 240.

In some embodiments, the therapeutic agent is an inhibitor of TL1A expression or activity. In some embodiments, the inhibitor of TL1A expression or activity is effective to inhibit TL1A-DR3 binding. In some embodiments, the inhibitor of TL1A expression or activity comprises an allosteric modulator of TL1A. An allosteric modulator of TL1A may indirectly influence the effects TL1A on DR3, or TR6/DcR3 on TL1A or DR3. The inhibitor of TL1A expression or activity may be a direct inhibitor or indirect inhibitor. Non-limiting examples of an inhibitor of TL1A expression include RNA to protein TL1A translation inhibitors, antisense oligonucleotides targeting the TNFSF15 mRNA (such as miRNAs, or siRNA), epigenetic editing (such as targeting the DNA-binding domain of TNFSF15, or post-translational modifications of histone tails and/or DNA molecules). Non-limiting examples of an inhibitor of TL1A activity include antagonists to the TL1A receptors, (DR3 and TR6/DcR3), antagonists to TL1A antigen, and antagonists to gene expression products involved in TL1A mediated disease. Antagonists as disclosed herein, may include, but are not limited to, an anti-TL1A antibody, an anti-TL1A-binding antibody fragment, or a small molecule. The small molecule may be a small molecule that binds to TL1A or DR3. The anti-TL1A antibody may be monoclonal or polyclonal. The anti-TL1A antibody may be humanized or chimeric. The anti-TL1A antibody may be a fusion protein. The anti-TL1A antibody may be a blocking anti-TL1A antibody. A blocking antibody blocks binding between two proteins, e.g., a ligand and its receptor. Therefore, a TL1A blocking antibody includes an antibody that prevents binding of TL1A to DR3 and/or TR6/DcR3 receptors. In a non-limiting example, the TL1A blocking antibody binds to DR3. In another example, the TL1A blocking antibody binds to DcR3. In some cases, the TL1A antibody is an anti-TL1A antibody that specifically binds to TL1A. The anti-TL1A antibody may comprise one or more of the antibody sequences of Table 1 and/or Table 2. The anti-DR3 antibody may comprise an amino acid sequence that is at least 85% identical to any one of SEQ ID NOs:152-164 and an amino acid sequence that is at least 85% identical to any one of SEQ ID NOs:165-169. The anti-DR3 antibody may comprise an amino acid sequence comprising the HCDR1, HCDR2, HCDR3 domains of any one of SEQ ID NOs:152-164 and the LCDR1, LCDR2, and LCDR3 domains of any one of SEQ ID NOs:165-169.

In some embodiments, an anti-TL1A antibody comprises a heavy chain comprising three complementarity-determining regions: HCDR1, HCDR2, and HCDR3; and a light chain comprising three complementarity-determining regions: LCDR1, LCDR2, and LCDR3. In some embodiments, the anti-TL1A antibody comprises a HCDR1 comprising SEQ ID NO: 3, a HCDR2 comprising SEQ ID NO: 4, a HCDR3 comprising SEQ ID NO: 5, a LCDR1 comprising SEQ ID NO: 6, a LCDR2 comprising SEQ ID NO: 7, and a LCDR3 comprising SEQ ID NO: 8. In some cases, the anti-TL1A antibody comprises a heavy chain (HC) variable domain comprising SEQ ID NO: 9 and a light chain (LC) variable domain comprising SEQ ID NO: 10.

In some embodiments, the anti-TL1A antibody comprises a HCDR1 comprising SEQ ID NO: 11, a HCDR2 comprising SEQ ID NO: 12, a HCDR3 comprising SEQ ID NO: 13, a LCDR1 comprising SEQ ID NO: 14, a LCDR2 comprising SEQ ID NO: 15, and a LCDR3 comprising SEQ ID NO: 16. In some cases, the anti-TL1A antibody comprises a heavy chain (HC) variable domain comprising SEQ ID NO: 17 and a light chain (LC) variable domain comprising SEQ ID NO: 18.

In some embodiments, the anti-TL1A antibody comprises a HCDR1 comprising SEQ ID NO: 19, a HCDR2 comprising SEQ ID NO: 20, a HCDR3 comprising SEQ ID NO: 21, a LCDR1 comprising SEQ ID NO: 22, a LCDR2 comprising SEQ ID NO: 23, and a LCDR3 comprising SEQ ID NO: 24. In some cases, the anti-TL1A antibody comprises a heavy chain (HC) variable domain comprising SEQ ID NO: 25 and a light chain (LC) variable domain comprising SEQ ID NO: 26.

In some embodiments, the anti-TL1A antibody comprises a HCDR1 comprising SEQ ID NO: 27, a HCDR2 comprising SEQ ID NO: 28, a HCDR3 comprising SEQ ID NO: 29, a LCDR1 comprising SEQ ID NO: 33, a LCDR2 comprising SEQ ID NO: 34, and a LCDR3 comprising SEQ ID NO: 35. In some cases, the anti-TL1A antibody comprises a HCDR1 comprising SEQ ID NO: 30, a HCDR2 comprising SEQ ID NO: 31, a HCDR3 comprising SEQ ID NO: 32, a LCDR1 comprising SEQ ID NO: 33, a LCDR2 comprising SEQ ID NO: 34, and a LCDR3 comprising SEQ ID NO: 35. In some cases, the anti-TL1A antibody comprises a heavy chain (HC) variable domain comprising SEQ ID NO: 36 and a light chain (LC) variable domain comprising SEQ ID NO: 37. In some cases, the anti-TL1A antibody comprises a heavy chain comprising SEQ ID NO: 38. In some cases, the anti-TL1A antibody comprises a light chain comprising SEQ ID NO: 39.

In some embodiments, the anti-TL1A antibody comprises a HCDR1 comprising SEQ ID NO: 40, a HCDR2 comprising SEQ ID NO: 41, a HCDR3 comprising SEQ ID NO: 42, a LCDR1 comprising SEQ ID NO: 43, a LCDR2 comprising SEQ ID NO: 44, and a LCDR3 comprising SEQ ID NO: 45. In some cases, the anti-TL1A antibody comprises a heavy chain (HC) variable domain comprising SEQ ID NO: 46 and a light chain (LC) variable domain comprising SEQ ID NO: 47.

In some embodiments, the anti-TL1A antibody comprises a HCDR1 comprising SEQ ID NO: 48, a HCDR2 comprising SEQ ID NO: 49, a HCDR3 comprising SEQ ID NO: 50, a LCDR1 comprising SEQ ID NO: 51, a LCDR2 comprising SEQ ID NO: 52, and a LCDR3 comprising SEQ ID NO: 53. In some cases, the anti-TL1A antibody comprises a heavy chain (HC) variable domain comprising SEQ ID NO: 54 and a light chain (LC) variable domain comprising SEQ ID NO: 55.

In some embodiments, the anti-TL1A antibody comprises a HCDR1 comprising SEQ ID NO: 56, a HCDR2 comprising SEQ ID NO: 58, a HCDR3 comprising SEQ ID NO: 59, a LCDR1 comprising SEQ ID NO: 61, a LCDR2 comprising SEQ ID NO: 63, and a LCDR3 comprising SEQ ID NO: 64. In some cases, the anti-TL1A antibody comprises a heavy chain (HC) variable domain comprising SEQ ID NO: 65 and a light chain (LC) variable domain comprising SEQ ID NO: 69. In some cases, the anti-TL1A antibody comprises a heavy chain (HC) variable domain comprising SEQ ID NO: 65 and a light chain (LC) variable domain comprising SEQ ID NO: 70. In some cases, the anti-TL1A antibody comprises a heavy chain (HC) variable domain comprising SEQ ID NO: 65 and a light chain (LC) variable domain comprising SEQ ID NO: 71. In some cases, the anti-TL1A antibody comprises a heavy chain (HC) variable domain comprising SEQ ID NO: 65 and a light chain (LC) variable domain comprising SEQ ID NO: 72.

In some embodiments, the anti-TL1A antibody comprises a HCDR1 comprising SEQ ID NO: 56, a HCDR2 comprising SEQ ID NO: 58, a HCDR3 comprising SEQ ID NO: 59, a LCDR1 comprising SEQ ID NO: 62, a LCDR2 comprising SEQ ID NO: 63, and a LCDR3 comprising SEQ ID NO: 64. In some cases, the anti-TL1A antibody comprises a heavy chain (HC) variable domain comprising SEQ ID NO: 65 and a light chain (LC) variable domain comprising SEQ ID NO: 73. In some cases, the anti-TL1A antibody comprises a heavy chain (HC) variable domain comprising SEQ ID NO: 65 and a light chain (LC) variable domain comprising SEQ ID NO: 74. In some cases, the anti-TL1A antibody comprises a heavy chain (HC) variable domain comprising SEQ ID NO: 65 and a light chain (LC) variable domain comprising SEQ ID NO: 75. In some cases, the anti-TL1A antibody comprises a heavy chain (HC) variable domain comprising SEQ ID NO: 65 and a light chain (LC) variable domain comprising SEQ ID NO: 76.

In some embodiments, the anti-TL1A antibody comprises a HCDR1 comprising SEQ ID NO: 56, a HCDR2 comprising SEQ ID NO: 58, a HCDR3 comprising SEQ ID NO: 59, a LCDR1 comprising SEQ ID NO: 61, a LCDR2 comprising SEQ ID NO: 63, and a LCDR3 comprising SEQ ID NO: 64. In some cases, the anti-TL1A antibody comprises a heavy chain (HC) variable domain comprising SEQ ID NO: 66 and a light chain (LC) variable domain comprising SEQ ID NO: 69. In some cases, the anti-TL1A antibody comprises a heavy chain (HC) variable domain comprising SEQ ID NO: 66 and a light chain (LC) variable domain comprising SEQ ID NO: 70. In some cases, the anti-TL1A antibody comprises a heavy chain (HC) variable domain comprising SEQ ID NO: 66 and a light chain (LC) variable domain comprising SEQ ID NO: 71. In some cases, the anti-TL1A antibody comprises a heavy chain (HC) variable domain comprising SEQ ID NO: 66 and a light chain (LC) variable domain comprising SEQ ID NO: 72.

In some embodiments, the anti-TL1A antibody comprises a HCDR1 comprising SEQ ID NO: 56, a HCDR2 comprising SEQ ID NO: 58, a HCDR3 comprising SEQ ID NO: 59, a LCDR1 comprising SEQ ID NO: 62, a LCDR2 comprising SEQ ID NO: 63, and a LCDR3 comprising SEQ ID NO: 64. In some cases, the anti-TL1A antibody comprises a heavy chain (HC) variable domain comprising SEQ ID NO: 66 and a light chain (LC) variable domain comprising SEQ ID NO: 73. In some cases, the anti-TL1A antibody comprises a heavy chain (HC) variable domain comprising SEQ ID NO: 66 and a light chain (LC) variable domain comprising SEQ ID NO: 74. In some cases, the anti-TL1A antibody comprises a heavy chain (HC) variable domain comprising SEQ ID NO: 66 and a light chain (LC) variable domain comprising SEQ ID NO: 75. In some cases, the anti-TL1A antibody comprises a heavy chain (HC) variable domain comprising SEQ ID NO: 66 and a light chain (LC) variable domain comprising SEQ ID NO: 76.

In some embodiments, the anti-TL1A antibody comprises a HCDR1 comprising SEQ ID NO: 57, a HCDR2 comprising SEQ ID NO: 58, a HCDR3 comprising SEQ ID NO: 60, a LCDR1 comprising SEQ ID NO: 61, a LCDR2 comprising SEQ ID NO: 63, and a LCDR3 comprising SEQ ID NO: 64. In some cases, the anti-TL1A antibody comprises a heavy chain (HC) variable domain comprising SEQ ID NO: 67 and a light chain (LC) variable domain comprising SEQ ID NO: 69. In some cases, the anti-TL1A antibody comprises a heavy chain (HC) variable domain comprising SEQ ID NO: 67 and a light chain (LC) variable domain comprising SEQ ID NO: 70. In some cases, the anti-TL1A antibody comprises a heavy chain (HC) variable domain comprising SEQ ID NO: 67 and a light chain (LC) variable domain comprising SEQ ID NO: 71. In some cases, the anti-TL1A antibody comprises a heavy chain (HC) variable domain comprising SEQ ID NO: 67 and a light chain (LC) variable domain comprising SEQ ID NO: 72. In some cases, the anti-TL1A antibody comprises a heavy chain (HC) variable domain comprising SEQ ID NO: 67 and a light chain (LC) variable domain comprising SEQ ID NO: 73. In some cases, the anti-TL1A antibody comprises a heavy chain (HC) variable domain comprising SEQ ID NO: 67 and a light chain (LC) variable domain comprising SEQ ID NO: 74. In some cases, the anti-TL1A antibody comprises a heavy chain (HC) variable domain comprising SEQ ID NO: 67 and a light chain (LC) variable domain comprising SEQ ID NO: 75. In some cases, the anti-TL1A antibody comprises a heavy chain (HC) variable domain comprising SEQ ID NO: 67 and a light chain (LC) variable domain comprising SEQ ID NO: 76.

In some embodiments, the anti-TL1A antibody comprises a HCDR1 comprising SEQ ID NO: 57, a HCDR2 comprising SEQ ID NO: 58, a HCDR3 comprising SEQ ID NO: 60, a LCDR1 comprising SEQ ID NO: 62, a LCDR2 comprising SEQ ID NO: 63, and a LCDR3 comprising SEQ ID NO: 64. In some cases, the anti-TL1A antibody comprises a heavy chain (HC) variable domain comprising SEQ ID NO: 68 and a light chain (LC) variable domain comprising SEQ ID NO: 73. In some cases, the anti-TL1A antibody comprises a heavy chain (HC) variable domain comprising SEQ ID NO: 68 and a light chain (LC) variable domain comprising SEQ ID NO: 74. In some cases, the anti-TL1A antibody comprises a heavy chain (HC) variable domain comprising SEQ ID NO: 68 and a light chain (LC) variable domain comprising SEQ ID NO: 75. In some cases, the anti-TL1A antibody comprises a heavy chain (HC) variable domain comprising SEQ ID NO: 68 and a light chain (LC) variable domain comprising SEQ ID NO: 76. In some cases, the anti-TL1A antibody comprises a heavy chain (HC) variable domain comprising SEQ ID NO: 68 and a light chain (LC) variable domain comprising SEQ ID NO: 69. In some cases, the anti-TL1A antibody comprises a heavy chain (HC) variable domain comprising SEQ ID NO: 68 and a light chain (LC) variable domain comprising SEQ ID NO: 70. In some cases, the anti-TL1A antibody comprises a heavy chain (HC) variable domain comprising SEQ ID NO: 68 and a light chain (LC) variable domain comprising SEQ ID NO: 71. In some cases, the anti-TL1A antibody comprises a heavy chain (HC) variable domain comprising SEQ ID NO: 68 and a light chain (LC) variable domain comprising SEQ ID NO: 72.

In some embodiments, the anti-TL1A antibody comprises a HCDR1 comprising SEQ ID NO: 77, a HCDR2 comprising SEQ ID NO: 78, a HCDR3 comprising SEQ ID NO: 79, a LCDR1 comprising SEQ ID NO: 80, a LCDR2 comprising SEQ ID NO: 81, and a LCDR3 comprising SEQ ID NO: 82. In some cases, the anti-TL1A antibody comprises a heavy chain (HC) variable domain comprising SEQ ID NO: 83 and a light chain (LC) variable domain comprising SEQ ID NO: 88. In some cases, the anti-TL1A antibody comprises a heavy chain (HC) variable domain comprising SEQ ID NO: 83 and a light chain (LC) variable domain comprising SEQ ID NO: 89. In some cases, the anti-TL1A antibody comprises a heavy chain (HC) variable domain comprising SEQ ID NO: 83 and a light chain (LC) variable domain comprising SEQ ID NO: 90. In some cases, the anti-TL1A antibody comprises a heavy chain (HC) variable domain comprising SEQ ID NO: 83 and a light chain (LC) variable domain comprising SEQ ID NO: 91. In some cases, the anti-TL1A antibody comprises a heavy chain (HC) variable domain comprising SEQ ID NO: 84 and a light chain (LC) variable domain comprising SEQ ID NO: 88. In some cases, the anti-TL1A antibody comprises a heavy chain (HC) variable domain comprising SEQ ID NO: 84 and a light chain (LC) variable domain comprising SEQ ID NO: 89. In some cases, the anti-TL1A antibody comprises a heavy chain (HC) variable domain comprising SEQ ID NO: 84 and a light chain (LC) variable domain comprising SEQ ID NO: 90. In some cases, the anti-TL1A antibody comprises a heavy chain (HC) variable domain comprising SEQ ID NO: 84 and a light chain (LC) variable domain comprising SEQ ID NO: 91. In some cases, the anti-TL1A antibody comprises a heavy chain (HC) variable domain comprising SEQ ID NO: 85 and a light chain (LC) variable domain comprising SEQ ID NO: 88. In some cases, the anti-TL1A antibody comprises a heavy chain (HC) variable domain comprising SEQ ID NO: 85 and a light chain (LC) variable domain comprising SEQ ID NO: 89. In some cases, the anti-TL1A antibody comprises a heavy chain (HC) variable domain comprising SEQ ID NO: 85 and a light chain (LC) variable domain comprising SEQ ID NO: 90. In some cases, the anti-TL1A antibody comprises a heavy chain (HC) variable domain comprising SEQ ID NO: 85 and a light chain (LC) variable domain comprising SEQ ID NO: 91. In some cases, the anti-TL1A antibody comprises a heavy chain (HC) variable domain comprising SEQ ID NO: 86 and a light chain (LC) variable domain comprising SEQ ID NO: 88. In some cases, the anti-TL1A antibody comprises a heavy chain (HC) variable domain comprising SEQ ID NO: 86 and a light chain (LC) variable domain comprising SEQ ID NO: 89. In some cases, the anti-TL1A antibody comprises a heavy chain (HC) variable domain comprising SEQ ID NO: 86 and a light chain (LC) variable domain comprising SEQ ID NO: 90. In some cases, the anti-TL1A antibody comprises a heavy chain (HC) variable domain comprising SEQ ID NO: 86 and a light chain (LC) variable domain comprising SEQ ID NO: 91. In some cases, the anti-TL1A antibody comprises a heavy chain (HC) variable domain comprising SEQ ID NO: 87 and a light chain (LC) variable domain comprising SEQ ID NO: 88. In some cases, the anti-TL1A antibody comprises a heavy chain (HC) variable domain comprising SEQ ID NO: 87 and a light chain (LC) variable domain comprising SEQ ID NO: 89. In some cases, the anti-TL1A antibody comprises a heavy chain (HC) variable domain comprising SEQ ID NO: 87 and a light chain (LC) variable domain comprising SEQ ID NO: 90. In some cases, the anti-TL1A antibody comprises a heavy chain (HC) variable domain comprising SEQ ID NO: 87 and a light chain (LC) variable domain comprising SEQ ID NO: 91.

In some embodiments, the anti-TL1A antibody comprises a HCDR1 comprising SEQ ID NO: 92, a HCDR2 comprising SEQ ID NO: 93, a HCDR3 comprising SEQ ID NO: 94, a LCDR1 comprising SEQ ID NO: 95, a LCDR2 comprising SEQ ID NO: 96, and a LCDR3 comprising SEQ ID NO: 97. In some cases, the anti-TL1A antibody comprises a heavy chain (HC) variable domain comprising SEQ ID NO: 98 and a light chain (LC) variable domain comprising SEQ ID NO: 99. In some cases, the anti-TL1A antibody comprises a heavy chain (HC) variable domain comprising SEQ ID NO: 100 and a light chain (LC) variable domain comprising SEQ ID NO: 101. In some cases, the anti-TL1A antibody comprises a heavy chain (HC) variable domain comprising SEQ ID NO: 102 and a light chain (LC) variable domain comprising SEQ ID NO: 103. In some cases, the anti-TL1A antibody comprises a heavy chain (HC) variable domain comprising SEQ ID NO: 104 and a light chain (LC) variable domain comprising SEQ ID NO: 105. In some cases, the anti-TL1A antibody comprises a heavy chain (HC) variable domain comprising SEQ ID NO: 106 and a light chain (LC) variable domain comprising SEQ ID NO: 107. In some cases, the anti-TL1A antibody comprises a heavy chain (HC) variable domain comprising SEQ ID NO: 108 and a light chain (LC) variable domain comprising SEQ ID NO: 109. In some cases, the anti-TL1A antibody comprises a heavy chain (HC) variable domain comprising SEQ ID NO: 110 and a light chain (LC) variable domain comprising SEQ ID NO: 111. In some cases, the anti-TL1A antibody comprises a heavy chain (HC) variable domain comprising SEQ ID NO: 112 and a light chain (LC) variable domain comprising SEQ ID NO: 113. In some cases, the anti-TL1A antibody comprises a heavy chain (HC) variable domain comprising SEQ ID NO: 114 and a light chain (LC) variable domain comprising SEQ ID NO: 115. In some cases, the anti-TL1A antibody comprises a heavy chain (HC) variable domain comprising SEQ ID NO: 116 and a light chain (LC) variable domain comprising SEQ ID NO: 117. In some cases, the anti-TL1A antibody comprises a heavy chain (HC) variable domain comprising SEQ ID NO: 118 and a light chain (LC) variable domain comprising SEQ ID NO: 119. In some cases, the anti-TL1A antibody comprises a heavy chain (HC) variable domain comprising SEQ ID NO: 120 and a light chain (LC) variable domain comprising SEQ ID NO: 121.

In some embodiments, the anti-TL1A antibody comprises a HCDR1 comprising SEQ ID NO: 122, a HCDR2 comprising SEQ ID NO: 123, a HCDR3 comprising SEQ ID NO: 124, a LCDR1 comprising SEQ ID NO: 125, a LCDR2 comprising SEQ ID NO: 126, and a LCDR3 comprising SEQ ID NO: 127. In some cases, the anti-TL1A antibody comprises a heavy chain (HC) variable domain comprising SEQ ID NO: 128 and a light chain (LC) variable domain comprising SEQ ID NO: 129.

In some embodiments, the anti-TL1A antibody comprises a HCDR1 comprising SEQ ID NO: 130, a HCDR2 comprising SEQ ID NO: 131, a HCDR3 comprising SEQ ID NO: 132, a LCDR1 comprising SEQ ID NO: 133, a LCDR2 comprising SEQ ID NO: 134, and a LCDR3 comprising SEQ ID NO: 135. In some cases, the anti-TL1A antibody comprises a heavy chain (HC) variable domain comprising SEQ ID NO: 136 and a light chain (LC) variable domain comprising SEQ ID NO: 137.

In some embodiments, the anti-TL1A antibody comprises a HCDR1 comprising SEQ ID NO: 140, a HCDR2 comprising SEQ ID NO: 141, a HCDR3 comprising SEQ ID NO: 142, a LCDR1 comprising SEQ ID NO: 143, a LCDR2 comprising SEQ ID NO: 144, and a LCDR3 comprising SEQ ID NO: 145. In some cases, the anti-TL1A antibody comprises a heavy chain (HC) variable domain comprising SEQ ID NO: 138 and a light chain (LC) variable domain comprising SEQ ID NO: 139. In some cases, the anti-TL1A antibody comprises a heavy chain (HC) variable domain comprising SEQ ID NO: 146 and a light chain (LC) variable domain comprising SEQ ID NO: 147. In some cases, the anti-TL1A antibody comprises a heavy chain (HC) variable domain comprising SEQ ID NO: 148 and a light chain (LC) variable domain comprising SEQ ID NO: 149. In some cases, the anti-TL1A antibody comprises a heavy chain (HC) variable domain comprising SEQ ID NO: 150 and a light chain (LC) variable domain comprising SEQ ID NO: 151.

In some embodiments, the anti-TL1A antibody comprises a HCDR1 comprising SEQ ID NO: 170, a HCDR2 comprising SEQ ID NO: 171, a HCDR3 comprising SEQ ID NO: 172, a LCDR1 comprising SEQ ID NO: 173, a LCDR2 comprising SEQ ID NO: 174, and a LCDR3 comprising SEQ ID NO: 175. In some cases, the anti-TL1A antibody comprises a heavy chain (HC) variable domain comprising SEQ ID NO: 176 and a light chain (LC) variable domain comprising SEQ ID NO: 177.

In some embodiments, the anti-TL1A antibody comprises a HCDR1 comprising SEQ ID NO: 178, a HCDR2 comprising SEQ ID NO: 179, a HCDR3 comprising SEQ ID NO: 180, a LCDR1 comprising SEQ ID NO: 181, a LCDR2 comprising SEQ ID NO: 182, and a LCDR3 comprising SEQ ID NO: 183. In some cases, the anti-TL1A antibody comprises a heavy chain (HC) variable domain comprising SEQ ID NO: 184 and a light chain (LC) variable domain comprising SEQ ID NO: 185.

In some embodiments, the anti-TL1A antibody is A100. In some embodiments, the anti-TL1A antibody is A101. In some embodiments, the anti-TL1A antibody is A102. In some embodiments, the anti-TL1A antibody is A103. In some embodiments, the anti-TL1A antibody is A104. In some embodiments, the anti-TL1A antibody is A105. In some embodiments, the anti-TL1A antibody is A106. In some embodiments, the anti-TL1A antibody is A107. In some embodiments, the anti-TL1A antibody is A108. In some embodiments, the anti-TL1A antibody is A109. In some embodiments, the anti-TL1A antibody is A110. In some embodiments, the anti-TL1A antibody is A111. In some embodiments, the anti-TL1A antibody is A112. In some embodiments, the anti-TL1A antibody is A113. In some embodiments, the anti-TL1A antibody is A114. In some embodiments, the anti-TL1A antibody is A115. In some embodiments, the anti-TL1A antibody is A116. In some embodiments, the anti-TL1A antibody is A117. In some embodiments, the anti-TL1A antibody is A118. In some embodiments, the anti-TL1A antibody is A119. In some embodiments, the anti-TL1A antibody is A120. In some embodiments, the anti-TL1A antibody is A121. In some embodiments, the anti-TL1A antibody is A122. In some embodiments, the anti-TL1A antibody is A123. In some embodiments, the anti-TL1A antibody is A124. In some embodiments, the anti-TL1A antibody is A125. In some embodiments, the anti-TL1A antibody is A126. In some embodiments, the anti-TL1A antibody is A127. In some embodiments, the anti-TL1A antibody is A128. In some embodiments, the anti-TL1A antibody is A129. In some embodiments, the anti-TL1A antibody is A130. In some embodiments, the anti-TL1A antibody is A131. In some embodiments, the anti-TL1A antibody is A132. In some embodiments, the anti-TL1A antibody is A133. In some embodiments, the anti-TL1A antibody is A134. In some embodiments, the anti-TL1A antibody is A135. In some embodiments, the anti-TL1A antibody is A136. In some embodiments, the anti-TL1A antibody is A137. In some embodiments, the anti-TL1A antibody is A138. In some embodiments, the anti-TL1A antibody is A139. In some embodiments, the anti-TL1A antibody is A140. In some embodiments, the anti-TL1A antibody is A141. In some embodiments, the anti-TL1A antibody is A142. In some embodiments, the anti-TL1A antibody is A143. In some embodiments, the anti-TL1A antibody is A144. In some embodiments, the anti-TL1A antibody is A145. In some embodiments, the anti-TL1A antibody is A146. In some embodiments, the anti-TL1A antibody is A147. In some embodiments, the anti-TL1A antibody is A148. In some embodiments, the anti-TL1A antibody is A149. In some embodiments, the anti-TL1A antibody is A150. In some embodiments, the anti-TL1A antibody is A151. In some embodiments, the anti-TL1A antibody is A152. In some embodiments, the anti-TL1A antibody is A153. In some embodiments, the anti-TL1A antibody is A154. In some embodiments, the anti-TL1A antibody is A155. In some embodiments, the anti-TL1A antibody is A156. In some embodiments, the anti-TL1A antibody is A157. In some embodiments, the anti-TL1A antibody is A158. In some embodiments, the anti-TL1A antibody is A159. In some embodiments, the anti-TL1A antibody is A160. In some embodiments, the anti-TL1A antibody is A161. In some embodiments, the anti-TL1A antibody is A162. In some embodiments, the anti-TL1A antibody is A163. In some embodiments, the anti-TL1A antibody is A164. In some embodiments, the anti-TL1A antibody is A165. In some embodiments, the anti-TL1A antibody is A166. In some embodiments, the anti-TL1A antibody is A167. In some embodiments, the anti-TL1A antibody is A168. In some embodiments, the anti-TL1A antibody is A169. In some embodiments, the anti-TL1A antibody is A170. In some embodiments, the anti-TL1A antibody is A171. In some embodiments, the anti-TL1A antibody is A172. In some embodiments, the anti-TL1A antibody is A173. In some embodiments, the anti-TL1A antibody is A174. In some embodiments, the anti-TL1A antibody is A175. In some embodiments, the anti-TL1A antibody is A174. In some embodiments, the anti-TL1A antibody is A176. In some embodiments, the anti-TL1A antibody is A174. In some embodiments, the anti-TL1A antibody is A177.

In some embodiments, the anti-DR3 is A178. In some embodiments, the anti-DR3 is A179. In some embodiments, the anti-DR3 is A180. In some embodiments, the anti-DR3 is A181. In some embodiments, the anti-DR3 is A182. In some embodiments, the anti-DR3 is A183. In some embodiments, the anti-DR3 is A184. In some embodiments, the anti-DR3 is A185. In some embodiments, the anti-DR3 is A186. In some embodiments, the anti-DR3 is A187. In some embodiments, the anti-DR3 is A188. In some embodiments, the anti-DR3 is A189. In some embodiments, the anti-DR3 is A190. In some embodiments, the anti-DR3 is A191. In some embodiments, the anti-DR3 is A192. In some embodiments, the anti-DR3 is A193. In some embodiments, the anti-DR3 is A194. In some embodiments, the anti-DR3 is A195. In some embodiments, the anti-DR3 is A196. In some embodiments, the anti-DR3 is A197. In some embodiments, the anti-DR3 is A198. In some embodiments, the anti-DR3 is A199. In some embodiments, the anti-DR3 is A200. In some embodiments, the anti-DR3 is A201. In some embodiments, the anti-DR3 is A202. In some embodiments, the anti-DR3 is A203. In some embodiments, the anti-DR3 is A204. In some embodiments, the anti-DR3 is A205. In some embodiments, the anti-DR3 is A206. In some embodiments, the anti-DR3 is A207. In some embodiments, the anti-DR3 is A208. In some embodiments, the anti-DR3 is A209. In some embodiments, the anti-DR3 is A210. In some embodiments, the anti-DR3 is A211. In some embodiments, the anti-DR3 is A212. In some embodiments, the anti-DR3 is A213. In some embodiments, the anti-DR3 is A214. In some embodiments, the anti-DR3 is A215. In some embodiments, the anti-DR3 is A216. In some embodiments, the anti-DR3 is A217. In some embodiments, the anti-DR3 is A218. In some embodiments, the anti-DR3 is A219. In some embodiments, the anti-DR3 is A220. In some embodiments, the anti-DR3 is A221. In some embodiments, the anti-DR3 is A222. In some embodiments, the anti-DR3 is A223. In some embodiments, the anti-DR3 is A224. In some embodiments, the anti-DR3 is A225. In some embodiments, the anti-DR3 is A226. In some embodiments, the anti-DR3 is A227. In some embodiments, the anti-DR3 is A228. In some embodiments, the anti-DR3 is A229. In some embodiments, the anti-DR3 is A230. In some embodiments, the anti-DR3 is A231. In some embodiments, the anti-DR3 is A232. In some embodiments, the anti-DR3 is A233. In some embodiments, the anti-DR3 is A234. In some embodiments, the anti-DR3 is A235. In some embodiments, the anti-DR3 is A236. In some embodiments, the anti-DR3 is A237. In some embodiments, the anti-DR3 is A238. In some embodiments, the anti-DR3 is A239. In some embodiments, the anti-DR3 is A240. In some embodiments, the anti-DR3 is A241. In some embodiments, the anti-DR3 is A242.

In some cases, the anti-TL1A antibody binds to at least one or more of the same residues of human TL1A as an antibody described herein. For example, the anti-TL1A antibody binds to at least one or more of the same residues of human TL1A as an antibody selected from A100-A177. In some cases, the anti-TL1A antibody binds to the same epitope of human TL1A as an antibody selected from A100-A177. In some cases, the anti-TL1A antibody binds to the same region of human TL1A as an antibody selected from A100-A177. Non-limiting methods for determining whether an anti-TL1A antibody binds to the same region of a reference antibody are known in the art. An exemplary method comprises a competition assay. For instance, the method comprises determining whether a reference antibody can compete with binding between the reference antibody and the TL1A protein or portion thereof, or determining whether the reference antibody can compete with binding between the reference antibody and the TL1A protein or portion thereof. Exemplary methods include use of surface plasmon resonance to evaluate whether an anti-TL1A antibody can compete with the binding between TL1A and another anti-TL1A antibody. In some cases, surface plasmon resonance is utilized in the competition assay.

In some cases, the anti-CD30L antibody binds to at least one or more of the same residues of human CD30L as an antibody described herein. For example, the anti-CD30L antibody binds to at least one or more of the same residues of human CD30L as an antibody selected from A178-A242. In some cases, the anti-CD30L antibody binds to the same epitope of human CD30L as an antibody selected from A178-A242. In some cases, the anti-CD30L antibody binds to the same region of human CD30L as an antibody selected from A178-A242.

TABLE 1

Non-Limiting Examples of anti-TL1A or anti-DR3 Antibodies and Portions Thereof

| SEQ ID | Sequence |
|---|---|
| 3 | GFTFSTYG |
| 4 | ISGTGRTT |
| 5 | TKERGDYYYG VFDY |
| 6 | QTISSW |
| 7 | AAS |
| 8 | QQYHRSWT |
| 9 | EVQLLESGGG LVQPGKSLRL SCAVSGFTFS TYGMNWVRQA PGKGLEWVSS ISGTGRTTYH ADSVQGRFTV SRDNSKNILY LQMNSLRADD TAVYFCTKER GDYYYGVFDY WGQGTLVTVS S |
| 10 | DIQMTQSPST LSASVGDRVT ITCRASQTIS SWLAWYQQTP EKAPKLLIYA ASNLQSGVPS RFSGSGSGTE FTLTISSLQP DDFATYYCQQ YHRSWTFGQG TKVEIT |
| 11 | GFTFSSYW |
| 12 | IKEDGSEK |
| 13 | AREDYDSYYK YGMDV |
| 14 | QSILYSSNNK NY |
| 15 | WAS |
| 16 | QQYYSTPFT |
| 17 | EVQLVESGGG LVQPGGSLRL SCAVSGFTFS SYWMSWVRQA PGKGLEWVAN IKEDGSEKNY VDSVKGRFTL SSDNAKNSLY LQMNSLRAED TAVYYCARED YDSYYKYGMD VWGQGTAVIV SS |
| 18 | DIVMTQSPDS LAVSLGERAT INCKSSQSIL YSSNNKNYLA WYQQKPGQPP KLLIYWASTR ESGVPDRFSG SGSGTDFTLT ISSLQAEDVS VYYCQQYYST PFTFGPGTKV DIK |
| 19 | GGSFTGFY |
| 20 | INHRGNT |
| 21 | ASPFYDFWSG SDY |
| 22 | QSLVHSDGNT Y |
| 23 | KIS |
| 24 | MQATQFPLT |
| 25 | QVQLQQWGAG LLKPSETLSL TCAVYGGSFT GFYWSWIRQP PGKGLEWIGE INHRGNTNYN PSLKSRVTMS VDTSKNQFSL NMISVTAADT AMYFCASPFY DFWSGSDYWG QGTLVTVSS |
| 26 | DIMLTQTPLT SPVTLGQPAS ISCKSSQSLV HSDGNTYLSW LQQRPGQPPR LLFYKISNRF SGVPDRFSGS GAGTDFTLKI SRVEAEDVGV YYCMQATQFP LTFGGGTKVE IK |
| 27 | GY(X1)F(X2)(X3)YGIS; X1 = P, S, D, Q, N; X2 = T, R; X3 = N, T, Y, H |
| 28 | WIS(X1)YNG(X2)(X3)(X4)YA(X5)(X6)(X7)QG; X1 = T, P, S, A; X2 = N, G, V, K, A; X3 = T, K; X4 = H, N; X5 = Q, R; X6 = K, M; X7 = L, H |
| 29 | ENYYGSG(X1)(X2)R GGMD(X3); X1 = S, A; X2 = Y, P; X3 = V, A, G |
| 30 | GYDFTYYGIS |
| 31 | WISTYNGNTH YARMLQG |

TABLE 1-continued

Non-Limiting Examples of anti-TL1A or anti-DR3 Antibodies and Portions Thereof

| SEQ ID | Sequence |
|---|---|
| 32 | ENYYGSGAYR GGMDV |
| 33 | RASQSVSSYL A |
| 34 | DASNRAT |
| 35 | QQRSNWPWT |
| 36 | QVQLVQSGAE VKKPGASVKV SCKASGYDFT YYGISWVRQA PGQGLEWMGW ISTYNGNTHY ARMLQGRVTM TTDTSTRTAY MELRSLRSDD TAVYYCAREN YYGSGAYRGG MDVWGQGTTV TVSS |
| 37 | EIVLTQSPAT LSLSPGERAT LSCRASQSVS SYLAWYQQKP GQAPRLLIYD ASNRATGIPA RFSGSGSGTD FTLTISSLEP EDFAVYYCQQ RSNWPWTFGQ GTKVEIK |
| 38 | QVQLVQSGAE VKKPGASVKV SCKASGYDFT YYGISWVRQA PGQGLEWMGW ISTYNGNTHY ARMLQGRVTM TTDTSTRTAY MELRSLRSDD TAVYYCAREN YYGSGAYRGG MDVWGQGTTV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK KVEPKSCDKT HTCPPCPAPE AAGAPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPG |
| 39 | EIVLTQSPAT LSLSPGERAT LSCRASQSVS SYLAWYQQKP GQAPRLLIYD ASNRATGIPA RFSGSGSGTD FTLTISSLEP EDFAVYYCQQ RSNWPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 40 | SRSYYWG |
| 41 | SIYYNGRTYY NPSLKS |
| 42 | EDYGDYGAFD I |
| 43 | RASQGISSAL A |
| 44 | DASSLES |
| 45 | QQFNSYPLT |
| 46 | QLQLQESGPG LVKPSETLSL TCTVSGGSIS SRSYYWGWIR QPPGKGLEWI GSIYYNGRTY YNPSLKSRVT ISVDTSKNQF SLKLSSVTAA DTAVYYCARE DYGDYGAFDI WGQGTMVTVS S |
| 47 | AIQLTQSPSS LSASVGDRVT ITCRASQGIS SALAWYQQKP GKAPKLLIYD ASSLESGVPS RFSGSGSGTD FTLTISSLQP EDFATYYCQQ FNSYPLTFGG GTKVEIK |
| 48 | TSNMGVV |
| 49 | HILWDDREYSNPALKS |
| 50 | MSRNYYGSSYVMDY |
| 51 | SASSSVNYMH |
| 52 | STSNLAS |
| 53 | HQWNNYGT |
| 54 | QVTLKESGPALVKPTQTLTLTCTFSGFSLSTSNMGVVWIRQPPGKALEWLAHILWDD REYSNPALKSRLTISKDTSKNQVVLTMTNMDPVDTATYYCARMSRNYYGSSYVMD YWGQGTLVTVSS |
| 55 | DIQLTQSPSFLSASVGDRVTITCSASSSVNYMHWYQQKPGKAPKLLIYSTSNLASGVP SRFSGSGSGTEFTLTISSLQPEDFATYYCHQWNNYGTFGQGTKVEIKR |
| 56 | LYGMN |

TABLE 1-continued

Non-Limiting Examples of anti-TL1A or anti-DR3 Antibodies and Portions Thereof

| SEQ ID | Sequence |
|---|---|
| 57 | NYGMN |
| 58 | WINTYTGEPTYADDFKG |
| 59 | DTAMDYAMAY |
| 60 | DYGKYGDYYAMDY |
| 61 | KSSQNIVHSDGNTYLE |
| 62 | RSSQSIVHSNGNTYLD |
| 63 | KVSNRFS |
| 64 | FQGSHVPLT |
| 65 | QVQLVQSGSELKKPGASVKVSCKASGYTFTLYGMNWVRQAPGQGLEWMG WINTYTGEPTYADDFKGRFVFSLDTSVSTAYLQISSLKAEDTAVYYCAR DTAMDYAMAYWGQGTLVTVSS |
| 66 | QVQLVQSGSELKKPGASVKVSCKASGYTFTLYGMNWVKQAPGKGLKWMG WINTYTGEPTYADDFKGRFVFSLDTSVSTAYLQISSLKAEDTAVYFCAR DTAMDYAMAYWGQGTLVTVSS |
| 67 | QVQLVQSGSELKKPGASVKVSCKASGYTFTNYGMNWVRQAPGQGLEWMG WINTYTGEPTYADDFKGRFVFSLDTSVSTAYLQISSLKAEDTAVYYCAR DYGKYGDYYAMDYWGQGTLVTVSS |
| 68 | QVQLVQSGSELKKPGASVKVSCKASGYTFTNYGMNWVRQAPGKGLKWMG WINTYTGEPTYADDFKGRFVFSLDTSVSTAYLQISSLKAEDTAVYFCAR DYGKYGDYYAMDYWGQGTLVTVSS |
| 69 | DVVMTQSPLSLPVTLGQPASISCKSSQNIVHSDGNTYLEWFQQRPGQSP RRLIYKVSNRFSGVPDRFSGSGSGTDFTLKISRVEAEDVGVYYCFQGSH VPLTFGGGTKVEIKR |
| 70 | DVVMTQSPLSLPVTLGQPASISCKSSQNIVHSDGNTYLEWFQQRPGQSP RRLIYKVSNRFSGVPDRFSGSGSGTDFTLKISRVEAEDVGVYYCFQGSH VPLTFGQGTKVEIKR |
| 71 | DVVMTQTPLSLPVTPGEPASISCKSSQNIVHSDGNTYLEWYLQKPGQSP QLLIYKVSNRFSGVPDRFSGSGSGTDFTLKISRVEAEDLGVYYCFQGSH VPLTFGGGTKVEIKR |
| 72 | DVVMTQTPLSLPVSLGDQASISCKSSQNIVHSDGNTYLEWYLQKPGQSP KVLIYKVSNRFSGVPDRFSGSGSGTDFTLKISRVEAEDLGVYYCFQGSH VPLTFGGGTKVEIKR |
| 73 | DVVMTQSPLSLPVTLGQPASISCRSSQSIVHSNGNTYLDWFQQRPGQSP RRLIYKVSNRFSGVPDRFSGSGSGTDFTLKISRVEAEDVGVYYCFQGSH VPLTFGGGTKVEIKR |
| 74 | DVVMTQSPLSLPVTLGQPASISCRSSQSIVHSNGNTYLDWFQQRPGQSP RRLIYKVSNRFSGVPDRFSGSGSGTDFTLKISRVEAEDVGVYYCFQGSH VPLTFGQGTKVEIKR |
| 75 | DVVMTQTPLSLPVTPGEPASISCRSSQSIVHSNGNTYLDWYLQKPGQSP QLLIYKVSNRFSGVPDRFSGSGSGTDFTLKISRVEAEDLGVYYCFQGSH VPLTFGGGTKVEIKR |
| 76 | DVVMTQTPLSLPVSLGDQASISCRSSQSIVHSNGNTYLDWYLQKPGQSP KVLIYKVSNRFSGVPDRFSGSGSGTDFTLKINRVEAEDLGVYFCFQGSH VPLTFGGGTKLEIKR |
| 77 | GYTFTSSWMH |
| 78 | IHPNSGGT |
| 79 | ARGDYYGYVS WFAY |
| 80 | QNINVL |
| 81 | KAS |

TABLE 1-continued

Non-Limiting Examples of anti-TL1A or anti-DR3 Antibodies and Portions Thereof

| SEQ ID | Sequence |
|---|---|

82 QQGQSYPYT

83 QVQLQQPGSV LVRPGASVKV SCKASGYTFT SSWMHWAKQR PGQGLEWIGE
   IHPNSGGTNY NEKFKGKATV DTSSSTAYVD LSSLTSEDSA VYYCARGDYY
   GYVSWFAYWG QGTLVTVSS

84 QVQLVQSGAE VKKPGASVKV SCKASGYTFT SSWMHWARQA PGQGLEWIGE
   IHPNSGGTNY AQKFQGRATL TVDTSSSTAY MELSRLRSDD TAVYYCARGD
   YYGYVSWFAY WGQGTLVTVS S

85 QVQLVQSGAE VKKPGASVKV SCKASGYTFT SSWMHWARQA PGQGLEWIGE
   IHPNSGGTNY AQKFQGRATM TVDTSISTAY MELSRLRSDD TAVYYCARGD
   YYGYVSWFAY WGQGTLVTVS S

86 QVQLVQSGAE VKKPGASVKV SCKASGYTFT SSWMHWARQA PGQGLEWIGE
   IHPNSGGTNY AQKFQGRVTM TVDTSISTAY MELSRLRSDD TAVYYCARGD
   YYGYVSWFAY WGQGTLVTVS S

87 QVQLVQSGAE VKKPGASVKV SCKASGYTFT SSWMHWARQA PGQGLEWMGE
   IHPNSGGTNY AQKFQGRVTM TVDTSISTAY MELSRLRSDD TAVYYCARGD
   YYGYVSWFAY WGQGTLVTVS S

88 DIQMNQSPSS LSASLGDTIT ITCHASQNIN VLLSWYQQKP GNIPKLLIYK
   ASNLHTGVPS RFSGSGSGTG FTFTISSLQP EDIATYYCQQ GQSYPYTFGG
   GTKLEIK

89 DIQMTQSPSS LSASVGDRVT ITCQASQDIS NYLNWYQQKP GKAPKLLIYD
   ASNLETGVPS RFSGSGSGTD FTFTISSLQP EDIATYYCQQ YDNLPYTFGQ
   GTKLEIK

90 DIQMTQSPSS LSASVGDRVT ITCQASQNIN VLLNWYQQKP GKAPKLLIYK
   ASNLHTGVPS RFSGSGSGTD FTFTISSLQP EDIATYYCQQ GQSYPYTFGQ
   GTKLEIK

91 DIQMNQSPSS LSASVGDRVT ITCQASQNIN VLLSWYQQKP GKAPKLLIYK
   ASNLHTGVPS RFSGSGSGTD FTFTISSLQP EDIATYYCQQ GQSYPYTFGQ
   GTKLEIK

92 GYTFTSYDIN

93 WLNPNSGXTG; X = N, Y

94 EVPETAAFEY

95 TSSSSDIGA(X1) (X2)GV(X3); X1 = G, A; X2 = L, S, Q;
   X3 = H, L

96 GYYNRPS

97 QSXDGTLSAL; X = Y, W, F

98 QVQLVQSGAE VKKPGASVKV SCKASGYTFT SYDINWVRQA PGQGLEWMGW
   LNPNSGNTGY AQKFQGRVTM TADRSTSTAY MELSSLRSED TAVYYCAREV
   PETAAFEYWG QGTLVTVSS

99 QSVLTQPPSV SGAPGQRVTI SCTSSSSDIG AXXGVXWYQQ LPGTAPKLLI
   EGYYNRPSGV PDRFSGSKSG TSASLTITGL LPEDEGDYYC QSXDGTLSAL
   FGGGTKLTVL G

100 QVQLVQSGAE VKKPGASVKV SCKASGYTFT SYDINWVRQA PGQGLEWMGW
    LNPNSGNTGY AQKFQGRVTM TADRSTSTAY MELSSLRSED TAVYYCAREV
    PETAAFEYWG QGTLVTVSS

101 QSVLTQPPSV SGAPGQRVTI SCTSSSSDIG AGLGVHWYQQ LPGTAPKLLI
    EGYYNRPSGV PDRFSGSKSG TSASLTITGL LPEDEGDYYC QSWDGTLSAL
    FGGGTKLTVL G

102 QVQLVQSGAE VKKPGASVKV SCKASGYTFT SYDINWVRQA PGQGLEWMGW
    LNPNSGYTGY AQKFQGRVTM TADRSTSTAY MELSSLRSED TAVYYCAREV
    PETAAFEYWG QGTLVTVSS

103 QSVLTQPPSV SGAPGQRVTI SCTSSSSDIG AGLGVHWYQQ LPGTAPKLLI
    EGYYNRPSGV PDRFSGSKSG TSASLTITGL LPEDEGDYYC QSYDGTLSAL
    FGGGTKLTVL G

TABLE 1-continued

Non-Limiting Examples of anti-TL1A or anti-DR3 Antibodies and Portions Thereof

| SEQ ID | Sequence |
|---|---|

104 QVQLVQSGAE VKKPGASVKV SCKASGYTFT SYDINWVRQA PGQGLEWMGW
    LNPNSGNTGY AQKFQGRVTM TADRSTSTAY MELSSLRSED TAVYYCAREV
    PETAAFEYWG QGTLVTVSS

105 QSVLTQPPSV SGAPGQRVTI SCTSSSSDIG AALGVHWYQQ LPGTAPKLLI
    EGYYNRPSGV PDRFSGSKSG TSASLTITGL LPEDEGDYYC QSWDGTLSAL
    FGGGTKLTVL G

106 QVQLVQSGAE VKKPGASVKV SCKASGYTFT SYDINWVRQA PGQGLEWMGW
    LNPNSGNTGY AQKFQGRVTM TADRSTSTAY MELSSLRSED TAVYYCAREV
    PETAAFEYWG QGTLVTVSS

107 QSVLTQPPSV SGAPGQRVTI SCTSSSSDIG AGSGVHWYQQ LPGTAPKLLI
    EGYYNRPSGV PDRFSGSKSG TSASLTITGL LPEDEGDYYC QSWDGTLSAL
    FGGGTKLTVL G

108 QVQLVQSGAE VKKPGASVKV SCKASGYTFT SYDINWVRQA PGQGLEWMGW
    LNPNSGNTGY AQKFQGRVTM TADRSTSTAY MELSSLRSED TAVYYCAREV
    PETAAFEYWG QGTLVTVSS

109 QSVLTQPPSV SGAPGQRVTI SCTSSSSDIG AGQGVHWYQQ LPGTAPKLLI
    EGYYNRPSGV PDRFSGSKSG TSASLTITGL LPEDEGDYYC QSWDGTLSAL
    FGGGTKLTVL G

110 QVQLVQSGAE VKKPGASVKV SCKASGYTFT SYDINWVRQA PGQGLEWMGW
    LNPNSGNTGY AQKFQGRVTM TADRSTSTAY MELSSLRSED TAVYYCAREV
    PETAAFEYWG QGTLVTVSS

111 QSVLTQPPSV SGAPGQRVTI SCTSSSSDIG AGLGVLWYQQ LPGTAPKLLI
    EGYYNRPSGV PDRFSGSKSG TSASLTITGL LPEDEGDYYC QSWDGTLSAL
    FGGGTKLTVL G

112 QVQLVQSGAE VKKPGASVKV SCKASGYTFT SYDINWVRQA PGQGLEWMGW
    LNPNSGYTGY AQKFQGRVTM TADRSTSTAY MELSSLRSED TAVYYCAREV
    PETAAFEYWG QGTLVTVSS

113 QSVLTQPPSV SGAPGQRVTI SCTSSSSDIG AGLGVHWYQQ LPGTAPKLLI
    EGYYNRPSGV PDRFSGSKSG TSASLTITGL LPEDEGDYYC QSWDGTLSAL
    FGGGTKLTVL G

114 QVQLVQSGAE VKKPGASVKV SCKASGYTFT SYDINWVRQA PGQGLEWMGW
    LNPNSGYTGY AQKFQGRVTM TADRSTSTAY MELSSLRSED TAVYYCAREV
    PETAAFEYWG QGTLVTVSS

115 QSVLTQPPSV SGAPGQRVTI SCTSSSSDIG AGSGVHWYQQ LPGTAPKLLI
    EGYYNRPSGV PDRFSGSKSG TSASLTITGL LPEDEGDYYC QSWDGTLSAL
    FGGGTKLTVL G

116 QVQLVQSGAE VKKPGASVKV SCKASGYTFT SYDINWVRQA PGQGLEWMGW
    LNPNSGYTGY AQKFQGRVTM TADRSTSTAY MELSSLRSED TAVYYCAREV
    PETAAFEYWG QGTLVTVSS

117 QSVLTQPPSV SGAPGQRVTI SCTSSSSDIG AGQGVHWYQQ LPGTAPKLLI
    EGYYNRPSGV PDRFSGSKSG TSASLTITGL LPEDEGDYYC QSWDGTLSAL
    FGGGTKLTVL G

118 QVQLVQSGAE VKKPGASVKV SCKASGYTFT SYDINWVRQA PGQGLEWMGW
    LNPNSGYTGY AQKFQGRVTM TADRSTSTAY MELSSLRSED TAVYYCAREV
    PETAAFEYWG QGTLVTVSS

119 QSVLTQPPSV SGAPGQRVTI SCTSSSSDIG AGLGVLWYQQ LPGTAPKLLI
    EGYYNRPSGV PDRFSGSKSG TSASLTITGL LPEDEGDYYC QSWDGTLSAL
    FGGGTKLTVL G

120 QVQLVQSGAE VKKPGASVKV SCKASGYTFT SYDINWVRQA PGQGLEWMGW
    LNPNSGYTGY AQKFQGRVTM TADRSTSTAY MELSSLRSED TAVYYCAREV
    PETAAFEYWG QGTLVTVSS

121 QSVLTQPPSV SGAPGQRVTI SCTSSSSDIG AGLGVHWYQQ LPGTAPKLLI
    EGYYNRPSGV PDRFSGSKSG TSASLTITGL LPEDEGDYYC QSFDGTLSAL
    FGGGTKLTVL G

122 SYFWS

TABLE 1-continued

Non-Limiting Examples of anti-TL1A or anti-DR3 Antibodies and Portions Thereof

| SEQ ID | Sequence |
|---|---|
| 123 | YIYYSGNTKYNPSLKS |
| 124 | ETGSYYGFDY |
| 125 | RASQSINNYLN |
| 126 | AASSLQS |
| 127 | QQSYSTPRT |
| 128 | QVQLQESGPGLVKPSETLSLTCTVSGGSISSYFWSWIRQPPGKGLEWIGYIYYSGNTKYNPSLKSRVTISIDTSKNQFSLKLSSVTAADTAVYYCARETGSYYGFDYWGQGTLVTVSS |
| 129 | DIQMTQSPSSLSASVGDRVTITCRASQSINNYLNWYQQRPGKAPKLLIYAASSLQSGVPSRFSGSGSGTDFTLTISSLQPGDFATYYCQQSYSTPRTFGQGTKLEIK |
| 130 | GYYWN |
| 131 | EINHAGNTNYNPSLKS |
| 132 | GYCRSTTCYFDY |
| 133 | RASQSVRSSYLA |
| 134 | GASSRAT |
| 135 | QQYGSSPT |
| 136 | QVQLQQWGAGLLKPSETLSLTCAVHGGSFSGYYWNWIRQPPGKGLEWIGEINHAGNTNYNPSLKSRVTISLDTSKNQFSLTLTSVTAADTAVYYCARGYCRSTTCYFDYWGQGTLVTVSS |
| 137 | EIVLTQSPGTLSLSPGERATLSCRASQSVRSSYLAWYQQKPGQAPRLLIYGASSRATGIPDRFSGSGSGTDFTLTISRLEPEDFAVYYCQQYGSSPTFGQGTRLEIK |
| 138 | EVQLQQSGAELVKPGASVKLSCTASGFDIQDTYMHWVKQRPEQGLEWIGRIDPASGHTKYDPKFQVKATITTDTSSNTAYLQLSSLTSEDTAVYYCSRSGGLPDVWGAGTTVTVSS |
| 139 | QIVLSQSPAILSASPGEKVTMTCRASSSVSYMYWYQQKPGSSPKPWIYATSNLASGVPDRFSGSGSGTSYSLTISRVEAEDAATYYCQQWSGNPRTFGGGTKLEIK |
| 140 | GFDIQDTYMH |
| 141 | RIDPASGHTKYDPKFQV |
| 142 | SGGLPDV |
| 143 | RASSSVSYMY |
| 144 | ATSNLAS |
| 145 | QQWSGNPRT |
| 146 | QVQLVQSGAEVKKPGASVKLSCKASGFDIQDTYMHWVRQAPGQGLEWMGRIDPASGHTKYDPKFQVRVTMTTDTSTSTVYMELSSLRSEDTAVYYCSRSGGLPDVWGQGTTVTVSS |
| 147 | EIVLTQSPGTLSLSPGERVTMSCRASSSVSYMYWYQQKPGQAPRPWIYATSNLASGVPDRFSGSGSGTDYTLTISRLEPEDFAVYYCQQWSGNPRTFGGGTKLEIK |
| 148 | QVQLVQSGAEVKKPGASVKLSCKASGFDIQDTYMHWVRQAPGQGLEWMGRIDPASGHTKYDPKFQVRVTMTRDTSTSTVYMELSSLRSEDTAVYYCSRSGGLPDVWGQGTTVTVSS |
| 149 | EIVLTQSPGTLSLSPGERATLSCRASSSVSYMYWYQQKPGQAPRLLIYATSNLASGIPDRFSGSGSGTDFTLTISRLEPEDFAVYYCQQWSGNPRTFGGGTKLEIK |
| 150 | QVQLVQSGAEVKKPGASVKVSCKASGFDIQDTYMHWVRQAPGQGLEWMGRIDPASGHTKYDPKFQVRVTMTRDTSTSTVYMELSSLRSEDTAVYYCARSGGLPDVWGQGTTVTVSS |

TABLE 1-continued

Non-Limiting Examples of anti-TL1A or anti-DR3 Antibodies and Portions Thereof

| SEQ ID | Sequence |
|---|---|
| 151 | EIVLTQSPGTLSLSPGERATLSCRASSSVSYMYWYQQKPGQAPRLLIYATSNLASGVPD RFSGSGSGTDYTLTISRLEPEDFAVYYCQQWSGNPRTFGGGTKLEIK |
| 152 | EVMLVESGGGLVKPGGSLKLSCAASGFTFTNYAMSWVRQTPEKRLEWVATITSGGSY IYYLDSVKGRFTISRDNAKSTLYLQMSSLRSEDTAIYNCARRKDGNYYYAMDYWGQG TSVTVSS |
| 153 | EVMLVESGGGLVKPGGSLKLSCAMGFTFTNYAMSWVRQTPEKRLEWVATITSGGSY IYYLDSVKGRFTISRDNAKSTLYLQMSSLRSEDTAIYYCARRKDGNYYYAMDYWGQG TSVTVSS |
| 154 | EVQLVESGGGLVKPGGSLRLSCAASGFTFTNYAMSWVRQAPGQRLEWVSTITSGGSYI YYLDSVKGRFTISRDNAKSTLYLQMNSLRAEDTAVYNCARRKDGNYYYAMDYWGQ GTTVTVSS |
| 155 | EVQLVESGGGLVKPGGSLRLSCAASGFTFTNYAMSWVRQAPGQRLEWVSTITSGGSYI YYLDSVKGRFTISRDNAKSTLYLQMNSLRAEDTAVYYCARRKDGNYYYAMDYWGQ GTTVTVSS |
| 156 | EVQLLESGGGLVQPGRSLRLSCAASGFTFTNYAMSWVRQAPGQRLEWLATITSGGSYI YYLDSVKGRFTISRDNSKSTLYLQMGSLRAEDMAVYNCARRKDGNYYYAMDYWGQ GTTVTVSS |
| 157 | EVQLLESGGGLVQPGRSLRLSCAASGFTFTNYAMSWVRQAPGQRLEWLATITSGGSYI YYLDSVKGRFTISRDNSKSTLYLQMGSLRAEDMAVYYCARRKDGNYYYAMDYWGQ GTTVTVSS |
| 158 | QVQLVESGGGLIQPGGSLRLSCAASGFTFTNYAMSWVRQARGQRLEWVSTITSGGSYI YYLDSVKGRFTISRDNSKSTLYMELSSLRSEDTAVYNCARRKDGNYYYAMDYWGQG TTVTVSS |
| 159 | QVQLVESGGGLIQPGGSLRLSCAASGFTFTNYAMSWVRQARGQRLEWVSTITSGGSYI YYLDSVKGRFTISRDNSKSTLYMELSSLRSEDTAVYYCARRKDGNYYYAMDYWGQG TTVTVSS |
| 160 | QVQLVQSGSELKKPGASVKVSCKASGFTFTNYAMSWVRQAPGKRLEWVSTITSGGSY IYYLDSVKGRFTISRENAKSTLYLQMNSLRTEDTALYNCARRKDGNYYYAMDYWGQ GTTVTVSS |
| 161 | QVQLVQSGSELKKPGASVKVSCKASGFTFTNYAMSWVRQAPGKRLEWVATITSGGSY IYYLDSVKGRFTISRENAKSTLYLQMNSLRTEDTALYYCARRKDGNYYYAMDYWGQ GTTVTVSS |
| 162 | EVQLLQSGAEVKKPGASVKVSCKASGFTFTNYAMSWVRQAPGQRLEWVATITSGGSY IYYLDSVKGRFTISRDNAKSTLHLQMNSLRAEDTAVYNCARRKDGNYYYAMDYWGQ GTTVTVSS |
| 163 | EVQLLQSGAEVKKPGASVKVSCKASGFTFTNYAMSWVRQAPGQRLEWVATITSGGSY IYYLDSVKGRFTISRDNAKSTLHLQMNSLRAEDTAIYYCARRKDGNYYYAMDYWGQ GTTVTVSS |
| 164 | EVMLLQSGAEVKKPGASVKVSCKASGFTFTNYAMSWVRQAPGQRLEWVATITSGGS YIYYLDSVKGRFTISRDNAKSTLHLQMNSLRAEDTAVYYCARRKDGNYYYAMDYWG QGTTVTVSS |
| 165 | DIVLTQSPASLAVSLGQRATISCRASESVDSYGNSFIHWYQQKAGQPPKLLIYRASNLE SGIPARFSGSGSRTDFTLTINPVEADDVATYYCQQSYEDPWTFGGGTKLEIK |
| 166 | DIVLTQSPATLSLSPGERATLSCRASESVDSYGNSFIHWYQQKPGQPPKLLIYRASNLES GIPARFSGSGSRTDFTLTISSLEPEDFAVYYCQQSYEDPWTFGGGTKXEIK |
| 167 | DIVLTQSPSSLSASVGDRVTITCRASESVDSYGNSFIHWYQQKPGQPPKLLIYRASNLES GIPARFSGSGSRTDFTLTISSLQPEDFATYYCQQSYEDPWTFGGGTKXEIK |
| 168 | DIVLTQSPDFQSVTPKEKVTITCRASESVDSYGNSFIHWYQQKPGQPPKLLIYRASNLES GIPARFSGSGSRTDFTLTISSLEAEDAATYYCQQSYEDPWTFGGGTKXEIK |
| 169 | DIVLTQTPLSLSVTPGQPASISCRASESVDSYGNSFIHWYQQKPGQPPKLLIYRASNLES GIPARFSGSGSRTDFTLKISRVEAEDVGVYYCQQSYEDPWTFGGGTKXEIK |
| 170 | TYGMS |
| 171 | WMNTYSGVTTYADDFKG |

TABLE 1-continued

Non-Limiting Examples of anti-TL1A or anti-DR3 Antibodies and Portions Thereof

| SEQ ID | Sequence |
|---|---|
| 172 | EGYVFDDYYATDY |
| 173 | RSSQNIVHSDGNTYLE |
| 174 | KVSNRFS |
| 175 | FQGSHVPLT |
| 176 | QIQLVQSGPELKKPGETVKISCKASGYTFTTYGMSWVKQAPGKGLKWMGWMNTYSGVTTYADDFKGRFAFSLETSASTAYMQIDNLKNEDTATYFCAREGYVFDDYYATDYWGQGTSVTVSS |
| 177 | DVLMTQTPLSLPVSLGDQASISCRSSQNIVHSDGNTYLEWYLQKPGQSPKLLIYKVSNRFSGVPDRFSGSGSGTDFTLKISRVEAEDLGIYYCFQGSHVPLTFGAGTKLELK |
| 178 | KYDIN |
| 179 | WIFPGDGRTDYNEKFKG |
| 180 | YGPAMDY |
| 181 | RSSQTIVHSNGDTYLD |
| 182 | KVSNRFS |
| 183 | FQGSHVPYT |
| 184 | MGWSWVFLFLLSVTAGVHSQVHLQQSGPELVKPGASVKLSCKASGYTFTKYDINWVRQRPEQGLEWIGWIFPGDGRTDYNEKFKGKATLTTDKSSSTAYMEVSRLTSEDSAVYFCARYGPAMDYWGQGTSVTVAS |
| 185 | MKLPVRLLVLMFWIPASSSDVLMTQTPLSLPVSLGDQASISCRSSQTIVHSNGDTYLDWFLQKPGQSPKLLIYKVSNRFSGVPDRFSGSGSGTDFTLKISRVEAEDLGVYYCFQGSHVPYTFGGGTKLEIK |

TABLE 2

Non-Limiting Examples of anti-TL1A and anti-DR3 Antibodies

| Antibody Name | HC Variable Domain (SEQ ID NO) | LC Variable Domain (SEQ ID NO) |
|---|---|---|
| A100 | 9 | 10 |
| A101 | 17 | 18 |
| A102 | 25 | 26 |
| A103 | 36 | 37 |
| A104 | 46 | 47 |
| A105 | 54 | 55 |
| A106 | 65 | 69 |
| A107 | 65 | 70 |
| A108 | 65 | 71 |
| A109 | 65 | 72 |
| A110 | 65 | 73 |
| A111 | 65 | 74 |
| A112 | 65 | 75 |
| A113 | 65 | 76 |
| A114 | 66 | 69 |
| A115 | 66 | 70 |
| A116 | 66 | 71 |
| A117 | 66 | 72 |
| A118 | 66 | 73 |
| A119 | 66 | 74 |
| A120 | 66 | 75 |
| A121 | 66 | 76 |
| A122 | 67 | 69 |
| A123 | 67 | 70 |
| A124 | 67 | 71 |
| A125 | 67 | 72 |
| A126 | 67 | 73 |
| A127 | 67 | 74 |
| A128 | 67 | 75 |
| A129 | 67 | 76 |
| A130 | 68 | 69 |
| A131 | 68 | 70 |
| A132 | 68 | 71 |
| A133 | 68 | 72 |
| A134 | 68 | 73 |
| A135 | 68 | 74 |
| A136 | 68 | 75 |
| A137 | 68 | 76 |
| A138 | 83 | 88 |
| A139 | 83 | 89 |
| A140 | 83 | 90 |
| A141 | 83 | 91 |
| A142 | 84 | 88 |
| A143 | 84 | 89 |
| A144 | 84 | 90 |
| A145 | 84 | 91 |
| A146 | 85 | 88 |
| A147 | 85 | 89 |
| A148 | 85 | 90 |
| A149 | 85 | 91 |
| A150 | 86 | 88 |
| A151 | 86 | 89 |
| A152 | 86 | 90 |
| A153 | 86 | 91 |
| A154 | 87 | 88 |
| A155 | 87 | 89 |
| A156 | 87 | 90 |
| A157 | 87 | 91 |

TABLE 2-continued

Non-Limiting Examples of anti-TL1A and anti-DR3 Antibodies

| Antibody Name | HC Variable Domain (SEQ ID NO) | LC Variable Domain (SEQ ID NO) |
|---|---|---|
| A158 | 98 | 99 |
| A159 | 100 | 101 |
| A160 | 102 | 103 |
| A161 | 104 | 105 |
| A162 | 106 | 107 |
| A163 | 108 | 109 |
| A164 | 110 | 111 |
| A165 | 112 | 113 |
| A166 | 114 | 115 |
| A167 | 116 | 117 |
| A168 | 118 | 119 |
| A169 | 120 | 121 |
| A170 | 128 | 129 |
| A171 | 136 | 137 |
| A172 | 138 | 139 |
| A173 | 146 | 147 |
| A174 | 148 | 149 |
| A175 | 150 | 151 |
| A176 | 176 | 177 |
| A177 | 184 | 185 |
| A178 | 152 | 165 |
| A179 | 152 | 166 |
| A180 | 152 | 167 |
| A181 | 152 | 168 |
| A182 | 152 | 169 |
| A183 | 153 | 165 |
| A184 | 153 | 166 |
| A185 | 153 | 167 |
| A186 | 153 | 168 |
| A187 | 153 | 169 |
| A188 | 154 | 165 |
| A189 | 154 | 166 |
| A190 | 154 | 167 |
| A191 | 154 | 168 |
| A192 | 154 | 169 |
| A193 | 155 | 165 |
| A194 | 155 | 166 |
| A195 | 155 | 167 |
| A196 | 155 | 168 |
| A197 | 155 | 169 |
| A198 | 156 | 165 |
| A199 | 156 | 166 |
| A200 | 156 | 167 |
| A201 | 156 | 168 |
| A202 | 156 | 169 |
| A203 | 157 | 165 |
| A204 | 157 | 166 |
| A205 | 157 | 167 |
| A206 | 157 | 168 |
| A207 | 157 | 169 |
| A208 | 158 | 165 |
| A209 | 158 | 166 |
| A210 | 158 | 167 |
| A211 | 158 | 168 |
| A212 | 158 | 169 |
| A213 | 159 | 165 |
| A214 | 159 | 166 |
| A215 | 159 | 167 |
| A216 | 159 | 168 |
| A217 | 159 | 169 |
| A218 | 160 | 165 |
| A219 | 160 | 166 |
| A220 | 160 | 167 |
| A221 | 160 | 168 |
| A222 | 160 | 169 |
| A223 | 161 | 165 |
| A224 | 161 | 166 |
| A225 | 161 | 167 |
| A226 | 161 | 168 |
| A227 | 161 | 169 |
| A228 | 162 | 165 |
| A229 | 162 | 166 |
| A230 | 162 | 167 |
| A231 | 162 | 168 |
| A232 | 162 | 169 |
| A233 | 163 | 165 |
| A234 | 163 | 166 |
| A235 | 163 | 167 |
| A236 | 163 | 168 |
| A237 | 163 | 169 |
| A238 | 164 | 165 |
| A239 | 164 | 166 |
| A240 | 164 | 167 |
| A241 | 164 | 168 |
| A242 | 164 | 169 |

Methods disclosed herein may comprise administering any one of the disclosed therapeutic agents alone. In other embodiments, methods disclosed herein may comprise administering any of the disclosed therapeutic agents in combination with another therapeutic agent disclosed herein, a nutritional-based therapy, a nature-based therapy, a diet-based therapy, or a combination thereof. A non-limiting example of a nature-based therapy includes microbial-based treatments such as probiotics.

Single Nucleotide Polymorphisms (SNPs) Associated with Non-Response to Anti-TNF Therapy In one aspect, provided herein, a single nucleotide polymorphism (SNP) is detected in a biological sample obtained from the subject. The SNP may be located at a gene locus involved in the mammalian innate and adaptive immune responses. In some embodiments, the gene locus is involved in the pathogenesis of IBD. In further embodiments, the gene locus is involved in autophagy and/or apoptosis. In some embodiments, the gene locus is in the major histocompatibility system, HLA. The gene locus may comprise TNFRSF1B, or HLA-DRB6, or a combination thereof.

In aspect, provided herein, a SNP at the TNFRSF1B gene locus comprising a risk allele, "C" at nucleobase 256 within rs5745994 (SEQ ID NO:1), a portion of which is shown in Table 3, or any polymorphism in linkage disequilibrium therewith is detected in a biological sample obtained from the subject. In one embodiment, the SNP at the TNFRSF1B gene locus comprises the risk allele, "C" at nucleobase 256 within SEQ ID NO. 1. A TNFRSF1B risk genotype may comprise a single copy of the risk allele, "C" at nucleobase 256 within rs5745994 (SEQ ID NO. 1). A TNFRSF1B risk genotype may comprise two copies of the of the risk allele, "C" at nucleobase 256 within rs5745994 (SEQ ID NO. 1). In one aspect, provided herein, detection of the SNP at the TNFRSF1B gene locus is used to predict and/or diagnose non-response to anti-TNF therapy in a subject. In one aspect, provided herein, detection of the SNP at the TNFRSF1B gene locus is used to treat the inflammatory disease or condition, or fibrostenotic and/or fibrotic disease, in a subject who is, or is predicted to be, non-responsive to anti-TNF therapy. TNFRSF1B is a gene that encodes tumor necrosis factor receptor 2 (TNFR2), which is a membrane-bound receptor of TNF-α and a critical signaling protein in the immune system. TNFR2, and nucleic acids encoding TNFR2, are characterized by NCBI Gene ID 7133.

In an aspect, provided herein, a SNP at the HLA-DRB6 gene locus comprising a risk allele, "C" at nucleobase 501 within rs11757159 (SEQ ID NO: 2), a portion of which sequence is shown in of Table 3, or any SNP in linkage disequilibrium therewith, is detected in a biological sample obtained from the subject. In some embodiments, the SNP at the HLA-DRB6 gene locus comprises the risk allele, "C" at nucleobase 501 within SEQ ID NO. 2. A HLA-DRB6 risk genotype may comprise a single copy of the risk allele, "C," at nucleobase 501 within rs11757159 (SEQ ID NO. 2). The HLA-DRB6 risk genotype may comprise two copies of the risk allele, "C," at nucleobase 501 within rs11757159 (SEQ ID NO. 2). In one aspect, provided herein, detection of the SNP at the HLA-DRB6 gene locus is used to predict and/or diagnose non-response to anti-TNF therapy. In one aspect, provided herein, detection of the SNP at the HLA-DRB6 gene locus is used to treat the inflammatory disease or condition, or fibrostenotic and/or fibrotic disease, in a subject who is, or is predicted to be, non-responsive to anti-TNF therapy. HLA-DRB6 is a gene that encodes a major histocompatibility complex, class II, DR beta 6 (HLA-DRB6). HLA-DRB6, and nucleic acids encoding HLA-DRB6, are characterized by NCBI Gene ID 3128.

TABLE 3

SNPS Associated with Non-Response to anti-TNF Therapy

| SEQ ID No. | SNP | Gene Locus | Risk Allele | Sequence |
|---|---|---|---|---|
| 1 | rs5745994 | INFRSF1B | C | TGCTCCCGGG GGTCCTGGGA AGGCACAATG GTGACAGTGC TGCAGCTCTG CACTCCTGGA GGGTCACTCA GAGAC [C/T] CGAGAGAGGAGGGCTCTGCG TCTGCTCCTC TGTCCAGGGC TGTAGCTTCT CTGGGTGCCT TTGCTTTTCT |
| 2 | rs11757159 | HLA-DRB6 | C | TGGTTTCTCA TCTCAATGTT TGACAAGTTT GTTTCAGTTG TTATAGTCTG TTCTCAGTTT TTATGCACTG CCTTTTTGAA [C/T] GTTAGGTTTA CTTTTTTAAT TGACAAGTAA AAATTGTATA GTATATTTAT GTTGTAGAGC ATGAAATTTT GATATATGCC |

In some embodiments, provided is a method of detecting a genotype or SNP comprising detecting the presence, absence, and/or quantity of a nucleic acid sequence, or portion thereof, selected from SEQ ID NOS: 1-2, or a combination thereof of Table 3. In some embodiments, provided is a method of detecting a genotype or SNP comprising detecting the presence, absence, and/or quantity of a nucleic acid sequence, or portion thereof, selected from the reverse complement of SEQ ID NOS: 1-2, or a combination thereof of Table 3. In some cases, a portion of a nucleic acid sequence provided herein comprises at least about 10, 15, 20, 25, 30, 35, 40, 45, or 50 contiguous nucleobases. In some cases, a portion of a nucleic acid sequence provided herein comprises between about 10 and about 50 contiguous nucleobases, between about 10 and about 40 contiguous nucleobases, between about 15 and about 50 contiguous nucleobases, between about 15 and about 40 contiguous nucleobases, between about 20 and about 50 contiguous nucleobases, and between about 20 and about 40 contiguous nucleobases. In some cases, a portion of a nucleic acid sequence provided herein comprises about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous nucleobases. In some cases, a portion of a nucleic acid sequence provided in Table 3 comprises a nucleobase within [brackets]. In some cases, the portion comprises a "C" at nucleobase 501 within SEQ ID NO: 1. In some cases, the portion comprises a "C" at nucleobase 501 within SEQ ID NO: 2. In some cases, e.g., when the reverse complement of SEQ ID NO: 1 is detected, the portion comprises a "T" in the position shown within brackets in Table 3. In some cases, e.g., when the reverse complement of SEQ ID NO: 2 is detected, the portion comprises a "T" in the position shown within brackets in Table 3.

In some embodiments, the method comprises determining the presence of the genotype or SNP in a sample obtained from a subject as determined by detecting the presence or absence of: a nucleic acid sequence at least or about 90% identical to SEQ ID NO: 1, a nucleic acid sequence at least or about 90% identical to SEQ ID NO: 2, a nucleic acid sequence at least or about 90% identical to a portion of SEQ ID NO: 1, a nucleic acid sequence at least or about 90% identical to a portion of SEQ ID NO: 2, or a combination thereof, in the genetic material. In some cases, if the subject comprises the genotype or SNP, the subject is administered a therapeutic agent, as disclosed herein.

In some embodiments, the method comprises determining the presence of the genotype or SNP in a sample obtained from a subject as determined by detecting the presence or absence of: a nucleic acid sequence at least or about 95% identical to SEQ ID NO: 1, a nucleic acid sequence at least or about 95% identical to SEQ ID NO: 2, a nucleic acid sequence at least or about 95% identical to a portion of SEQ ID NO: 1, a nucleic acid sequence at least or about 95% identical to a portion of SEQ ID NO: 2, or a combination thereof, in the genetic material. In some cases, if the subject comprises the genotype or SNP, the subject is administered a therapeutic agent, as disclosed herein.

In some embodiments, the method comprises determining the presence of the genotype or SNP in a sample obtained from a subject as determined by detecting the presence or absence of: the reverse complement of a nucleic acid sequence at least or about 90% identical to SEQ ID NO: 1, the reverse complement of a nucleic acid sequence at least or about 90% identical to SEQ ID NO: 2, the reverse complement of a nucleic acid sequence at least or about 90% identical to a portion of SEQ ID NO: 1, the reverse complement of a nucleic acid sequence at least or about 90% identical to a portion of SEQ ID NO: 2, or a combination thereof, in the genetic material. In some cases, if the subject comprises the genotype or SNP, the subject is administered a therapeutic agent, as disclosed herein.

In some embodiments, the method comprises determining the presence of the genotype or SNP in a sample obtained from a subject as determined by detecting the presence or absence of: the reverse complement of a nucleic acid sequence at least or about 95% identical to SEQ ID NO: 1, the reverse complement of a nucleic acid sequence at least or about 95% identical to SEQ ID NO: 2, the reverse complement of a nucleic acid sequence at least or about 95% identical to a portion of SEQ ID NO: 1, the reverse complement of a nucleic acid sequence at least or about 95% identical to a portion of SEQ ID NO: 2, or a combination thereof, in the genetic material. In some cases, if the subject comprises the genotype or SNP, the subject is administered a therapeutic agent, as disclosed herein.

Detecting TNFR2 Levels to Identify Non-Response to anti-TNF Therapy in a Subject In one aspect, provided herein, a level of TNFR1 or TNFR2, or a combination thereof, is detected in a biological sample obtained from a subject with an inflammatory disease or condition, or fibrostenotic and/or fibrotic disease, In some embodiments, the level of TNFR1 or TNFR2, or combination thereof is lower as compared to an individual who does not express the TNRSF1B risk genotype. In some embodiments, the level of TNFR1 or TNFR2, or combination thereof is higher as compared to an individual who does not express the TNRSF1B risk genotype. In some embodiments, the level of TNFR1 or TNFR2, or combination thereof is lower as compared to an individual who does not express the HLA-DRB6 risk genotype. In some embodiments, the level of TNFR1 or TNFR2, or combination thereof is higher as compared to an individual who does not express the HLA-DRB6 risk genotype. In one aspect, provided herein, detection of the level of TNFR1 or TNFR2 is used to predict and/or diagnose non-response to anti-TNF therapy in a subject. In one aspect, provided herein, detection of the level of TNFR1 or TNFR2 is used to treat the inflammatory disease or condition, or fibrostenotic and/or fibrotic disease, in a subject who is, or is predicted to be, non-responsive to anti-TNF therapy. In some embodiments, a method of detecting a level of TNFR1 and/or TNFR2 comprises performing an enzyme-linked immunosorbent assay (ELISA) or other means known in the art for the detection of proteins, such as those described elsewhere herein.

TNFRSF1B is a gene that encodes tumor necrosis factor receptor 2 (TNFR2), which is a membrane-bound receptor of TNF-α and a critical signaling protein in the immune system. TNFRSF1A is a gene that encodes tumor necrosis factor receptor 1 (TNFR1), which is a membrane bound, or soluble, receptor of TNFα, that also plays a role in the immune system. TNFR1 is expressed in almost all the cell types in human body, whereas TNFR2 is largely expressed in immune-related cells, such as lymphocytes (CD4 and CD8 cells), endothelia cells, and thymocytes. TNF-α binding to TNFR2 triggers the recruitment of the adapter proteins TNF receptor-associated factor 1 (TRAF1) and TNF receptor-associated factor 2 (TRAF2), precipitating activation of the downstream cascade of nuclear factor-kappa B (NFkB) and c-Jun N-terminal kinase (JNK). This cascade results in proliferation of multiple immune-related cells, including cytotoxic T cells, thymocytes, mononuclear cells as well as Treg cells, indicating the complex and crucial role of TNFR2 in human immune response. TNFR2 has also been reported to mediate slan dendritic cell (slanDC) enhancement of NK-cell function, promote suppressive activities of myeloid-derived suppressor cells, and play a crucial auxiliary role to TNFR1 in sensitizing macrophages for the activation of the p38 mitogen-activated protein kinases (MAPK) and NFkB proinflammatory signaling pathways.

Detecting ANCA Levels to Identify Non-Response to anti-TNF Therapy in a Subject

In one aspect, provided herein, a level of ANCA is detected in a biological sample obtained from a subject with an inflammatory disease or condition, or fibrostenotic and/or fibrotic disease. ANCA levels may comprise a threshold level that serves as an independent indicator of a subject being, or being susceptible to, non-response to anti-TNF therapy. In an embodiment provided herein, a first threshold ANCA level is at or above about 100 ELISA units (EU), which is an independent indicator of the subject being, or being susceptible to, non-response to anti-TNF therapy. ANCA levels may comprise a second level that is lower than about 100 EU and above about 50 EU, which serves as an indicator of a subject being, or being susceptible to, non-response to anti-TNF therapy if either (i) a decrease in circulating TNFR2 levels, or (ii) a presence of the SNP at the TNFRSF1B gene locus, or a combination thereof, is detected in the sample obtained from the subject. In another embodiment, the second threshold level of ANCA is at or above 50 EU. In some embodiments, the level of ANCA is between 50 and 60 EU. In some embodiments, the ANCA level is between 60 and 70 EU. In some embodiments, the ANCA level is between 70 and 80 EU. In some embodiments, the ANCA level is between 80 and 90 EU. In some embodiments, the ANCA level is above 90 EU and below 100 EU. In one aspect, provided herein, detection of ANCA levels, as disclosed herein, is used to predict and/or diagnose non-response to anti-TNF therapy in a subject. In one aspect, provided herein, detection of ANCA levels is used to treat the inflammatory disease or condition, or fibrostenotic and/or fibrotic disease, in a subject who is, or is predicted to be, non-responsive to anti-TNF therapy.

In some embodiments, the ANCA level is measured using immunohistochemistry. In some embodiments, the ANCA level is measured using an enzyme-linked immunosorbent assay (ELISA). The ELISA may be a fixed-ELISA. The fixed-ELISA may be fixed granulocytes as disclosed, for example, in Saxon et al., A distinct subset of antineutrophil cytoplasmic antibodies is associated with inflammatory bowel disease, J. Allergy Clin. Immuno. 86:2; 202-210 (August 1990).

Previous studies suggest that serum ANCA is a result of reactivity to local antigens. Previous studies have shown that the antigen for IBD-associated ANCA is nuclear and reactivity can be eliminated by pretreating neutrophils with DNase, which suggests that ANCA could be a marker for increased nuclear destruction within the mucosa involving release of nuclear antigens potentially related to ongoing apoptotic activity. Inhibition of mucosal inflammation by TNFα is driven by induction of T-cell apoptosis. Apoptosis is dependent on a balance of pro versus anti-apoptotic signal generating molecules that induce or protect against apoptosis. Membrane TNF, present on macrophages, preferentially binds to TNFR2 as opposed to TNFR1 on activated CD4 T cells. Downstream signaling of TNFR2 activates NFKB, which induces intracellular molecules and soluble cytokines that protect the cell from proapoptotic signals and raise the threshold for apoptosis in CD4 T cells. The result is increasing numbers of activated mucosal T cells in patients with IBD. Therapeutic antibodies to TNF bind transmembrane TNF, potentially preventing TNFR2 signaling that lowers the apoptotic threshold and makes these cells more susceptible to ongoing apoptosis, resulting in decreased numbers of mucosal effector T cells. Thus, without being bound to any particular theory, high ANCA levels and lower levels of TNFR2 (reflected by lower circulating TNFR2 levels) suggest ongoing mucosal apoptosis. Therefore, treating this population with anti-TNF will not further enhance apoptosis and a therapeutic that targets different mechanisms, such as a therapeutic targeting TL1A, would be indicated.

Detecting the TNRSF1B Risk Genotype, Decreased TNFR2, and ANCA Level to Identify Non-Response to Anti-TNF Therapy in Subjects with IBD In one aspect, provided herein, detection of a TNFRSF1B risk genotype, an increased level of ANCA, and decreased circulating TNFR2, in a biological sample obtained from a subject with an inflammatory disease or condition, or fibrostenotic and/or fibrotic disease, is used to identify or predict non-response to anti-TNF therapy in the subject. In one aspect, provided herein, detection of a TNFRSF1B risk genotype, an increased level of ANCA, and decreased circulating TNFR2, in a biological sample obtained from a subject with an inflammatory disease or condition, or fibrostenotic and/or fibrotic disease, is used to treat the inflammatory disease or condition, or fibrostenotic and/or fibrotic disease. In aspect, provided herein, a SNP at the TNFRSF1B gene locus comprising a risk allele, "C" at nucleobase 256 within rs5745994 (SEQ ID NO: 1), a portion of which sequence shown in of Table 3, or any polymorphism in linkage disequilibrium therewith is detected in a biological sample obtained from the subject. In one embodiment, the SNP at the TNFRSF1B gene locus comprises the risk allele, "C" at nucleobase 256 within SEQ ID NO. 1. A TNFRSF1B risk genotype may comprise a single copy of the risk allele, "C" at nucleobase 256 within rs5745994 (SEQ ID NO. 1). A TNFRSF1B risk genotype may comprise two copies of the of the risk allele, "C" at nucleobase 256 within rs5745994 (SEQ ID NO. 1). In some embodiments, the TNFRSF1B risk genotype may be detected by contacting the biological sample obtained from the subject with a nucleic acid sequence capable of hybridizing to 10 nucleobases of SEQ ID NO. 1 spanning nucleobase 256 under standard hybridization conditions. In some embodiments, the standard hybridization conditions comprise an annealing temperature between about 30° C. and about 65° C. In an embodiment provided herein, a first threshold ANCA level is at or above about 100 ELISA units (EU), which is an independent indicator that the subject is, or is susceptible to non-response to anti-TNF therapy. ANCA levels may comprise a level that is lower than about 100 EU and above about 50 EU, which serves as an indicator that the subject is, or is susceptible to, non-response to anti-TNF therapy if either (i) a decrease in circulating TNFR2 levels, or (ii) a presence of the SNP at the TNFRSF1B gene locus, or a combination thereof, is detected in the biological sample obtained from the subject. In another embodiment, a second threshold level of ANCA is at or above 50 EU. In some embodiments, the level of ANCA is between 50 and 60 EU. In some embodiments, the ANCA level is between 60 and 70 EU. In some embodiments, the ANCA level is between 70 and 80 EU. In some embodiments, the ANCA level is between 80 and 90 EU. In some embodiments, the ANCA level is above 90 EU and below 100 EU. In some embodiments, the ANCA level is measured using immunohistochemistry. In some embodiments, the ANCA level is measured using an enzyme-linked immunosorbent assay (ELISA). The ELISA may be a fixed-ELISA. The fixed-ELISA may be fixed with granulocytes as disclosed, for example, in Saxon et al., A distinct subset of antineutrophil cytoplasmic antibodies is associated with inflammatory bowel disease, *J. Allergy Clin. Immuno.* 86:2; 202-210 (August 1990). In some embodiments, the level of TNFR2 is lower as compared to an individual who does not express the TNRSF1B risk genotype. In some embodiments, the level of TNFR2 is measured using immunohistochemistry. In some embodiments, the level of TNFR2 is measured using an ELISA.

Methods of Selecting a Therapy

In an aspect, provided herein, are methods of selecting a therapy for a subject with inflammatory disease or condition, or fibrostenotic and/or fibrotic disease, comprising requesting the results of whether the subject is non-responsive to anti-TNF therapy, wherein the results are obtained by (i) obtaining a biological sample from the subject, (ii) assaying the sample to determine the presence of a TNFRSF1B SNP, (iii) assaying the sample for a serological factor comprising ANCA; determining the subject as non-responsive to anti-TNF therapy based on the presence of a TNFRSF1B SNP and an increase in the serological factor relative to a reference value obtained from an individual who does not express the TNFRSF1B SNP; and selecting a non-anti-TNF therapy for the subject. In some embodiments, the non-anti-TNF therapy comprises an anti-TL1A therapy. In some embodiments, the anti-TL1A therapy comprises an anti-TL1A antibody. In some embodiments, the anti-TL1A therapy comprises a blocking TL1A antibody. In some embodiments, inflammatory disease and/or condition comprises IBD. In some embodiments, the IBD comprises Crohn's disease or ulcerative colitis. In some embodiments, the method further comprises assaying for TNFR2 levels. In other embodiments, a decrease in TNFR2 levels as compared to an individual who does not express the TNFRSF1B SNP, is indicative of a subject non-responsive to anti-TNF therapy. In various embodiments, the method further comprises administering the non-anti-TNF therapy, which includes but is not limited to, those disclosed above. In other embodiments, the method further comprises assaying the biological sample for the presence of a HLA-DRB6 SNP. In various embodiments, the biological sample is assayed for the HLA-DRB6 SNP and a serological factor. In some embodiments, the HLA-DRB6 SNP variant is rs11757159 (SEQ ID NO: 2). In some embodiments, the serological factor is ANCA. In some embodiments, the presence of the HLA-DRB6 SNP is associated with a decrease in ANCA.

Compositions and Kits

In an aspect, disclosed herein, are kits to identify a subject with IBD, CD and/or UC that is non-responsive to anti-TNF therapy and/or selecting a therapy for a subject with IBD, CD and/or UC in need of treatment. The kit is useful for practicing the methods disclosed herein. The kit is an assemblage of materials or components, including at least one of the inventive compositions. Thus, in some embodiments the kit contains a composition including primers and probes for detecting the proteins and/or genes comprising TNFRSF1B, ANCA, TNFR2 and/or HLA-DRB6, as described above.

The exact nature of the components configured in the inventive kit depends on its intended purpose. For example, some embodiments are configured for the purpose of assessing risk variants, protein level, and/or gene expression levels. In some embodiments, the kit is configured to detect a presence, or gene expression levels, of TNFRSF1B in a sample. In yet other embodiments, the kit is configured to detect the presence, or gene expression levels, of gene expression products from the gene TNFRSF1B and/or HLA-DRB6 in a sample. Gene expression product from a gene may be RNA and/or protein expressed from the gene.

Other embodiments are configured for the purpose of assessing protein levels. In some embodiments, the kit is configured to detect the protein levels of TNFR1, TNFR2, and/or ANCA in a sample. In some other embodiments, the kit is configured to detect the protein levels of ANCA, TNFR2 and/or HLA-DRB6 in a sample. In one embodiment, the kit is configured to detect TNFRSF1B and/or HLA-DRB6 risk genotypes in a sample.

In one embodiment, the kit is configured particularly for the purpose of assessing mammalian subjects. In another embodiment, the kit is configured particularly for the purpose of assessing human subjects. In further embodiments, the kit is configured for veterinary applications, assessing subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to identify a subject with IBD, CD and/or UC that is non-responsive to anti-TNF therapy and/or select a therapy for, or treat using the therapy, a subject with IBD, CD and/or UC in need of treatment. In some embodiments, the therapy comprises an inhibitor of TL1A activity or expression. In some embodiments, the inhibitor of TL1A activity or expression comprises an anti-TL1A antibody. Optionally, the kit also contains other useful components, such as, primers, diluents, buffers, pipetting or measuring tools or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in gene and/or protein expression assays. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing primers and probes for detection of proteins and/or genes selected from TNFRSF1B, ANCA, TNFR2 and/or HLA-DRB6. The packaging material generally has an external label which indicates the contents and/or purpose of the kit and/or its components.

An aspect, provided herein, are compositions comprising at least 10 but less than 50 contiguous nucleobase residues of SEQ ID NOs. 1 or 2, wherein the contiguous nucleobase residues comprise the nucleobase at position 256 of SEQ ID No. 1, or position 501 at SEQ ID No. 2, and wherein the contiguous nucleobase residues are connected to a detectable molecule. The detectable molecule may be any molecule suitable for nucleic acid detection. In some embodiments, the detectable molecule is a fluorophore. In some embodiments the contiguous nucleobase residues are connected to a quencher. As a non-limiting example, the compositions are a probe useful for detection of the presence or absence of a SNP disclosed herein. An aspect, provided herein are kits comprising a probe described herein and a primer pair, each primer having a nucleic acid sequence hybridizable to 10 different contiguous nucleobases of SEQ ID NO: 1, wherein the primer pair is configured to amplify at least about 30 nucleobases of SEQ ID NO: 1 in a standard amplification assay (e.g., PCR), and wherein the at least 30 nucleobases comprise nucleobase 256 of SEQ ID NO. 1. In another aspect, provided herein are kits comprising a probe described herein and a primer pair, each primer having a nucleic acid sequence hybridizable to 10 different contiguous nucleobases of SEQ ID NO: 2, wherein the at least about 30 nucleobases comprise nucleobase 501 of SEQ ID NO. 2. In some embodiments, methods are provided for contacting DNA from a subject with the composition described herein, or using the kit described herein under conditions configured to hybridize the composition to the DNA if the DNA comprises a sequence complementary to the composition. In further embodiments, provided herein are methods of treating the subject with an inhibitor of TL1A activity or expression, provided that the DNA from the subject comprises the sequence complementary to the composition. In some embodiments, the kit disclosed herein comprises an ELISA. In some embodiments, the ELISA is a fixed-ELISA. In some embodiments, the fixed-ELISA comprises purified phosphopeptidomannan derived from yeast configured to detect a level of ANCA, as disclosed herein.

Biological Samples, Sample Preparation and Genotype Detection

In an aspect, provided herein, the steps involve obtaining a biological sample from a subject. The biological sample may be obtained either through surgical biopsy or surgical resection. Alternatively, a sample can be obtained through primary patient derived cell lines, or archived patient samples in the form of FFPE (Formalin fixed, paraffin embedded) samples, or fresh frozen samples. A sample may also comprise whole blood, peripheral blood, plasma, serum, saliva, cheek swab, or other bodily fluid or tissue. In various embodiments, the sample comprises tissue from the large and/or small intestine. In various other embodiments, the large intestine sample comprises the cecum, colon (the ascending colon, the transverse colon, the descending colon, and the sigmoid colon), rectum and/or the anal canal. In yet other embodiments, the small intestine sample comprises the duodenum, jejunum, and/or the ileum. In some embodiments, the sample is a blood sample. In yet other embodiments, the sample is serum. In yet other embodiments, two samples are collected. In some embodiments, the samples are tissue and blood.

Nucleic acid or protein samples derived from the biological sample (i.e., tissue and/or cells) of a subject that can be used in the methods disclosed herein can be prepared by means well known in the art. For example, surgical procedures or needle biopsy aspiration can be used to collect the biological samples from a subject. In some embodiments, it is important to enrich and/or purify the abnormal tissue and/or cell samples from the normal tissue and/or cell samples. In other embodiments, the abnormal tissue and/or cell samples can then be microdissected to reduce the amount of normal tissue contamination prior to extraction of genomic nucleic acid or pre-RNA for use in the methods disclosed herein. Such enrichment and/or purification can be accomplished according to methods well-known in the art, such as needle microdissection, laser microdissection, fluorescence activated cell sorting, and immunological cell sorting.

Analysis of the nucleic acid and/or protein from an individual may be performed using any of various techniques. In various embodiments, assaying gene expression products from the genes TNFRSF1B, TNFRSF1A, and/or HLA-DRB6 comprises northern blot, reverse transcription PCR, real-time PCR, serial analysis of gene expression (SAGE), DNA microarray, tiling array, RNA-Seq, or a combination thereof. In various other embodiments, the levels of gene expression products from the genes TNFRSF1B, TNFRSF1A, and/or HLA-DRB6 are assayed. In various other embodiments, the level of gene expression products from the gene TNFRSF1B are assayed. In various other embodiments, the levels of gene expression products from the gene HLA-DRB6 are assayed.

In various other embodiments, determining the protein expression level of ANCA, TNFR1 and/or TNFR2 can be accomplished by analyzing the proteins of a biological sample from the subject. In various embodiments, methods and systems to detect ANCA, TNFR1 and/or TNFR2, include but are not limited to enzyme-linked immunosorbent assay (ELISA), immunohistochemistry, western blot, flow cytometry, fluorescence in situ hybridization (FISH), radioimmuno assays, and affinity purification. In various embodiments, the assay is an ELISA, including but not limited to indirect ELISA, sandwich ELISA, competitive ELISA, multiple and portable ELISA, and fixed-ELISA. In various embodiments the ELISA is a fixed neutrophil ELISA. In some embodiments, the ELISA comprises fixed granulocytes, as disclosed, for example, in Saxon et al., A distinct subset of antineutrophil cytoplasmic antibodies is associated with inflammatory bowel disease, *J. Allergy Clin. Immuno.* 86:2; 202-210 (August 1990).

The analysis of gene expression levels may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

Methods of "quantitative" amplification may be used to detect the TNFRSF1 or HLA-DRB6 risk genotype. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods disclosed herein. In fluorogenic quantitative PCR, quantitation is based on amount of fluorescence signals, e.g., Taq-Man and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

A DNA sample suitable for hybridization can be obtained, e.g., by polymerase chain reaction (PCR) amplification of genomic DNA, fragments of genomic DNA, fragments of genomic DNA ligated to adaptor sequences or cloned sequences. Computer programs can be used in the design of primers with the desired specificity and optimal amplification properties, such as Oligo version 5.0 (National Biosciences). PCR methods are described, for example, in Innis et al., eds., 1990, PCR Protocols: A Guide to Methods And Applications, Academic Press Inc., San Diego, Calif. It will be apparent to one skilled in the art that controlled robotic systems are useful for isolating and amplifying nucleic acids and can be used.

A variety of methods can be used to determine the presence the TNFRSF1 or HLA-DRB6 risk genotype. As an example, enzymatic amplification of nucleic acid from an individual may be used to obtain nucleic acid for subsequent analysis, as discussed above. The presence or absence of a variant allele or haplotype may also be determined directly from the individual's nucleic acid without enzymatic amplification.

A TaqmanB allelic discrimination assay available from Applied Biosystems may be useful for detecting the TNFRSF1 or HLA-DRB6 risk genotype. In a TaqmanB allelic discrimination assay, a specific, fluorescent, dye-labeled probe for each allele is constructed. The probes contain different fluorescent reporter dyes such as FAM and VIC™ to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described, for example, in Kutyavin et al., "3'-minor groove binder-DNA probes increase sequence specificity at PCR extension temperature, "Nucleic Acids Research 28:655-661 (2000)). Minor grove binders include, but are not limited to, compounds such as dihydrocyclopyrroloindole tripeptide (DPI).

Sequence analysis also may also be useful for detecting the TNFRSF1 or HLA-DRB6 risk genotype. In some embodiments, DNA is fully or partially isolated and/or purified from other cellular material prior to or during DNA sequencing of the biological sample. In some instances, DNA is isolated and/or purified from other cellular materials by standard DNA purification techniques including, but not limited to, organic extraction (phenol, chloroform, and/or isoamyl alcohol), cesium chloride density gradients, anion-exchange methods, and selective adsorption to silica. Commercial kits available to at least partially isolate and/or purify DNA from cellular material include, but are not limited to, QIAamp (Qiagen), DNeasy (Qiagen), Quick-gDNA™ (Zymo Research), ZR-96 Quick-gDNA (Zymo Research), Xpedition™ (Zymo Research), DNAzol® (Life Technologies), ChargeSwitch® gDNA Mini Tissue Kit (Life Technologies), PureLink® (Life Technologies), GeneCatcher™ (Life Technologies), ChargeSwitch® Forensic DNA Purification Kit (Life Technologies), ReliaPrep™ (Promega), and Wizard® (Promega). In some instances, DNA is sequenced by traditional sequencing methods (see, A. M. Maxam and W. Gilbert, Proc. Natl. Acad. Sci. USA 74:560 (1977); Sanger et al., Proc. Natl. Acad. Sci. USA 74:5463 (1977)), next-generation sequencing methods (see, Mardis E R, Annu. Rev. Genomics Hum. Genet. USA 9:387 (2008)), or additional methods known to one of skill in the art.

Restriction fragment length polymorphism (RFLP) analysis may also be useful for detecting the TNFRSF1 or HLA-DRB6 risk genotype (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele specific oligonucleotide hybridization may also be used to detect a disease-predisposing allele. Allele-specific oligonucleotide hybridization is based on the use of a labeled oligonucleotide probe having a sequence perfectly complementary, for example, to the sequence encompassing a disease-predisposing allele. Under appropriate conditions, the allele-specific probe hybridizes to a nucleic acid containing the disease-predisposing allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a disease-predisposing allele by using an allele-specific oligonucleotide primer that is perfectly complementary to the nucleotide sequence of the disease-predisposing allele but which has one or more mismatches as compared to other alleles (Mullis et al., supra, (1994)). One skilled in the art understands that the one or more nucleotide mismatches that distinguish between the disease-predisposing allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer.

A heteroduplex mobility assay (HMA) is another assay that may be used to detect the TNFRSF1 or HLA-DRB6 risk genotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

The technique of single strand conformational, polymorphism (SSCP) also may be used to detect the presence of the TNFRSF1 or HLA-DRB6 risk genotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect the TNFRSF1 or HLA-DRB6 risk genotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence of the TNFRSF1 or HLA-DRB6 risk genotype. Other well-known approaches for determining the presence of the TNFRSF1 or HLA-DRB6 risk genotype include automated sequencing and RNAase mismatch techniques (Winter et al., Proc. Natl. Acad. Sci. 82:7575-7579 (1985)). Furthermore, one skilled in the art understands that, where the presence or absence of multiple alleles or haplotype(s) is to be determined, individual alleles can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods disclosed herein may be practiced using one or any combination of the assays described above or any another genetic assay.

Labeling

In some embodiments, the protein, polypeptide, nucleic acid, fragments thereof, or fragments thereof ligated to adaptor regions used in the aspects disclosed herein are detectably labeled. As a non-limiting example, a nucleic acid sequence hybridizable to a nucleic acid sequence comprising the SNP within rs5745994 is detectably labeled. As a non-limiting example, a nucleic acid sequence hybridizable to a nucleic acid sequence comprising the SNP within rs11757159 is detectably labeled. For example, the detectable label can be a fluorescent label, e.g., by incorporation of nucleotide analogues. Other labels suitable for use in aspects disclosed herein include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes.

Radioactive isotopes include that can be used in conjunction with the aspects disclosed herein, but are not limited to, $^{32}$P and $^{14}$C. Fluorescent molecules suitable for aspects disclosed herein include, but are not limited to, fluorescein and its derivatives, rhodamine and its derivatives, texas red, 5'carboxy-fluorescein ("FAM"), 2', 7'-dimethoxy-4', 5'-dichloro-6-carboxy-fluorescein ("JOE"), N, N, N', N'-tetramethyl-6-carboxy-rhodamine ("TAMRA"), 6-carboxy-X-rhodamine ("ROX"), HEX, TET, IRD40, and IRD41.

Fluorescent molecules which are suitable for use according to the aspects disclosed herein further include: cyamine dyes, including but not limited to Cy2, Cy3, Cy3.5, CY5, Cy5.5, Cy7 and FLUORX; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the aspects disclosed herein include, but are not limited to, ferritin, hemocyanin and colloidal gold.

Two-color fluorescence labeling and detection schemes may also be used (Shena et al., 1995, Science 270:467-470). Use of two or more labels can be useful in detecting variations due to minor differences in experimental conditions (e.g., hybridization conditions). In some embodiments, at least 5, 10, 20, or 100 dyes of different colors can be used for labeling. Such labeling would also permit analysis of multiple samples simultaneously which is encompassed by aspects disclosed herein.

The labeled nucleic acid samples, fragments thereof, or fragments thereof ligated to adaptor regions that can be used in the aspects disclosed herein are contacted to a plurality of oligonucleotide probes under conditions that allow sample nucleic acids having sequences complementary to the probes to hybridize thereto. Depending on the type of label used, the hybridization signals can be detected using methods well known to those of skill in the art including, but not limited to, X-Ray film, phosphor imager, or CCD camera. When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. (1996) *Genome Res.* 6, 639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al. (1996) *Genome Res.* 6, 639-645. Alternatively, a fiber-optic bundle can be used such as that described by Ferguson et al. (1996) *Nat. Biotech.* 14, 1681-1684. The resulting signals can then be analyzed to determine the expression of TNFRSF1B, ANCA, TNFR2 and/or HLA-DRB6 and housekeeping genes, using computer software.

In other embodiments, where genomic DNA of a subject is fragmented using restriction endonucleases and amplified prior to analysis, the amplification can comprise cloning regions of genomic DNA of the subject. In such methods, amplification of the DNA regions is achieved through the cloning process. For example, expression vectors can be engineered to express large quantities of particular fragments of genomic DNA of the subject (Sambrook and Russel, *Molecular Cloning: A Laboratory Manual* $4^{th}$ ed., Cold Spring Harbor Laboratory Press (Cold Spring Harbor, N.Y. 2012)).

In yet other embodiments, where the DNA of a subject is fragmented using restriction endonucleases and amplified prior to analysis, the amplification comprises expressing a nucleic acid encoding a gene, or a gene and flanking genomic regions of nucleic acids, from the subject. RNA (pre-messenger RNA) that comprises the entire transcript including introns is then isolated and used in the methods disclosed herein to analyze and provide a genetic signature of a cancer. In certain embodiments, no amplification is required. In such embodiments, the genomic DNA, or pre-RNA, of a subject may be fragmented using restriction endonucleases or other methods. The resulting fragments may be hybridized to SNP probes. Typically, greater quantities of DNA are needed to be isolated in comparison to the quantity of DNA or pre-mRNA needed where fragments are amplified. For example, where the nucleic acid of a subject is not amplified, a DNA sample of a subject for use in hybridization may be about 400 ng, 500 ng, 600 ng, 700 ng, 800 ng, 900 ng, or 1000 ng of DNA or greater. Alternatively, in other embodiments, methods are used that require very small amounts of nucleic acids for analysis, such as less than 400 ng, 300 ng, 200 ng, 100 ng, 90 ng, 85 ng, 80 ng, 75 ng, 70 ng, 65 ng, 60 ng, 55 ng, 50 ng, or less, such as is used for molecular inversion probe (MIP) assays. These techniques are particularly useful for analyzing clinical samples, such as paraffin embedded formalin-fixed material or small core needle biopsies, characterized as being readily available but generally having reduced DNA quality (e.g., small, fragmented DNA) and/or not providing large amounts of nucleic acids.

Once the expression levels have been determined, the resulting data can be analyzed using various algorithms, based on well-known methods used by those skilled in the art.

Systems

Disclosed herein, in some embodiments, is a system for detecting anti-TNF non-response in a subject, comprising analyzing genes or gene products expressed from TNFRSF1B, and/or HLA-DRB6, in a biological sample obtained from a subject. In some embodiments, the SNPs rs5745994 and rs11757159 of TNFRSF1B, and/or HLA-DRB6, respectively, are analyzed. The system is configured to implement the methods described in this disclosure, including, but not limited to, analyzing genes or gene expression products from the genes of a subject to determine whether the subject is, or is susceptible to being, non-responsive to anti-TNF therapy.

In some embodiments, disclosed herein is a system for detecting anti-TNF non-response in a subject, comprising: (a) a computer processing device, optionally connected to a computer network; and (b) a software module executed by the computer processing device to analyze a gene or gene expression product from one or more of the following TNFRSF1B, and/or HLA-DRB6, in a biological sample from a subject. In some instances, the system comprises a central processing unit (CPU), memory (e.g., random access memory, flash memory), electronic storage unit, computer program, communication interface to communicate with one or more other systems, and any combination thereof. In some instances, the system is coupled to a computer network, for example, the Internet, intranet, and/or extranet that is in communication with the Internet, a telecommunication, or data network. In some embodiments, the system comprises a storage unit to store data and information regarding any aspect of the methods described in this disclosure. Various aspects of the system are a product or article or manufacture.

One feature of a computer program includes a sequence of instructions, executable in the digital processing device's CPU, written to perform a specified task. In some embodiments, computer readable instructions are implemented as program modules, such as functions, features, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions are combined or distributed as desired in various environments. In some instances, a computer program comprises one sequence of instructions or a plurality of sequences of instructions. A computer program may be provided from one location. A computer program may be provided from a plurality of locations. In some embodiment, a computer program includes one or more software modules. In some embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application may utilize one or more software frameworks and one or more database systems. A web application, for example, is created upon a software framework such as Microsoft® .NET or Ruby on Rails (RoR). A web application, in some instances, utilizes one or more database systems including, by way of non-limiting examples, relational, non-relational, feature oriented, associative, and XML database systems. Suitable relational database systems include, by way of non-limiting examples, Microsoft® SQL Server, mySQL™, and Oracle®. Those of skill in the art will also recognize that a web application may be written in one or more versions of one or more languages. In some embodiments, a web application is written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). A web application may integrate enterprise server products such as IBM® Lotus Domino®. A web application may include a media player element. A media player element may utilize one or more of many suitable multimedia technologies including, by way of non-limiting examples, Adobe® Flash®, HTML 5, Apple® QuickTime®, Microsoft® Silverlight®, Java™, and Unity®.

Mobile Application

In some instances, a computer program includes a mobile application provided to a mobile digital processing device. The mobile application may be provided to a mobile digital processing device at the time it is manufactured. The mobile application may be provided to a mobile digital processing device via the computer network described herein.

A mobile application is created by techniques known to those of skill in the art using hardware, languages, and development environments known to the art. Those of skill in the art will recognize that mobile applications may be written in several languages. Suitable programming languages include, by way of non-limiting examples, C, C++, C #, Featureive-C, Java™, Javascript, Pascal, Feature Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments may be available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that may be run as an independent computer process, not an add-on to an existing process, e.g., not a plug-in. Those of skill in the art will recognize that standalone applications are sometimes compiled. In some instances, a compiler is a computer program(s) that transforms source code written in a programming language into binary feature code such as assembly language or machine code. Suitable compiled programming languages include, by way of non-limiting examples, C, C++, Featureive-C, COBOL, Delphi, Eiffel, Java™, Lisp, Python™, Visual Basic, and VB .NET, or combinations thereof. Compilation may be often performed, at least in part, to create an executable program. In some instances, a computer program includes one or more executable compiled applications.

Web Browser Plug-in

A computer program, in some aspects, includes a web browser plug-in. In computing, a plug-in, in some instances, is one or more software components that add specific functionality to a larger software application. Makers of software applications may support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. The toolbar may comprise one or more web browser extensions, add-ins, or add-ons. The toolbar may comprise one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

In some embodiments, Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. The web browser, in some instances, is a mobile web browser. Mobile web browsers (also called mircrobrowsers, mini-browsers, and wireless browsers) may be designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The medium, method, and system disclosed herein comprise one or more softwares, servers, and database modules, or use of the same. In view of the disclosure provided herein, software modules may be created by techniques known to those of skill in the art using machines, software, and languages known to the art. The software modules disclosed herein may be implemented in a multitude of ways. In some embodiments, a software module comprises a file, a section of code, a programming feature, a programming structure, or combinations thereof. A software module may comprise a plurality of files, a plurality of sections of code, a plurality of programming features, a plurality of programming structures, or combinations thereof. By way of non-limiting examples, the one or more software modules comprises a web application, a mobile application, and/or a standalone application. Software modules may be in one computer program or application. Software modules may be in more than one computer program or application. Software modules may be hosted on one machine. Software modules may be hosted on more than one machine. Software modules may be hosted on cloud computing platforms. Software modules may be hosted on one or more machines in one location. Software modules may be hosted on one or more machines in more than one location.

Databases

The medium, method, and system disclosed herein comprise one or more databases, or use of the same. In view of the disclosure provided herein, those of skill in the art will recognize that many databases are suitable for storage and retrieval of geologic profile, operator activities, division of interest, and/or contact information of royalty owners. Suitable databases include, by way of non-limiting examples, relational databases, non-relational databases, feature oriented databases, feature databases, entity-relationship model databases, associative databases, and XML databases. In some embodiments, a database is internet-based. In some embodiments, a database is web-based. In some embodiments, a database is cloud computing-based. A database may be based on one or more local computer storage devices.

Data Transmission

The subject matter described herein, including methods for obtaining and analyzing a molecular signature from a subject having a pigmented skin lesion, methods for obtaining a pigmented skin lesion, corresponding transmission of data, in certain aspects, are configured to be performed in one or more facilities at one or more locations. Facility locations are not limited by country and include any country or territory. In some instances, one or more steps for obtaining a molecular signature from a sample are performed in a different country than another step of the method. In some instances, one or more steps for obtaining a sample are performed in a different country than one or more steps for obtaining a molecular signature from a sample. In some embodiments, one or more method steps involving a computer system are performed in a different country than another step of the methods provided herein. In some embodiments, data processing and analyses are performed in a different country or location than one or more steps of the methods described herein. In some embodiments, one or more articles, products, or data are transferred from one or more of the facilities to one or more different facilities for analysis or further analysis. An article includes, but is not limited to, one or more components obtained from the tape stripping methods such as the adhesive tape, isolated cellular material obtained from an adhesive tape, processed cellular material, data, and any article or product disclosed herein as an article or product. Processed cellular material includes, but is not limited to, cDNA reverse transcribed from RNA, amplified RNA, amplified cDNA, sequenced DNA, isolated and/or purified RNA, isolated and/or purified DNA, and isolated and/or purified polypeptide. Data includes, but is not limited to, information regarding the gene expression profile of one or more target genes, information regarding a gene sequence profile signature, information regarding a protein sequence profile, information regarding the characteristic of a pigmented skin lesion (e.g., non-melanoma, melanoma in situ, invasive melanoma, stage 1 melanoma, stage 2 melanoma, stage 3 melanoma, stage 4 melanoma), and any data produced by the methods disclosed herein. In some embodiments of the methods and systems described herein, the analysis is performed and a subsequent data transmission step will convey or transmit the results of the analysis. Information regarding a pigmented skin lesion includes, but is not limited to, identification of melanoma, likelihood of treatment success for a subject having melanoma, identification of progression of a melanoma, identification of melanoma in situ, identification of invasive melanoma, and identification of a melanoma stage (e.g., 0, 1, 2, 3, 4).

In some embodiments, any step of any method described herein is performed by a software program or module on a computer. In additional or further embodiments, data from any step of any method described herein is transferred to and from facilities located within the same or different countries, including analysis performed in one facility in a particular location and the data shipped to another location or directly to an individual in the same or a different country. In additional or further embodiments, data from any step of any method described herein (including characterization of melanoma in situ and/or invasive melanoma, information regarding cellular material such as DNA, RNA, and protein as well as transformed data, e.g. a molecular signature, from cellular material) is transferred to and/or received from a facility located within the same or different countries, including analysis of a data input, such as cellular material, performed in one facility in a particular location and corresponding data transmitted to another location, or directly to an individual, such as data related to the diagnosis, prognosis, responsiveness to therapy, or the like, in the same or different location or country.

EXAMPLES

The following examples are not intended to limit the scope of the claims to the aspects disclosed herein, but are rather intended to be exemplary of certain embodiments. Any variations in the exemplified methods which occur to the skilled artisan are intended to fall within the scope of the aspects disclosed herein.

Example 1

Cedars-Sinai Cohort

Subjects were recruited in accordance with the recruitment carried out in Franke et al., Genome-wide meta-analysis increases to 71 the number of confirmed Crohn's disease susceptibility loci. Nat Genet. 2010; 42:1118-1125; McGovern et al., Fucosyltransferase 2 (FUT2) non-secretor status is associated with Crohn's disease. Hum Mol Genet. 2010; 19:3468-3476; Haritunians T et al., Genetic predictors of medically refractive ulcerative colitis, Inflamm Bow Dis. 2010; 16:1830-1840 and Anderson et al., Meta-analysis identifies 29 additional ulcerative colitis risk loci, increasing the number of confirmed associations to 47. Nat Genet. 2011; 43:246-252.

3110 patients with IBD were recruited at the Cedars-Sinai Inflammatory Bowel Disease Centers from 1985 to 2010. The diagnosis of each patient was based on standard endoscopic, histologic, and radiographic feature as previously described (Mow et al., Association of antibody responses to microbial antigens and complications of small bowel Crohn's disease. Gastroenterology. 2004; 126:414-424). Blood samples were collected at the time of enrollment. All study participants gave written informed content and the study protocol and data collection, as well as DNA preparation/genotyping and antibody measurement, was approved by the Cedars-Sinai Medical Center's Institutional Review Board.

Mount Sinai Hospital Cohort

A total of 1853 IBD cases were recruited and similarly characterized at Mount Sinai Hospital in Toronto, Canada. All subjects provided written consent after institutional review board's approval. The diagnosis of each patient was based on standard endoscopic, histologic, and radiographic feature.

ANCA Level Measurement

ANCA levels in serum from subjects from both centers were measured by enzyme-linked immunosorbent assay as previously described (Mow et al., Association of antibody responses to microbial antigens and complications of small bowel Crohn's disease. Gastroenterology. 2004; 126:414-424). All sera were analyzed in a blinded fashion at Cedars-Sinai Medical Center. Antibody levels were determined and results expressed as enzyme-linked immunosorbent assay units (EU/mL) as compared with a positive control (Mow et al., Association of antibody responses to microbial antigens and complications of small bowel Crohn's disease. Gastroenterology. 2004; 126:414-424). Qualitative positivity to ANCA was defined as being greater than cutoff values greater than 2 SDs above mean control titers.

Whole-Genome Genotyping:

Cedars-Sinai Cohort

Genotyping was performed at Cedars-Sinai Medical Center using Illumina whole-genome arrays per manufacturer's protocol (Illumina, San Diego, Calif.). The discovery cohort was genotyped on 3 platforms, including Illumina HumanCNV370-Quad (830 subjects), Human610-Quad (1037 subjects), and HumanOmniExpress (1243 subjects) arrays (total 3110 independent subjects). Average genotyping call rates for samples that passed quality control (QC) were 99.86% (HumanCNV370-Quad), 99.83% (Human610-Quad), and 99.85% (HumanOmniExpress). One to two percent of samples were genotyped in replicate and yielded average 99.99% concordance for genotypes called. Optimal allele-calling was verified by manual review of top associated single-nucleotide polymorphisms (SNPs).

A stringent QC procedure was applied to the GWAS data. Of the 3110 subjects genotyped, 10 were removed because of high missing rate (>2%), 27 were removed because of cryptic relatedness (Pi_Hat>0.05), 3 were removed because sample either withdrew from the study or was later reclassified as non-IBD, leaving 3070 individuals for further analysis. Seventy-six individuals identified as nonwhites by principal component analysis were also removed. A total of 2959 of the 2994 genotyped subjects had ANCA status and were thereby included in the analyses.

Mount Sinai Hospital Cohort

A total of 1853 patients with IBD from the Mount Sinai Hospital Cohort in Toronto were genotyped on Illumina HumanOmniExpress array. Average genotyping call rates for samples that passed QC were 99.88%. Thirty-two samples genotyped in replicate and yielded average 99.99% concordance for genotypes called. After similar QC procedures as the discovery cohort, 1834 subjects remain in the cleaned data set, of which 419 had ANCA status available measured in the same laboratory as the discovery cohort. The 419 individuals with consistent ANCA measurements were included in this study as replication cohort.

Imputation

To consolidate data from different genotyping platforms, imputation was performed using a hidden Markov model-based algorithm available in the IMPUTE224 software package with Phase 2 HapMap genotypes as the Ref. 25. In the imputed data set, only imputed SNPs with minor allele frequency (MAF)>0.01 and quality score >0.80 in all 3 Illumina platforms were retained, leaving approximately 2.01M SNPs for analyses.

Validation of Top-Hit SNP rs5745994

The most significant novel association observed in the genome-wide association analysis was with an imputed SNP (rs5745994). To validate the imputation, this SNP was included as custom content on the Illumina HumanExome+ array. BeadChip and genotyped as part of a larger project at Cedars-Sinai Medical Center following manufacturer's protocol (Illumina, San Diego, Calif.). Genotype clusters for rs5745994 were visualized to ensure accurate allele-calling. The average genotyping rate of samples in the project that passed genotyping QC was 99.98%. Two hundred seventy-three samples performed in replicate as controls yielded 99.9963% concordance for genotypes called.

Measure of TNFR1 and TNFR2 Levels

TNFR1 and TNFR2 concentrations were assessed in serum by commercially available enzyme-linked immunosorbent assay kits according to the manufacturer specified protocol (Biosource Invitrogen, KAC1761, KAC1771). The assay laboratory at Cedars-Sinai was blinded to subject status. Concentrations are reported in nanogram per milliliter.

Statistical Analysis

ANCA level in IBD cases is not normally distributed and the traditional method for analyzing skewed data, the nonparametric Mann-Whitney U test, is known to have lower efficiency and cannot incorporate covariates in analyses. Therefore, linear regression was used with the nontransformed ANCA level as outcome and for top SNPs, a permutation test was used to retain the type I error rate. The top 3 principal components and genotyping platform (in the discovery cohort) were included in the analysis as covariates to control for potential confounding. SNPTEST 2.2027 and R3.0228 were used in the statistical analysis. Similarly, permutation test was also performed in the analysis comparing circulating levels of TNFR1 and TNFR2 in carriers and non-carriers of the TNFRSF1B SNP.

Demographic Characteristics

Table 4 shows the demographic characteristics of the 2959 individuals included in the final analyses of the discovery cohort of 1653 (55.86%) CD, 1193 (40.31%) UC, and 113 (3.82%) IBD-unclassified. The average age of disease onset was 25.65±14.56 years old and 1513 (51.13%) are men. Median ANCA levels were 13.21 in CD, 36.00 in UC, and 18.93 in all IBD. A total of 433 CD (26.19%), 788 UC (66.05%), and 1278 all IBD (43.19%) were ANCA positive.

TABLE 4

Demographic Characters of the Discovery Cohort

| | CD | UC | All IBD |
|---|---|---|---|
| N | 1653 | 1193 | 2959[a] |
| Sex (M/F) | 842/811 | 608/585 | 1513/1446 |
| Age of diagnosis | 23.64 ± 13.73 | 28.19 ± 15.05 | 25.65 ± 14.56 |

TABLE 4-continued

Demographic Characters of the Discovery Cohort

|  | CD | UC | All IBD |
|---|---|---|---|
| ANCA level (median) | 13.21 | 36.00 | 18.93 |
| ANCA +/− | 433/1220 | 788/405 | 1278/1681 |

[a] One hundred thirteen IBD undetermined patients were also included.

SNP Associations with ANCA Level

Figure 2:
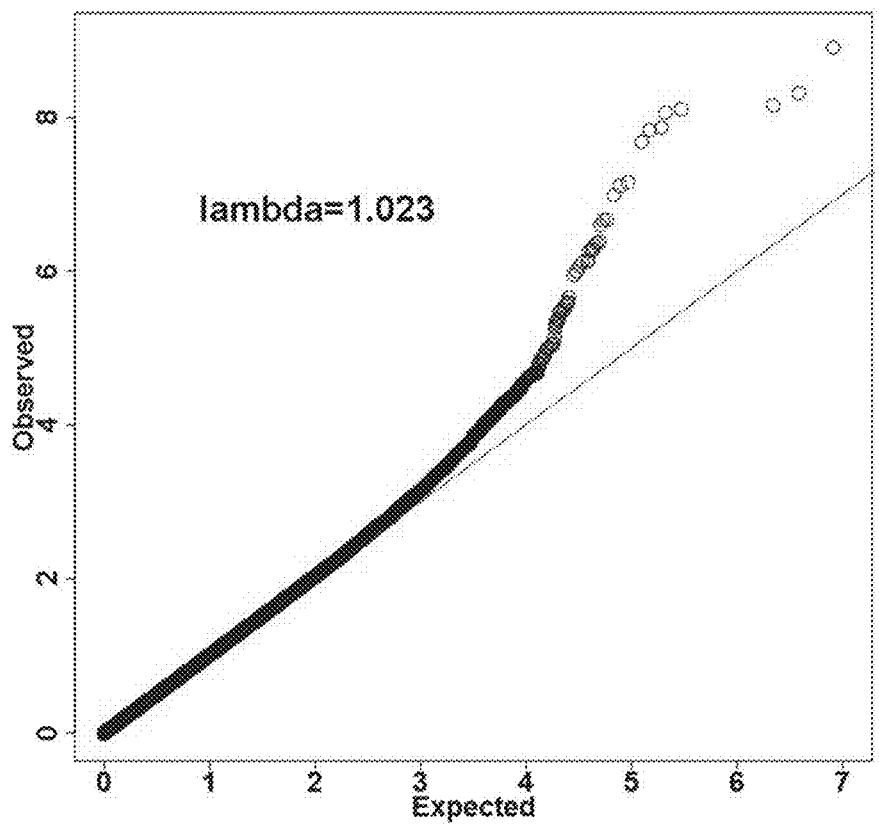
FIG. 2 depicts in accordance with various embodiments of an aspect provided herein, the genomic inflation factor for the genome-wide association in the discovery cohort.

Overall genomic inflation factor for the genome-wide association in the discovery cohort was 1.023 (see FIG. 1 and FIG. 2). FIG. 1 shows the Manhattan plot for association with ANCA level in the GWAS. Before performing permutation testing, 2 signals were observed that reached standard and stringent criteria for genome-wide significance threshold of $5.0 \times 10^{-8}$. The most significant SNP (rs11757159, MAF=0.326) is located in HLA-DRB6, with the minor allele C (frequency 0.33) associated with lower ANCA level (beta=−7.09, 95% CI, −9.27 to −4.91), with a permutation test P value of $2.55 \times 10^{-10}$. The second signal achieving genome-wide significance was located on 1p36.22 (rs5745994, MAF=0.028) which is located in the intron of TNFRSF1B. Individuals carrying the minor allele (C allele) have higher ANCA level (beta=18.12, 95% CI, 11.82-24.22), with a P-value of $1.89 \times 10^{-8}$ after permutation testing (Table 5). Additional haplotype-based analyses and conditional analyses for this region suggest that there is only 1 signal at this locus, tagged by rs5745994 (data not shown).

(Table 2). The original observation of an association between the C allele of rs5745994 and ANCA level, with similar effect magnitude (beta=16.91, 95% CI, 6.13-27.69, $P=2.38 \times 10^{-3}$), was confirmed. With a Q-value of 0.036, a fixed-effect meta-analysis for the association of rs5745994 in both cohorts was performed and observed a stronger association signal (beta=17.81, 95% CI, 12.36-23.25, $P=8.97 \times 10^{10}$). The HLA signal observed in the discovery cohort failed to replicate (beta=−2.30, P=0.262).

Association of the TNFRSF1B SNP with TNFR2 Level

Figure 3A:
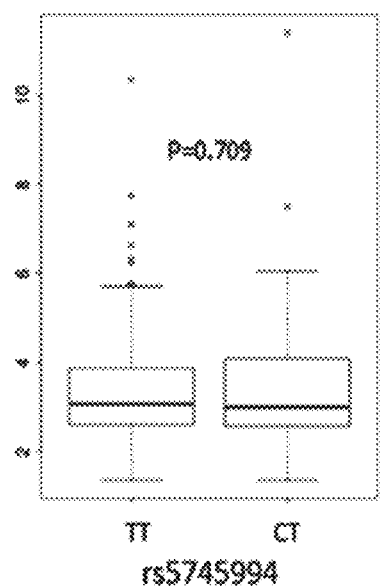
FIGS. 3A and 3B depict in accordance with various embodiments of an aspect provided herein, the association of rs5745994 with serum TNFR1 and TNFR2 levels.
Figure 3B:
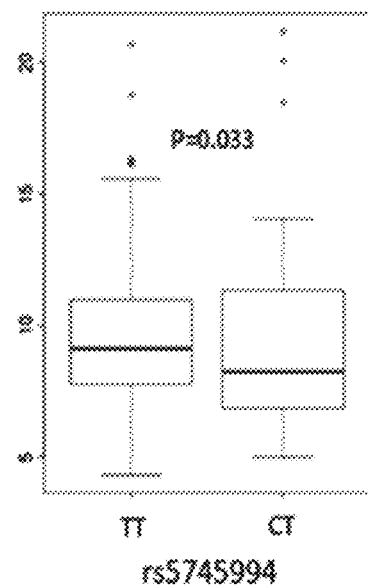

Next, the association between TNFRSF1B (rs5745994) and serum TNFR1 (as control) and TNFR2 levels was tested, in a subset of 239 patients with IBD, of which 58 carried the C allele of rs5745994 with the remainder being homozygous for the T allele. FIG. 3 shows the association of rs5745994 with TNFR1 and TNFR2. TNFRSF1B was not associated with TNFR1 (median 2.99 EU/mL in C allele carriers compared with 3.06 EU/mL in noncarriers, P=0.71). In contrast, the median TNFR2 was 8.23 EU/mL in carriers and 9.12 EU/mL in noncarriers (P=0.033), indicating lower serum TNFR2 level in carriers of the C allele.

Example 2

Detecting Anti-TNF-Alpha Non-Response as Determined by ANCA Level

Subjects are selected based on a diagnosis of IBD. The diagnosis of each patient is based on standard endoscopic, histologic, and radiographic feature as previously described

TABLE 5

Top SNPs in GWAS Analysis

| | | | | | | | | Discovery Cohort (N = 2959) | | | Replication Cohort (N = 419) | | | Meta-Analysis | |
|---|---|---|---|---|---|---|---|---|---|---|---|---|---|---|---|
| SEQ. | SNP | CHR | Position | Gene | A1 | A2 | MAF | Beta (95% CI) | $P^a$ | MAF | Beta (95% CI) | $P^a$ | Beta (95% CI) | $P^a$ |
| 1 | rs11757159 | 6 | 32.628250 | HLA-DRB6 | T | C | 0.326 | −7.09 (−9.27 to −4.91) | $2.55 \times 10^{-10}$ | 0.294 | −2.30 (−6.28 to 1.69) | 0.262 | −5.99 (−7.91 to −4.07) | $3.25 \times 10^{-8}$ |
| 2 | rs5745994 | 1 | 12.169715 | TNFR SF1B | T | C | 0.028 | 18.12 (11.86 to 24.38) | $1.89 \times 10^{-8}$ | 0.031 | 16.91 (6.13 to 27.69) | $2.38 \times 10^{-3}$ | 17.81 (12.36 to 23.25) | $8.97 \times 10^{-10}$ |

[a] P values after permutation test.
CHR, chromosome; MAF, minor allele frequency.

TNFSF1B SNP rs5745994 Associated with IBD

The association of the novel signal in TNFRSF1B was further examined separately in CD and UC. The signal is observed in both CD and UC, with a stronger effect observed in UC (CD: beta=11.14, 95% CI, 4.67-17.62, $P=1.24 \times 10^3$; UC: beta=23.83, 95% CI, 12.88-34.78, $P=8.42 \times 10^{-5}$).

Validation of the TNFRSF1B SNP in ExomeChip

As the TNFRSF1B SNP (rs5745994) was an imputed SNP, the imputation, by incorporating this SNP as a SNP in the customized content in our ExomeChip genotyping efforts were validated. Concordance rate between imputed and genotyped data for 2841 individuals with both GWAS and ExomeChip data was 99.64%. As expected, association analysis using only genotyped SNPs yielded similar results (beta=16.78, 95% CI, 10.16-23.40, $P=7.15 \times 10^{-7}$).

Replication of the Top Signals

Using an additional cohort of 419 patients with IBD from Mount Sinai Hospital in Toronto in which ANCA levels were analyzed at Cedars-Sinai, the association of the TNFRSF1B with ANCA levels were further examined (Mow et al., Association of antibody responses to microbial antigens and complications of small bowel Crohn's disease. Gastroenterology. 2004; 126:414-424). Blood samples are collected. Blood sera or plasma are isolated from blood samples.

Fixed-granulocyte ELISA assay: ANCA levels in blood sera or plasma are measured using a high-binding polystyrene microtiter plates coated with a monolayer of granulocytes by the addition of 0.1 ml of Hanks' balanced bufferedsale solution containing 500,000 granulocytes. After the cells settle and spread for 30 minutes at 23° C., the plates are centrifuged at 1000 rpm (300 g) for 5 minutes, the supernatant is aspirated from the wells, and the plates are air-dried for 2 hours. Methanol (100%) is then added for 10 minutes and discarded. The plates are air-dried and then stored at −20° C. For use, the plates are brought to room temperature and blocked for nonspecific binding by addition of 150 microliters of 1% BSA and 1% PBS for 1 hour. The blocking material is discarded, and then 100 microliters of solution of test serum diluted in 1% BSA/PBS is added and incubated for 1 hour in a humidified box. After four washes with PBS and Tween, 100 microliter per well of a 1:1500 dilution of alkaline phosphatase-coupled goat antibuman gamma-chain specific antibody (Tago, Inc., Burlingame, Calif.) in 1% BSA/PBS is added per well for 1 hour. This antibody is discarded, and the wells are washed three times with PBS/Tween and four times with Tris/NaCl (0.05 mol/L of Tris base in 0.9 N NaCl, pH 7.5). Substrate solution (disodium P-nitrophenol phosphate, 1.5 mg/ml and 100 p.1 per well) is added, and color development is allowed to proceed until absorbance at 405 nm in the positive control wells was 0.8. Levels are determined relative to a standard comprising of pooled sera obtained from well-characterized pANCA ulcerative colitis patients. Results are expressed as ELISA units, which reflect a percentage of the standard. Sera with circulating antineutrophil cytoplasmic IgG antibody exceeding the about 100 EU are termed ANCA+. Optionally, the subject is treated with a non-anti-TNF therapeutic agent provided herein. In some embodiments, the therapeutic agent comprises an anti-TL1A antibody.

Indirect immunofluorescence assay: Neutrophils separated by dextran sedimentation are re-suspended in PBS, and 100,000 cells are prepared on slides by cytocentrifugation (Cytospin, Shandon Southern Products, Cheshire, U.K.). The slides are fixed in 100% methanol at 4° C. for 10 minutes, air-dried, and stored at −20° C. The sera are tested at a dilution of 1:20, and staining with fluoroscein-labeled F(ab')$_2$ gamma-chain-specific antibody is performed as described. Slides were examined by fluorescence microscopy (40×Epifluor lens, Carl Zeiss, Inc., Thornwood, N.Y.).

Example 3

Detecting Anti-TNF-Alpha Non-Response as Determined by Presence of TNFRSF1B SNP

Subjects are selected based on a diagnosis of IBD. The diagnosis of each patient is based on standard endoscopic, histologic, and radiographic feature as previously described (Mow et al., Association of antibody responses to microbial antigens and complications of small bowel Crohn's disease. Gastroenterology. 2004; 126:414-424). Blood samples are collected.

The presence of the TNFRSF1B SNP rs5745994 is detected using quantitative nucleic acid amplification (qPCR) protocols, such as Innis, et al. (1990) PCR Protocols, *A Guide to Methods and Applications*, Academic Press, Inc. N.Y.). The measurement of DNA copy number at microsatellite loci using qPCR analysis is performed as described in Ginzonger, et al. (2000) *Cancer Research* 60:5405-5409. The probe sequence used is sufficiently complimentary to the oligonucleotide sequence of the TNFRSF1B SNP rs5745994 to allow detection of the gene comprising the risk allele, "C," at position 256 within rs5745994. The probe sequence is conjugated to a reporter dye, such as TaqMan or SYBR green, and a quencher, such that hybridization of the dye-conjugated probe sequence to the TNFRSF1B SNP rs5745994 is visualized.

Example 4

Detecting Anti-TNF-Alpha Non-Response as Determined by TNFR2 Level

Subjects are selected based on a diagnosis of IBD. The diagnosis of each patient is based on standard endoscopic, histologic, and radiographic feature as previously described (Mow et al., Association of antibody responses to microbial antigens and complications of small bowel Crohn's disease. Gastroenterology. 2004; 126:414-424). Blood samples are collected. Blood sera or plasma are isolated from the blood samples.

TNFR2 level is assessed in serum or plasma by commercially available enzyme-linked immunosorbent assay kits according to the manufacturer specified protocol (Biosource Invitrogen, KAC1761, KAC1771). Concentrations are reported in nanogram per milliliter.

Example 5

Detecting Anti-TNF-Alpha Non-Response as Determined by Presence of TNFRSF1B SNP and ANCA Level Subjects are selected based on a diagnosis of IBD. The diagnosis of each patient is based on standard endoscopic, histologic, and radiographic feature as previously described (Mow et al., Association of antibody responses to microbial antigens and complications of small bowel Crohn's disease. Gastroenterology. 2004; 126:414-424). Blood samples are collected. Blood sera or plasma are isolated from the blood samples.

The presence of the TNFRSF1B SNP rs5745994 is detected using quantitative nucleic acid amplification (qPCR) protocols, such as Innis, et al. (1990) PCR Protocols, A Guide to *Methods and Applications*, Academic Press, Inc. N.Y.). The measurement of DNA copy number at microsatellite loci using qPCR analysis is performed as described in Ginzonger, et al. (2000) *Cancer Research* 60:5405-5409. The probe sequence used is sufficiently complimentary to the oligonucleotide sequence of the TNFRSF1B SNP rs5745994 to allow detection of the gene comprising the risk allele, "C," at position 256 within rs5745994. The probe sequence is conjugated to a reporter dye, such as TaqMan or SYBR green, and a quencher, such that hybridization of the dye-conjugated probe sequence to the TNFRSF1B SNP rs5745994 is visualized.

Fixed-granulocyte ELSA assay: ANCA levels in blood sera or plasma are measured using a high-binding polystyrene microtiter plates coated with a monolayer of granulocyres by the addition of 0.1 ml of Hanks' balanced bufferedsale solution containing 500,000 granulocytes. After the cells settle and spread for 30 minutes at 23° C., the plates are centrifuged at 1000 rpm (300 g) for 5 minutes, the supernatant is aspirated from the wells, and the plates are air-dried for 2 hours. Methanol (100%) is then added for 10 minutes and discarded. The plates are air-dried and then stored at −20° C. For use, the plates are brought to room temperature and blocked for nonspecific binding by addition of 150 microliters of 1% BSA and 1% PBS for 1 hour. The blocking material is discarded, and then 100 microliters of solution of test serum diluted in 1% BSA/PBS is added and incubated for 1 hour in a humidified box. After four washes with PBS and Tween, 100 microliter per well of a 1:1500 dilution of alkaline phosphatase-coupled goat antibuman gamma-chain specific antibody (Tago, Inc., Burlingame, Calif.) in 1% BSA/PBS is added per well for 1 hour. This antibody is discarded, and the wells are washed three times with PBS/Tween and four times with Tris/NaCl (0.05 mol/L of Tris base in 0.9 N NaCl, pH 7.5). Substrate solution (disodium P-nitrophenol phosphate, 1.5 mg/ml and 100 p.1 per well) is added, and color development is allowed to proceed until absorbance at 405 nm in the positive control wells was 0.8. Levels are determined relative to a standard comprising of pooled sera obtained from well-characterized pANCA ulcerative colitis patients. Results are expressed as ELISA units, which reflect a percentage of the standard. Sera with circulating antineutrophil cytoplasmic IgG antibody that is at, or above about 50 EU are termed ANCA+. Optionally, the subject is treated with a non-anti-TNF therapeutic agent provided herein. In some embodiments, the therapeutic agent comprises an anti-TL1A antibody.

Indirect immunofluorescence assay: Neutrophils separated by dextran sedimentation are re-suspended in PBS, and 100,000 cells are prepared on slides by cytocentrifugation (Cytospin, Shandon Southern Products, Cheshire, U.K.). The slides are fixed in 100% methanol at 4° C. for 10 minutes, air-dried, and stored at −20° C. The sera are tested at a dilution of 1:20, and staining with fluoroscein-labeled F(ab')$_2$ gamma-chain-specific antibody is performed as described. Slides were examined by fluorescence microscopy (40×Epifluor lens, Carl Zeiss, Inc., Thornwood, N.Y.).

Example 6

Detecting Anti-TNF-Alpha Non-Response as Determined by Presence of TNFRSF1B SNP and TNFR2 Level Subjects are selected based on a diagnosis of IBD. The diagnosis of each patient is based on standard endoscopic, histologic, and radiographic feature as previously described (Mow et al., Association of antibody responses to microbial antigens and complications of small bowel Crohn's disease. Gastroenterology. 2004; 126:414-424). Blood samples are collected. Blood sera or plasma are isolated from the blood samples.

The presence of the TNFRSF1B SNP rs5745994 is detected using quantitative nucleic acid amplification (qPCR) protocols, such as Innis, et al. (1990) PCR Protocols, *A Guide to Methods and Applications*, Academic Press, Inc. N.Y.). The measurement of DNA copy number at microsatellite loci using qPCR analysis is performed as described in Ginzonger, et al. (2000) *Cancer Research* 60:5405-5409. The probe sequence used is sufficiently complimentary to the oligonucleotide sequence of the TNFRSF1B SNP rs5745994 to allow detection of the gene comprising the risk allele, "C," at position 256 within rs5745994. The probe sequence is conjugated to a reporter dye, such as TaqMan or SYBR green, and a quencher, such that hybridization of the dye-conjugated probe sequence to the TNFRSF1B SNP rs5745994 is visualized.

TNFR2 level is assessed in serum or plasma by commercially available enzyme-linked immunosorbent assay kits according to the manufacturer specified protocol (Biosource Invitrogen, KAC1761, KAC1771). Concentrations are reported in nanogram per milliliter.

Example 7

Detecting Anti-TNF-Alpha Non-Response as Determined by TNFR2 Level and ANCA Level Subjects are selected based on a diagnosis of IBD. The diagnosis of each patient is based on standard endoscopic, histologic, and radiographic feature as previously described (Mow et al., Association of antibody responses to microbial antigens and complications of small bowel Crohn's disease. Gastroenterology. 2004; 126:414-424). Blood samples are collected. Blood sera or plasma are isolated from the blood samples.

TNFR2 level is assessed in serum or plasma by commercially available enzyme-linked immunosorbent assay kits according to the manufacturer specified protocol (Biosource Invitrogen, KAC1761, KAC1771). Concentrations are reported in nanogram per milliliter.

Fixed-granulocyte ELISA assay: ANCA levels in blood sera or plasma are measured using a high-binding polystyrene microtiter plates coated with a monolayer of granulocyres by the addition of 0.1 ml of Hanks' balanced bufferedsale solution containing 500,000 granulocytes. After the cells settle and spread for 30 minutes at 23° C., the plates are centrifuged at 1000 rpm (300 g) for 5 minutes, the supernatant is aspirated from the wells, and the plates are air-dried for 2 hours. Methanol (100%) is then added for 10 minutes and discarded. The plates are air-dried and then stored at −20° C. For use, the plates are brought to room temperature and blocked for nonspecific binding by addition of 150 microliters of 1% BSA and 1% PBS for 1 hour. The blocking material is discarded, and then 100 microliters of solution of test serum diluted in 1% BSA/PBS is added and incubated for 1 hour in a humidified box. After four washes with PBS and Tween, 100 microliter per well of a 1:1500 dilution of alkaline phosphatase-coupled goat antihuman gamma-chain specific antibody (Tago, Inc., Burlingame, Calif.) in 1% BSA/PBS is added per well for 1 hour. This antibody is discarded, and the wells are washed three times with PBS/Tween and four times with Tris/NaCl (0.05 mol/L of Tris base in 0.9 N NaCl, pH 7.5). Substrate solution (disodium P-nitrophenol phosphate, 1.5 mg/ml and 100 p.1 per well) is added, and color development is allowed to proceed until absorbance at 405 nm in the positive control wells was 0.8. Levels are determined relative to a standard comprising of pooled sera obtained from well-characterized pANCA ulcerative colitis patients. Results are expressed as ELISA units, which reflect a percentage of the standard. Sera with circulating antineutrophil cytoplasmic IgG antibody that are at, or above, about 50 EU are termed ANCA+. Optionally, the subject is treated with a non-anti-TNF therapeutic agent provided herein. In some embodiments, the therapeutic agent comprises an anti-TL1A antibody.

Indirect immunofluorescence assay: Neutrophils separated by dextran sedimentation are re-suspended in PBS, and 100,000 cells are prepared on slides by cytocentrifugation (Cytospin, Shandon Southern Products, Cheshire, U.K.). The slides are fixed in 100% methanol at 4° C. for 10 minutes, air-dried, and stored at −20° C. The sera are tested at a dilution of 1:20, and staining with fluoroscein-labeled F(ab')$_2$ gamma-chain-specific antibody is performed as described. Slides were examined by fluorescence microscopy (40×Epifluor lens, Carl Zeiss, Inc., Thornwood, N.Y.).

Example 8

Detecting Anti-TNF-Alpha Non-Response as Determined by Presence of TNFRSF1B SNP, ANCA Level, and TNFR2 Level Subjects are selected based on a diagnosis of IBD. The diagnosis of each patient is based on standard endoscopic, histologic, and radiographic feature as previously described (Mow et al., Association of antibody responses to microbial antigens and complications of small bowel Crohn's disease. Gastroenterology. 2004; 126:414-424). Blood samples are collected. Blood sera or plasma are isolated from the blood samples.

The presence of the TNFRSF1B SNP rs5745994 is detected using quantitative nucleic acid amplification (qPCR) protocols, such as Innis, et al. (1990) PCR Protocols, A Guide to *Methods and Applications*, Academic Press, Inc. N.Y.). The measurement of DNA copy number at microsatellite loci using qPCR analysis is performed as described in Ginzonger, et al. (2000) *Cancer Research* 60:5405-5409. The probe sequence used is sufficiently complimentary to the oligonucleotide sequence of the TNFRSF1B SNP rs5745994 to allow detection of the gene comprising the risk allele, "C," at position 256 within rs5745994. The probe sequence is conjugated to a reporter dye, such as TaqMan or SYBR green, and a quencher, such that hybridization of the dye-conjugated probe sequence to the TNFRSF1B SNP rs5745994 is visualized.

TNFR2 level is assessed in serum or plasma by commercially available enzyme-linked immunosorbent assay kits according to the manufacturer specified protocol (Biosource Invitrogen, KAC1761, KAC1771). Concentrations are reported in nanogram per milliliter.

Fixed-granulocyte ELISA assay: ANCA levels in blood sera or plasma are measured using a high-binding polystyrene microtiter plates coated with a monolayer of granulocyres by the addition of 0.1 ml of Hanks' balanced bufferedsale solution containing 500,000 granulocytes. After the cells settle and spread for 30 minutes at 23° C., the plates are centrifuged at 1000 rpm (300 g) for 5 minutes, the supernatant is aspirated from the wells, and the plates are air-dried for 2 hours. Methanol (100%) is then added for 10 minutes and discarded. The plates are air-dried and then stored at −20° C. For use, the plates are brought to room temperature and blocked for nonspecific binding by addition of 150 microliters of 1% BSA and 1% PBS for 1 hour. The blocking material is discarded, and then 100 microliters of solution of test serum diluted in 1% BSA/PBS is added and incubated for 1 hour in a humidified box. After four washes with PBS and Tween, 100 microliter per well of a 1:1500 dilution of alkaline phosphatase-coupled goat antibuman gamma-chain specific antibody (Tago, Inc., Burlingame, Calif.) in 1% BSA/PBS is added per well for 1 hour. This antibody is discarded, and the wells are washed three times with PBS/Tween and four times with Tris/NaCl (0.05 mol/L of Tris base in 0.9 N NaCl, pH 7.5). Substrate solution (disodium P-nitrophenol phosphate, 1.5 mg/ml and 100 p.1 per well) is added, and color development is allowed to proceed until absorbance at 405 nm in the positive control wells was 0.8. Levels are determined relative to a standard comprising of pooled sera obtained from well-characterized pANCA ulcerative colitis patients. Results are expressed as ELISA units, which reflect a percentage of the standard. Sera with circulating antineutrophil cytoplasmic IgG antibody that is at or above the about 50 EU are termed ANCA+. Optionally, the subject is treated with a non-anti-TNF therapeutic agent provided herein. In some embodiments, the therapeutic agent comprises an anti-TL1A antibody.

Indirect immunofluorescence assay: Neutrophils separated by dextran sedimentation are re-suspended in PBS, and 100,000 cells are prepared on slides by cytocentrifugation (Cytospin, Shandon Southern Products, Cheshire, U.K.). The slides are fixed in 100% methanol at 4° C. for 10 minutes, air-dried, and stored at −20° C. The sera are tested at a dilution of 1:20, and staining with fluoroscein-labeled F(ab')$_2$ gamma-chain-specific antibody is performed as described. Slides were examined by fluorescence microscopy (40×Epifluor lens, Carl Zeiss, Inc., Thornwood, N.Y.).

Example 9

Phase 1 Clinical Trial

A phase 1 clinical trial is performed to evaluate the safety, tolerability, pharmacokinetics and pharmacodynamics of an anti-TL1A antibody on subjects having an inflammatory disease or condition, or fibrostenotic and/or fibrotic disease.

Single ascending dose (SAD) arms: Subjects in each group (subjects are grouped based on the presence of a level of ANCA at or above 100 ELISA units (EU), or the presence of a level of ANCA below the 100 EU and above 50 EU, and either of (i) a presence of the TNFRSF1B SNP, and (ii) decreased TNFR2 levels as compared in an individual who does not express the TNFRSF1B SNP) receive either a single dose of the antibody or a placebo. Exemplary doses are 1, 3, 10, 30, 100, 300, 600 and 800 mg of antibody. Safety monitoring and PK assessments are performed for a predetermined time. Based on evaluation of the PK data, and if the antibody is deemed to be well tolerated, dose escalation occurs, either within the same groups or a further group of healthy subjects. Dose escalation continues until the maximum dose has been attained unless predefined maximum exposure is reached or intolerable side effects become apparent.

Multiple Ascending Dose (MAD) Arms:

Subjects in each group (subjects are grouped based on the same criteria as above) receive multiple doses of the antibody or a placebo. The dose levels and dosing intervals are selected as those that are predicted to be safe from the SAD data. Dose levels and dosing frequency are chosen to achieve therapeutic drug levels within the systemic circulation that are maintained at steady state for several days to allow appropriate safety parameters to be monitored. Samples are collected and analyzed to determination PK profiles.

Inclusion Criteria:

Healthy subjects of non-childbearing potential between the ages of 18 and 55 years. Healthy is defined as no clinically relevant abnormalities identified by a detailed medical history, full physical examination, including blood pressure and pulse rate measurement, 12 lead ECG and clinical laboratory tests. Female subjects of non-childbearing potential must meet at least one of the following criteria: (1) achieved postmenopausal status, defined as: cessation of regular menses for at least 12 consecutive months with no alternative pathological or physiological cause; and have a serum follicle stimulating hormone (FSH) level within the laboratory's reference range for postmenopausal females; (2) have undergone a documented hysterectomy and/or bilateral oophorectomy; (3) have medically confirmed ovarian failure. All other female subjects (including females with tubal ligations and females that do NOT have a documented hysterectomy, bilateral oophorectomy and/or ovarian failure) will be considered to be of childbearing potential. Body Mass Index (BMI) of 17.5 to 30.5 kg/m2; and a total body weight >50 kg (110 lbs). Evidence of a personally signed and dated informed consent document indicating that the subject (or a legal representative) has been informed of all pertinent aspects of the study.

Inclusion Criteria:

Three groups of subjects are selected: (1) subjects having a presence of the level of ANCA at or above 100 EU, (2) subjects having a presence of the level of ANCA below 100 EU and above 50 EU and either (i) a presence of the TNFRSF1B SNP, or (ii) decreased TNFR2 levels as compared in an individual who does not express the TNFRSF1B SNP, and (3) subjects lacking a level of ANCA that is high related to a healthy individual.

Exclusion Criteria:

Evidence or history of clinically significant hematological, renal, endocrine, pulmonary, gastrointestinal, cardiovascular, hepatic, psychiatric, neurologic, or allergic disease (including drug allergies, but excluding untreated, asymptomatic, seasonal allergies at time of dosing). Subjects with a history of or current positive results for any of the following serological tests: Hepatitis B surface antigen (HBsAg), Hepatitis B core antibody (HBcAb), anti-Hepatitis C antibody (HCV Ab) or human immunodeficiency virus (HIV). Subjects with a history of allergic or anaphylactic reaction to a therapeutic drug. Treatment with an investigational drug within 30 days (or as determined by the local requirement, whichever is longer) or 5 half-lives or 180 days for biologics preceding the first dose of study medication. Pregnant females; breastfeeding females; and females of childbearing potential.

Primary Outcome Measures:

Incidence of dose limiting or intolerability treatment related adverse events (AEs) [Time Frame: 12 weeks]. Incidence, severity and causal relationship of treatment emergent AEs (TEAEs) and withdrawals due to treatment emergent adverse events [Time Frame: 12 weeks]. Incidence and magnitude of abnormal laboratory findings [Time Frame: 12 weeks]. Abnormal and clinically relevant changes in vital signs, blood pressure (BP) and electrocardiogram (ECG) parameters [Time Frame: 12 weeks].

Secondary Outcome Measures:

Single Ascending Dose: Maximum Observed Plasma Concentration (Cmax) [Time Frame: 12 weeks]. Single Ascending Dose: Time to Reach Maximum Observed Plasma Concentration (Tmax) [Time Frame: 12 weeks]. Single Ascending Dose: Area under the plasma concentration-time profile from time zero to 14 days (AUC14 days) [Time Frame: 12 weeks]. Single Ascending Dose: Area under the plasma concentration-time profile from time zero extrapolated to infinite time (AUCinf) [Time Frame: 12 weeks]. Single Ascending Dose: Area under the plasma concentration-time profile from time zero to the time of last quantifiable concentration (AUClast) [Time Frame: 12 weeks]. Single Ascending Dose: Dose normalized maximum plasma concentration (Cmax[dn]) [Time Frame: 12 weeks]. Single Ascending Dose: Dose normalized area under the plasma concentration-time profile from time zero extrapolated to infinite time (AUCinf[dn]) [Time Frame: 12 weeks]. Single Ascending Dose: Dose normalized area under the plasma concentration-time profile from time zero to the time of last quantifiable concentration (AUClast[dn]) [Time Frame: 12 weeks]. Single Ascending Dose: Plasma Decay Half-Life (t½) [Time Frame: 12 weeks]. Plasma decay half-life is the time measured for the plasma concentration to decrease by one half. Single Ascending Dose: Mean residence time (MRT) [Time Frame: 12 weeks]. Single Ascending Dose: Volume of Distribution at Steady State (Vss) [Time Frame: 6 weeks]. Volume of distribution is defined as the theoretical volume in which the total amount of drug would need to be uniformly distributed to produce the desired blood concentration of a drug. Steady state volume of distribution (Vss) is the apparent volume of distribution at steady-state. Single Ascending Dose: Systemic Clearance (CL) [Time Frame: 6]. CL is a quantitative measure of the rate at which a drug substance is removed from the body.

Multiple Ascending Dose First Dose: Maximum Observed Plasma Concentration (Cmax) [Time Frame: 12 weeks]. Multiple Ascending Dose First Dose: Time to Reach Maximum Observed Plasma Concentration (Tmax) [Time Frame: 12 weeks]. Multiple Ascending Dose First Dose: Area under the plasma concentration-time profile from time zero to time τ, the dosing interval where τ=2 weeks (AUCτ) [Time Frame: 12 weeks]. Multiple Ascending Dose First Dose: Dose normalized maximum plasma concentration (Cmax[dn]) [Time Frame: 12 weeks]. Multiple Ascending Dose First Dose: Dose normalized Area under the plasma concentration-time profile from time zero to time τ, the dosing interval where τ=2 weeks (AUCτ[dn]) [Time Frame: 12 weeks]. Plasma Decay Half-Life (t½) [Time Frame: 12 weeks]. Plasma decay half-life is the time measured for the plasma concentration to decrease by one half. Multiple Ascending Dose First Dose: Mean residence time (MRT) [Time Frame: 12 weeks]. Apparent Volume of Distribution (Vz/F) [Time Frame: 12 weeks]. Volume of distribution is defined as the theoretical volume in which the total amount of drug would need to be uniformly distributed to produce the desired plasma concentration of a drug. Apparent volume of distribution after oral dose (Vz/F) is influenced by the fraction absorbed. Multiple Ascending Dose First Dose: Volume of Distribution at Steady State (Vss) [Time Frame: 12 weeks]. Volume of distribution is defined as the theoretical volume in which the total amount of drug would need to be uniformly distributed to produce the desired blood concentration of a drug. Steady state volume of distribution (Vss) is the apparent volume of distribution at steady-state. Multiple Ascending Dose First Dose: Apparent Oral Clearance (CL/F) [Time Frame: 12 weeks]. Clearance of a drug is a measure of the rate at which a drug is metabolized or eliminated by normal biological processes. Clearance obtained after oral dose (apparent oral clearance) is influenced by the fraction of the dose absorbed. Clearance is estimated from population pharmacokinetic (PK) modeling. Drug clearance is a quantitative measure of the rate at which a drug substance is removed from the blood. Multiple Ascending Dose First Dose: Systemic Clearance (CL) [Time Frame: 12 weeks]. CL is a quantitative measure of the rate at which a drug substance is removed from the body.

Multiple Ascending Dose Multiple Dose: Maximum Observed Plasma Concentration (Cmax) [Time Frame: 12 weeks]. Multiple Ascending Dose Multiple Dose: Time to Reach Maximum Observed Plasma Concentration (Tmax) [Time Frame: 12 weeks]. Multiple Ascending Dose Multiple Dose: Area under the plasma concentration-time profile from time zero to time τ, the dosing interval where i=2 weeks (AUCτ) [Time Frame: 12 weeks]. Multiple Ascending Dose Multiple Dose: Dose normalized maximum plasma concentration (Cmax[dn]) [Time Frame: 12 weeks]. Multiple Ascending Dose Multiple Dose: Dose normalized Area under the plasma concentration-time profile from time zero to time τ, the dosing interval where τ=2 weeks (AUCτ [dn]) [Time Frame: 12 weeks]. Multiple Ascending Dose Multiple Dose: Plasma Decay Half-Life (t½) [Time Frame: 12 weeks]. Plasma decay half-life is the time measured for the plasma concentration to decrease by one half. Multiple Ascending Dose Multiple Dose: Apparent Volume of Distribution (Vz/F) [Time Frame: 12 weeks]. Volume of distribution is defined as the theoretical volume in which the total amount of drug would need to be uniformly distributed to produce the desired plasma concentration of a drug. Apparent volume of distribution after oral dose (Vz/F) is influenced by the fraction absorbed. Multiple Ascending Dose Multiple Dose: Volume of Distribution at Steady State (Vss) [Time Frame: 12 weeks]. Volume of distribution is defined as the theoretical volume in which the total amount of drug would need to be uniformly distributed to produce the desired blood concentration of a drug. Steady state volume of distribution (Vss) is the apparent volume of distribution at steady-state.

Multiple Ascending Dose Multiple Dose: Apparent Oral Clearance (CL/F) [Time Frame: 12 weeks]. Clearance of a drug is a measure of the rate at which a drug is metabolized or eliminated by normal biological processes. Clearance obtained after oral dose (apparent oral clearance) is influenced by the fraction of the dose absorbed. Clearance was estimated from population pharmacokinetic (PK) modeling. Drug clearance is a quantitative measure of the rate at which a drug substance is removed from the blood. Multiple Ascending Dose Multiple Dose: Systemic Clearance (CL) [Time Frame: 12 weeks]. CL is a quantitative measure of the rate at which a drug substance is removed from the body. Multiple Ascending Dose Multiple Dose: Minimum Observed Plasma Trough Concentration (Cmin) [Time Frame: 12 weeks]. Multiple Ascending Dose Multiple Dose: Average concentration at steady state (Cav) [Time Frame: 12 weeks]. Multiple Ascending Dose Multiple Dose: Observed accumulation ratio (Rac) [Time Frame: 12 weeks]. Multiple Ascending Dose Multiple Dose: Peak to trough fluctuation (PTF) [Time Frame: 12 weeks]. Multiple Ascending Dose Additional Parameter: estimate of bioavailability (F) for subcutaneous administration at the corresponding intravenous dose [Time Frame: 12 weeks]. Immunogenicity for both Single Ascending Dose and Multiple Ascending Dose: Development of anti-drug antibodies (ADA) [Time Frame: 12 weeks].

Example 10

Phase 1B Clinical Trial

A phase 1b open label clinical trial is performed to evaluate efficacy of an anti-TL1A antibody on subjects having an inflammatory disease or condition or fibrostenotic and/or fibrotic disease.

Arms:

5 patients positive a presence of the level of ANCA at or above 100 ELISA units (EU) are administered the antibody. 5 patients positive for a presence of a level of ANCA below the 100 EU and above 50 EU and either of (i) a presence of the TNFRSF1B SNP, and (ii) decreased TNFR2 levels as compared in an individual who does not express the TNFRSF1B SNP, are administered the antibody. 5-10 patients negative for a high level of ANCA relative to a healthy individual are administered the antibody. Patients are monitored in real-time. Central ready of endoscopy and biopsy is employed, with readers blinded to point of time of treatment and endpoints.

Inclusion Criteria:

Three groups of subjects are selected: (1) subjects having a presence of the level of ANCA at or above 100 EU, (2) subjects having a presence of the level of ANCA below 100 EU and above 50 EU and either (i) a presence of the TNFRSF1B SNP, or (ii) decreased TNFR2 levels as compared in an individual who does not express the TNFRSF1B SNP, and (3) subjects lacking a level of ANCA that is high related to a healthy individual.

Primary Outcome Measures:

Simple Endoscopic Score for Crohn's Disease (SESCD), Crohn's Disease Activity Index (CDAI), and Patient Reported Outcome (PRO). If risk either positive group shows 50% reduction from baseline, a Phase 2a clinical trial is performed.

Inclusion Criteria:

PRO entry criteria: Abdominal pain score of 2 or more and/or stool frequency score of 4 or more. Primary outcome would be pain core of 0 or 1 and stool frequency score of 3 or less with no worsening from baseline. Endoscopy entry criteria: SESCD ileum only entry at score of 4 and 6 if colon is involved. Primary endoscopic outcome is 40-50% delta of mean SESCD.

Example 11

Phase 2A Clinical Trial

A phase 2a clinical trial is performed to evaluate the efficacy of an anti-TL1A antibody in subjects having an inflammatory disease or condition, or fibrostenotic and/or fibrotic disease.

Arms:

40 patients per arm (antibody and placebo arms) are treated with antibody or placebo for 12 weeks. An interim analysis is performed after 20 patients from each group are treated at the highest dose to look for a 40-50% delta between placebo and treated group in primary outcome (50% reduction from baseline in SESCD, CDAI, and PRO).

Primary Outcome Measures:

Simple Endoscopic Score for Crohn's Disease (SESCD), Crohn's Disease Activity Index (CDAI), and Patient Reported Outcome (PRO).

Inclusion Criteria:

PRO entry criteria: Abdominal pain score of 2 or more and/or stool frequency score of 4 or more. Primary outcome would be pain core of 0 or 1 and stool frequency score of 3 or less with no worsening from baseline. Endoscopy entry criteria: SESCD ileum only entry at score of 4 and 6 if colon is involved. Primary endoscopic outcome is 40-50% delta of mean SESCD.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the aspects disclosed herein are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the aspects disclosed herein known to the applicant at this time of filing the application has been presented and is intended for the purposes of illustration and description. The present description is not intended to be exhaustive nor limit the aspects disclosed herein to the precise form disclosed and many modifications and variations are possible in the light of the above teachings. The embodiments described serve to explain the principles of the aspects disclosed herein and its practical application and to enable others skilled in the art to utilize the aspects disclosed herein in various embodiments and with various modifications as are suited to the particular use contemplated. Therefore, it is intended that the aspects disclosed herein not be limited to the particular embodiments disclosed for carrying out the aspects disclosed herein.

While particular embodiments of the aspects disclosed herein have been shown and described, it will be obvious to those skilled in the art that, based upon the teachings herein, changes and modifications may be made without departing from the aspects disclosed herein and its broader aspects and, therefore, the appended claims are to encompass within their scope all such changes and modifications as are within the true spirit and scope of the aspects disclosed herein.

The invention claimed is:

1. A method of treating a subject with an inflammatory, fibrostenotic, or fibrotic disease or condition, comprising administering to the subject a therapeutically effective amount of a therapeutic agent, provided a presence of a genetic risk variant at rs5745994 comprising a "C" allele at nucleobase position 76 within SEQ ID NO: 1 at a gene locus TNFRSF1B is detected in a biological sample obtained from the subject.

2. The method of claim 1, wherein a decreased level of Tumor necrosis factor receptor 2 (TNFR2) is detected in a sample obtained from the subject, compared to a reference value obtained from an individual who is not a carrier of the genetic risk variant.

3. The method of claim 1, wherein a level of ANCA is detected in a biological sample obtained from the subject that is at or above a first threshold level comprising about 100 ELISA units (EU).

4. The method of claim 1, wherein a level of ANCA is detected in a biological sample obtained from the subject that is lower than a first threshold level comprising about 100 ELISA units (EU) and higher than a second threshold level comprising about 50 EU.

5. The method of claim 4, wherein the level of ANCA and the presence of the risk variant is indicative that the subject is non-responsive, or susceptible to non-response, to anti-Tumor Necrosis Factor alpha (TNFα) therapy.

6. The method of claim 4, wherein the level of ANCA, the presence of the genetic risk variant, and a decreased level of TNFR2 as compared to a reference value obtained from an individual who is not a carrier of the genetic risk variant, detected in the biological sample obtained from the subject is indicative that the subject is nonresponsive, or susceptible to non-response, to anti-TNFα therapy.

7. The method of claim 1, wherein the presence of the genetic risk variant detected in the biological sample obtained from the subject is indicative that the subject is non-responsive, or susceptible to non-response, to anti-TNFα therapy.

8. The method of claim 1, wherein a level of ANCA is detected in a biological sample obtained from the subject using an assay comprising an anti-ANCA antibody.

9. The method of claim 1, wherein the inflammatory, fibrostenotic, or fibrotic disease or condition comprises inflammatory bowel disease (IBD), Crohn's disease (CD), perianal Crohn's disease (pCD), ulcerative colitis (UC), rheumatoid arthritis, multiple sclerosis, psoriasis, chronic colitis, pancreatitis, leukopenia, colonic fibrosis, primary sclerosing cholangitis, progressive systemic sclerosis, chronic asthma, or fibrostenosis of a small and/or large intestine, or a combination thereof.

10. The method of claim 1, wherein the genetic risk variant is detected by contacting the biological sample obtained from the subject with a nucleic acid molecule comprising a nucleic acid sequence capable of hybridizing to 10 contiguous nucleobases of SEQ ID NO. 1 spanning nucleobase 76 within SEQ ID NO: 1 under standard hybridization conditions.

11. The method of claim 10, wherein the standard hybridization conditions comprise an annealing temperature between about 30° C. and about 65° C.

12. A method comprising:
(a) assaying to detect in a biological sample obtained from a subject with an inflammatory, fibrostenotic, or fibrotic disease or condition, a level of antineutrophil cytoplasmic antibody (ANCA), a presence of a genetic risk variant comprising a risk allele at rs5745994 comprising a "C" allele at nucleobase position 76 within SEQ ID NO: 1 at a gene locus TNFRSF1B, or a combination thereof;
(b) identifying the subject as being non-responsive to anti-TNFα therapy, or susceptible to non-response to anti-TNFα therapy, provided (i) a level of ANCA that is at or above a first threshold level comprising about 100 ELISA units (EU), or (ii) a level of ANCA that is lower than the first threshold level and above a second threshold level comprising about 50 EU, and the presence of the genetic risk variant, are detected in the biological sample obtained from the subject; and
(c) treating, or prescribing a treatment for, the inflammatory, fibrostenotic, or fibrotic disease or condition in the subject, provided the subject is identified as being non-responsive to anti-TNFα therapy, or susceptible to non-response to anti-TNFα therapy.

13. The method of claim 12, wherein treating the inflammatory, fibrostenotic, or fibrotic disease or condition in the subject of (c) further comprises administering to the subject a therapeutically effective amount of a therapeutic agent.

14. The method of claim 12, wherein the inflammatory, fibrostenotic, or fibrotic disease or condition comprises inflammatory bowel disease (IBD), Crohn's disease (CD), perianal Crohn's disease (pCD), ulcerative colitis (UC), rheumatoid arthritis, multiple sclerosis, psoriasis, chronic colitis, pancreatitis, leukopenia, colonic fibrosis, primary sclerosing cholangitis, progressive systemic sclerosis, chronic asthma, or fibrostenosis of a small and/or large intestine, or a combination thereof.

15. The method of claim 12, further comprising assaying to detect a level of TNFR2, wherein a decrease in TNFR2, compared to a reference value obtained from an individual who is not a carrier of the genetic risk variant, is indicative of non-response to anti-TNFα therapy in the subject.

16. The method of claim 12, wherein the level of ANCA is detected using an assay comprising an anti-ANCA antibody.

17. The method of claim 16, where the assay comprises a neutrophil-fixed enzyme-linked immunosorbent assay (neutrophil fixed-ELISA).

18. The method of claim 12, wherein the genetic risk variant is detected by contacting the sample obtained from the subject with a nucleic acid molecule comprising a nucleic acid sequence capable of hybridizing to 10 contiguous nucleobases of SEQ ID NO. 1 spanning nucleobase 76 within SEQ ID NO: 1 under standard hybridization conditions, wherein the standard hybridization conditions comprise an annealing temperature between about 30° C. and about 65° C.

* * * * *